US012735442B2

(12) United States Patent
Shin et al.

(10) Patent No.: US 12,735,442 B2
(45) Date of Patent: Sep. 15, 2026

(54) TRANSITION METAL COMPLEX CONTAINING TETRADENTATE NITROGEN DONOR LIGAND AND ELECTROCHEMICAL BIOSENSOR COMPRISING SAME

(71) Applicants: I-sens, Inc., Seoul (KR); SOGANG UNIVERSITY RESEARCH & BUSINESS DEVELOPMENT FOUNDATION, Seoul (KR)

(72) Inventors: Hyunseo Shin, Seoul (KR); Bongjin Moon, Goyang-si (KR); Hoejun Kwon, Seoul (KR)

(73) Assignees: I-SENS, INC., Seoul (KR); SOGANG UNIVERSITY RESEARCH & BUSINESS DEVELOPMENT FOUNDATION, Seoul (KR)

( * ) Notice: Subject to any disclaimer, the term of this patent is extended or adjusted under 35 U.S.C. 154(b) by 465 days.

(21) Appl. No.: 18/269,062

(22) PCT Filed: Dec. 28, 2021

(86) PCT No.: PCT/KR2021/020070
§ 371 (c)(1),
(2) Date: Jun. 22, 2023

(87) PCT Pub. No.: WO2022/145982
PCT Pub. Date: Jul. 7, 2022

(65) Prior Publication Data

US 2024/0158426 A1 May 16, 2024

(30) Foreign Application Priority Data

Dec. 31, 2020 (KR) ........................ 10-2020-0189139

(51) Int. Cl.
*C12Q 1/00* (2006.01)
*A61B 5/145* (2006.01)
(Continued)

(52) U.S. Cl.
CPC .......... *C07F 15/00* (2013.01); *A61B 5/14532* (2013.01); *A61B 5/14865* (2013.01);
(Continued)

(58) Field of Classification Search
CPC ................ C07F 15/00; A61B 5/14532; A61B 5/14865; C12Q 1/005; G01N 27/327-3272; G01N 27/3277
See application file for complete search history.

(56) References Cited

U.S. PATENT DOCUMENTS

| | | | | |
|---|---|---|---|---|
| 6,605,201 | B1 | 8/2003 | Mao et al. | |
| 2008/0197026 | A1 | 8/2008 | Mao et al. | |
| 2011/0017595 | A1 * | 1/2011 | Mao .................. | A61B 5/14546 204/403.14 |

FOREIGN PATENT DOCUMENTS

| | | |
|---|---|---|
| CN | 1620462 | 5/2005 |
| CN | 116940609 | 10/2023 |

(Continued)

OTHER PUBLICATIONS

Sugimoto et al., "Synthesis and Properties of Oxo-carboxylato- and Dioxo-Bridged Diosmium Complexes of Tris(2-pyridylmethyl) amine," Inorg. Chem. 2011, 50, 9014-9023 (Year: 2011).*

(Continued)

*Primary Examiner* — Alexander S Noguerola
(74) *Attorney, Agent, or Firm* — LEX IP MEISTER, PLLC

(57) ABSTRACT

The present invention relates to: a novel transition metal complex containing a tetradentate nitrogen donor ligand, which can be used in various devices including electrochemical sensors; and a device comprising same, preferably an electrochemical sensor.

4 Claims, 20 Drawing Sheets

24 $R^1$ = H, $R^2$ = H, $L^1$, $L^2$ = 4-methoxy-2-pyridylcarboxamide (40% yield)
25 $R^1$ = H, $R^2$ = H, $L^1$, $L^2$ = N-methylimidazole (85% yield)
26 $R^1$ = H, $R^2$ = H, $L^1$ = pyridine, $L^2$ = Cl (29% yield)
27 $R^1$ = H, $R^2$ = H, $L^1$, $L^2$ = 4-bromopicolinic acid (75% yield)
28 $R^1$ = H, $R^2$ = H, $L^1$, $L^2$ = catechol, (62% yield)
29 $R^1$ = H, $R^2$ = H, $L^1$, $L^2$ = picolinic acid, (53%, yield)
30 $R^1$ = H, $R^2$ = H, $L^1$, $L^2$ = acetylacetone, (50%, yield)
31 $R^1$ = $CH_2OH$, $R^2$ = H, $L^1$, $L^2$ = picolinic acid, (51% yield)
32 $R^1$ = $CH_2OH$, $R^2$ = H, $L^1$, $L^2$ = 4-methylpicolinic acid, (53% yield)
33 $R^1$ = $CONHCH_2CH_2NH_2$, $R^2$ = H, $L^1$, $L^2$ = 4-methylpicolinic acid, (28% yield)
34 $R^1$ = $CONHCH_2CH_2NH_2$, $R^2$ = H, $L^1$, $L^2$ = N-methylimidazole, (96% yield)
35 $R^1$ = MeO, $R^2$ = MeO, $L^1$, $L^2$ = N-methylimidazole, (80% yield)

(51) Int. Cl.
*A61B 5/1486* (2006.01)
*C07F 15/00* (2006.01)
*G01N 27/327* (2006.01)

(52) U.S. Cl.
CPC ............ *C12Q 1/004* (2013.01); *C12Q 1/005* (2013.01); *G01N 27/3271* (2013.01); *G01N 27/3277* (2013.01)

(56) References Cited

FOREIGN PATENT DOCUMENTS

| | | |
|---|---|---|
| EP | 4273181 | 11/2023 |
| JP | 2003-514924 | 4/2003 |
| JP | 2006-509837 | 3/2006 |
| WO | 2013-126745 | 8/2013 |

OTHER PUBLICATIONS

Sugimoto et al., "Comparative Structural, Spectroscopic and Redox Studies of Isostructural Complexes of Ruthenium(III), Osmium(III), and Rhenium(III): cis-Dichloro Complexes Containing Tris(2-pyridylmethyl)amine and Its 6-Methylpyridyl Derivative," Bull. Chem. Soc. Jpn., 74, 2091-2099 (2001) (Year: 2001).*
O'Neill et al., "Hypoxia-Responsive Cobalt Complexes in Tumor Spheroids: Laser Ablation Inductively Coupled Plasma Mass Spectrometry and Magnetic Resonance Imaging Studies," Inorg. Chem. 2017, 56, 9860-9868 (Year: 2017).*
Green et al., "The influence of the ancillary ligand on the potential of cobalt(III) complexes to act as chaperones for hydroxamic acid-based drugs," Dalton Trans., 2017, 46, 15897 (Year: 2017).*
Khusnutdinova et al., "Late First-Row Transition Metal Complexes of a Tetradentate Pyridinophane Ligand: Electronic Properties and Reactivity Implications," Inorg. Chem. 2013, 52, 3920-3932 (Year: 2013).*
Nakabayashi et al., "Evaluation of Osmium(II) Complexes as Electron Transfer Mediators Accessible for Amperometric Glucose Sensors," Analytical Sciences Aug. 2001, vol. 17 (Year: 2013).*
Ganesh et al., "Metal-mediated transport of electrons across molecular films," Chem. Commun., 2007,804-806 (Year: 2007).*
English language translation of Written Opinion for international application No. PCT/KR2021/020070, mailed Apr. 11, 2022 (Year: 2022).*
KIPO, PCT Search Report & Written Opinion of PCT/KR2021/020070 dated Apr. 11, 2022.
Ao Li et al., "Selective Release of Aromatic Heterocycles from Ruthenium Tris(2-pyridylmethyl)amine with Visible Light", Inorganic Chemistry, 2016, 10-12.
Anna K. Renfrew et al., "Delivery and release of curcumin by a hypoxia-activated cobalt chaperone: a XANES and FLIM study", Chemical Science, 2013, 3731-3739.
E. S. O'Neill et al., "Reversible magnetogenic cobalt complexes", RSC Advances, 2016, 30021-30027.
Takahiko Kojima et al., "Synthesis and Characterization of Mononuclear RutheniumAchtungtrenung(III) Pyridylamine Complexes and Mechanistic Insights into Their Catalytic Alkane Functionalization with m-Chloroperbenzoic Acid", S. Chem. Eur. J.2007, 13, 8212-8222.
Weisser, F. et al, "Tuning Ligand Effects and Probing the Inner-Workings of Bond Activation Steps: Generation of Ruthenium Complexes with Tailor-Made Properties", Inorganic Chemistry, 2015, 54(10), 4621-4635, May 6, 2015.
Hilt, G. et al, "Efficient in-situ redox catalytic NAD(P)+ regeneration in enzymic synthesis using transition-metal complexes of 1,10-phenant hroline-5,6-dione and its N-monomethylated derivative as catalysts", Lieb igs Annalen/Recueil, 1997, (11), 2289-2296.
Sugimoto, H. et al, "Comparative structural, spectroscopic and redox studies of isostructural complexes of ruthenium(III), osmium(III), and r henium(III): cis-dichloro complexes containing tris(2-pyridylmethyl)amin e and its 6-methylpyridyl derivative", Bulletin of the Chemical Society of Japan, 2001, 74(11), 2091-2099, Dec. 1, 2002.
Sugimoto, H. et al, "Osmium(III) and Osmium(V) Complexes Bearing a Ma crocyclic Ligand: A Simple and Efficient Catalytic System for cis-Dihydr oxylation of Alkenes with Hydrogen Peroxide", Chemistry an Asian Journal, 2013, 8(9), 2154-2160, May 7, 2013.
Li, A. et al, "Selective Release of Aromatic Heterocycles from Ruthenium Tris(2-pyridylmethyl)amine with Visible Light", Inorganic Chemistry, Jan. 4, 2016, 55(1), 10-12.
Renfrew, A. K. et al, "Delivery and release of curcumin by a hypoxia-activated cobalt chaperone: a XANES and FLIM study", Chemical Science, 4( 9), 2013, 3731-3739, Jul. 10, 2013.
O'Neill, E. S. et al, "Reversible magnetogenic cobalt complexes", RSC Advances, 2016, 6(36), 30021-30027, Mar. 23, 2016.
Kojima, T. et al, "Synthesis and characterization of mononuclear ruthenium(III) pyridylamine complexes and mechanistic insights into their catalytic alkane functionalization with m-chloroperbenzoic acid", Chemistry A European Journal, 2007, 13(29), 8212-8222, Oct. 5, 2007.
Cui, Y. et al, "An anion sensor of ruthenium(II) complex based on tris(2-pyridylmethyl) amine", Huaxue Yanjiu, 2012, 23(6), 42-48.
Chen, K. et al, "Stereospecific Alkane Hydroxylation by Non-Heme Iron Catalysts: Mechanistic Evidence for an FeV:O Active Species", Journal of the American Chemical Society, 2001, 123(26), 6327-6337, Jun. 9, 2001.
Sharma, H. et al, "Pyridyl- and benzimidazole-based ruthenium(iii) complex for selective chloride recognition through fluorescence spectroscopy", Analytical Methods, 2013, 5(16), 3880-3887, May 8, 2013.
Sugimoto, H. et al, "An Osmium(III)/Osmium(V) Redox Couple Generating OsV(O)(OH) Center for cis-1,2-Dihydroxylation of Alkenes with H2O2: O s Complex with a Nitrogen-Based Tetradentate Ligand", Journal of the American Chemical Society, 2012, 134(46), 19270-19280, Oct. 30, 2012.
JPO, Office Action of JP 2023-540608 dated Aug. 16, 2024.
Sharon Lai-Fung Chan et al., "Cobalt (II) tris (2-pyridylmethyl) amine complexes [Co (TPA) X]+ bearing coordinating anion (X=Ci-, Br-, I- and NCS-): synthesis and application for carbon dioxide reduction.", Polyhedron, 2017, vol. 125, pp. 156-163, Oct. 5, 2016.
KIPO, Office Action of the corresponding Korean Patent Application No. 10-2020-0189139 dated Feb. 21, 2024, total 26 pages.
EPO, Search Report of EP 21915780.7 dated May 10, 2024.
Gerhard Hilt et al., "Efficient In-Situ Redox Catalytic NAD(P)+ Regeneration in Enzymatic Synthesis Using Transition-Metal Complexes of 1,10-Phenanthroline-5,6-dione and Its N-Monomethylated Derivative as Catalysts", Liebigs Annalen: Organic and Bioorganic Chemistry, vol. 1997, No. 11, Jan. 28, 2006 (Jan. 28, 2006), pp. 2289-2296.
Hideki Sugimoto et al., "Comparative Structural, Spectroscopic and Redox Studies of Isostructural Complexes of Ruthenium(III), Osmium(III), and Rhenium(III): cis-Dichloro Complexes Containing Tris(2-pyridylmethyl)amine and Its 6-Methylpyridyl Derivative", Bulletin of the Chemical Society of Japan, vol. 74, Issue 11, Nov. 2001, pp. 2091-2099, https://doi.org/10.1246/bcsj.74.2091.
Fritz Weisser et al., "Tuning ligand effects and probing the inner-workings of bond activation steps: generation of ruthenium complexes with tailor-made properties", Inorganic Chemistry, vol. 54, No. 10, May 6, 2015 (May 6, 2015), pp. 4621-4635.
Hideki Sugimoto et al., "Osmium(III) and Osmium(V) Complexes Bearing a Macrocyclic Ligand: A Simple and Efficient Catalytic System for cis-Dihydroxylation of Alkenes with Hydrogen Peroxide", Chemistry—An Asian Journal, vol. 8, No. 9, May 7, 2013 (May 7, 2013), pp. 2154-2160.
Database Caplus [Online] Jan. 1, 2012 (Jan. 1, 2012), Y Cui: "An anion sensor of ruthenium(II) complex based on tris(2-pyridylmethyl) amine", XP093153061, Database accession No. 2013:1323676 *abstract*.
Hemant Sharma et al., "Pyridyl- and benzimidazole-based ruthenium(iii) complex for selective chloride recognition through fluorescence spectroscopy", Analytical Methods, vol. 5, No. 16, Jan. 1, 2013 (Jan. 1, 2013), pp. 3880-3887.

(56) References Cited

OTHER PUBLICATIONS

Hideki Sugimoto et al., "Synthesis and Properties of Oxo-carboxylato- and Dioxo-Bridged Diosmium Complexes of Tris (2-pyridylmethyl)amine", Inorganic Chemistry, vol. 50, No. 18, Sep. 19, 2011 (Sep. 19, 2011), pp. 9014-9023.
Kui Chen et al., "Stereospecific Alkane Hydroxylation by Non-Heme Iron Catalysts: Mechanistic Evidence for an FeVO Active Species", Journal of the American Chemical Society, vol. 123, No. 26, Jul. 1, 2001 (Jul. 1, 2001), pp. 6327-6337.
Triloke Ranjan Lakshman et al., "Substrate-dependent aromatic ring fission of catechol and 2-aminophenol with O2 catalyzed by a nonhere iron complex of a tripodal N4 ligand", Dalton Trans., 2016, 45, 6836-8844, Apr. 2016.
Wataru Suzuki et al., "A Diprotonated Porphyrin as an Electron Mediator in Photoinduced Electron Transfer in Hydrogen-Bonded Supramolecular Assemblies", J. Phys. Chem. C 2019, 123, 11529-11538, Apr. 19, 2019.
SIPO, Office Action of the corresponding Chinese Patent Application No. 202180094860.4., dated Jun. 7, 2025, total 20 pages.

* cited by examiner

[FIG. 1]

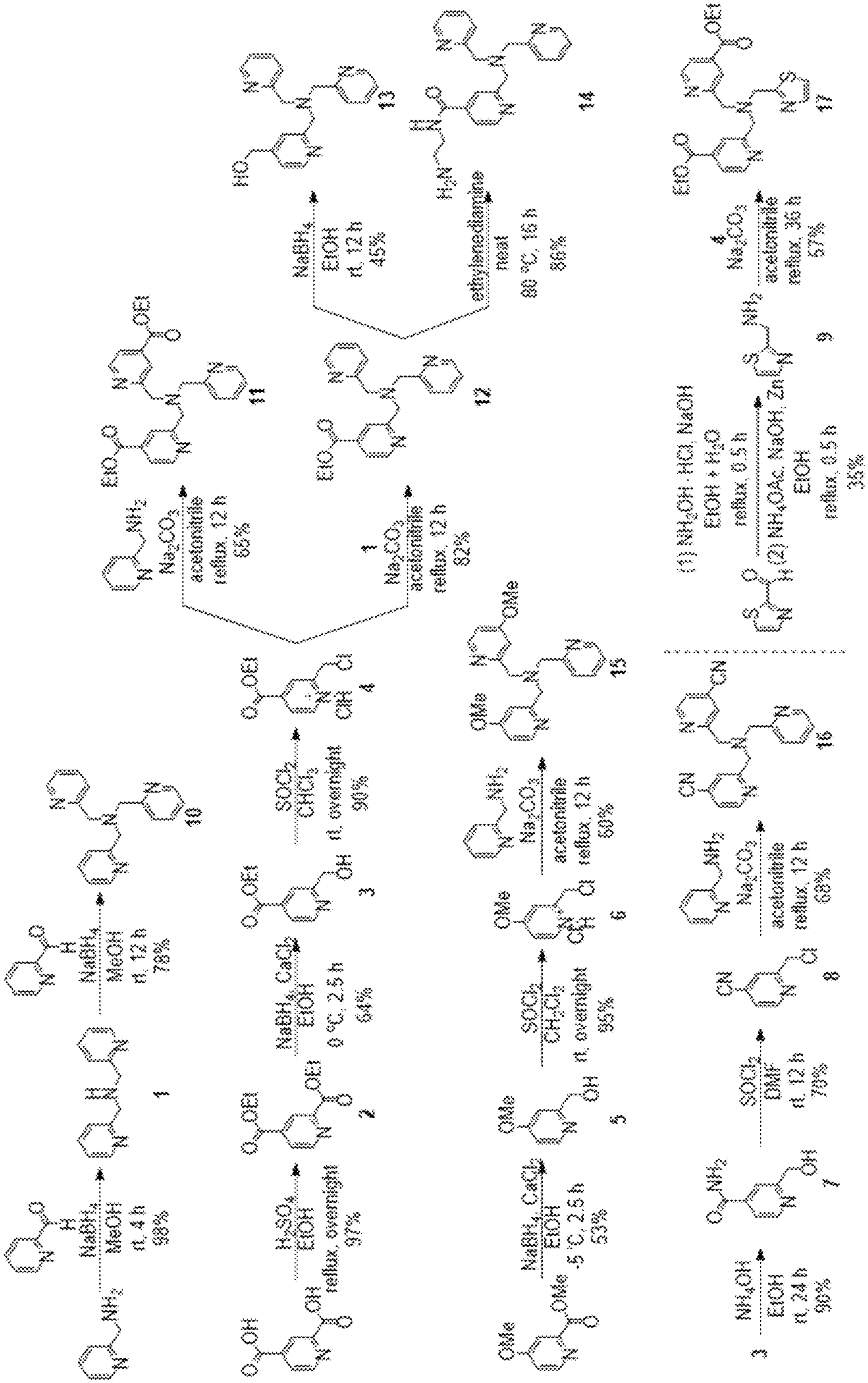

【FIG. 1】

$NaBH_4$
MeOH
rt, 4 h
98%

1

$NaBH_4$
MeOH
rt, 12 h
78%

10

$Na_2CO_3$
acetonitrile
reflux, 12 h
65%

11

$H_2SO_4$
EtOH
reflux, overnight
97%

2

$NaBH_4$, $CaCl_2$
EtOH
0 °C, 2.5 h
64%

3

$SOCl_2$
$CHCl_3$
rt, overnight
90%

4

1
$Na_2CO_3$
acetonitrile
reflux, 12 h
82%

12

$NaBH_4$
EtOH
rt, 12 h
45%

13 ethylenediamine
neat
80 °C, 16 h
86%

14

$NaBH_4$, $CaCl_2$
EtOH
-5 °C, 2.5 h
53%

5

$SOCl_2$
$CH_2Cl_2$
rt, overnight
95%

6

$Na_2CO_3$
acetonitrile
reflux, 12 h
60%

15

3

$NH_4OH$
EtOH
rt, 24 h
90%

7

$SOCl_2$
DMF
rt, 12 h
70%

8

$Na_2CO_3$
acetonitrile
reflux, 12 h
68%

16

(1) $NH_2OH \cdot HCl$, NaOH
EtOH + $H_2O$
reflux, 0.5 h
(2) $NH_4OAc$, NaOH, Zn
EtOH
reflux, 0.5 h
35%

9

4
$Na_2CO_3$
acetonitrile
reflux, 36 h
57%

17

【FIG. 2】
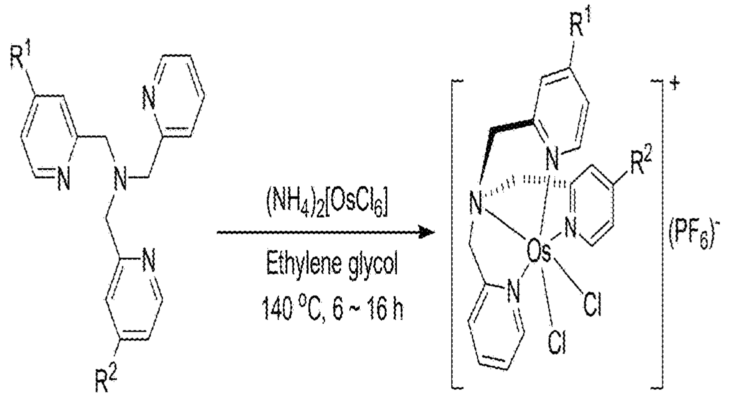
18 $R^1$ = H, $R^2$ = H, (73% yield)
19 $R^1$ = COOEt, $R^2$ = COOEt, (93% yield)
20 $R^1$ = COOEt, $R^2$ = H, (90% yield)
21 $R^1$ = $CH_2OH$, $R^2$ = H, (50% yield)
22 $R^1$ = $CONHCH_2CH_2NH_2$, $R^2$ = H, (61% yield)
23 $R^1$ = MeO, $R^2$ = MeO, (95%, yield)

【FIG. 3】
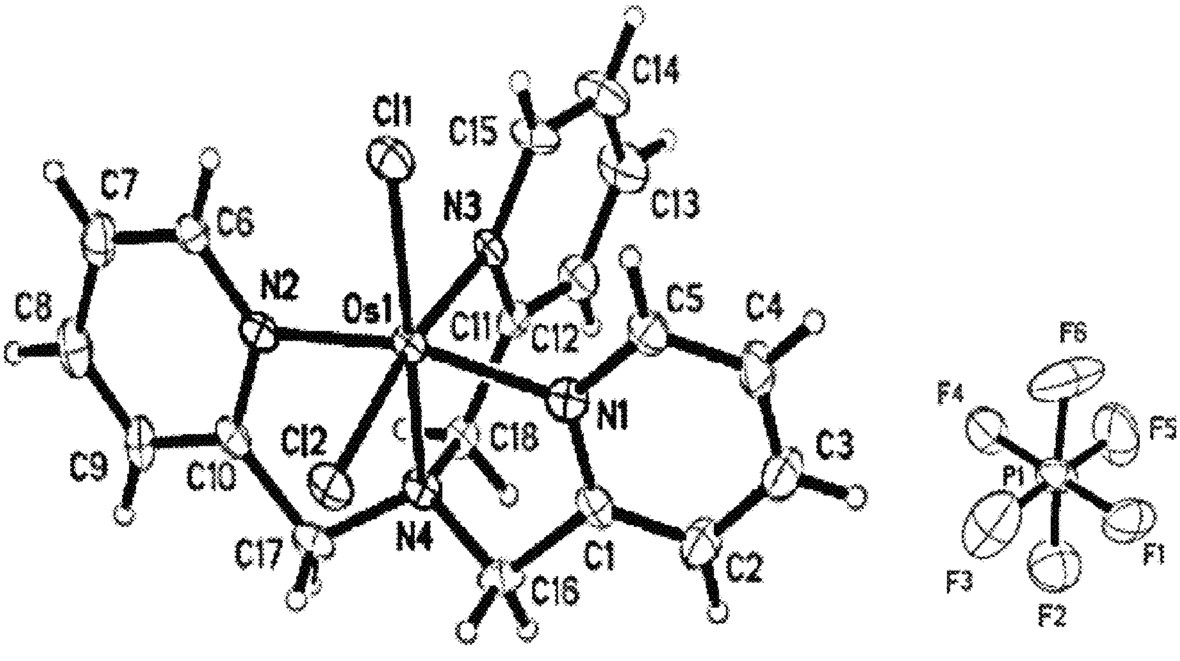

【FIG. 4】

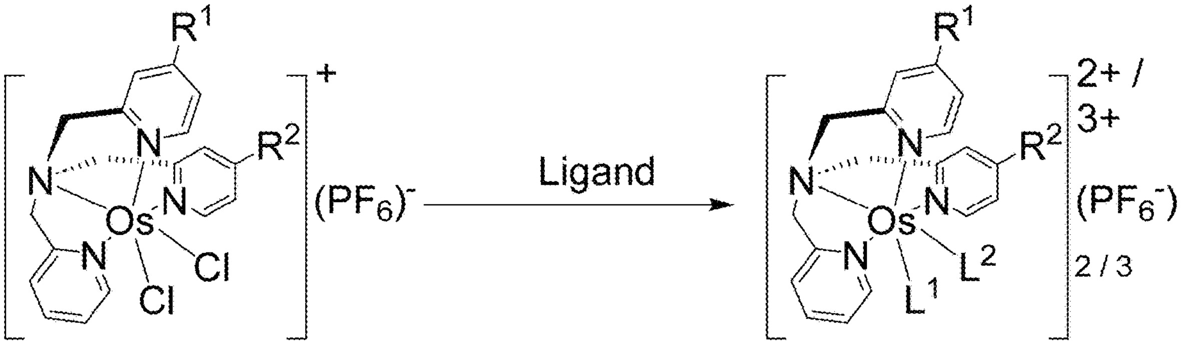

24 $R^1$ = H, $R^2$ = H, $L^1$, $L^2$ = 4-methoxy-2-pyridylcarboxamide (40% yield)
25 $R^1$ = H, $R^2$ = H, $L^1$, $L^2$ = N-methylimidazole (85% yield)
26 $R^1$ = H, $R^2$ = H, $L^1$ = pyridine, $L^2$ = Cl (29% yield)
27 $R^1$ = H, $R^2$ = H, $L^1$, $L^2$ = 4-bromopicolinic acid (75% yield)
28 $R^1$ = H, $R^2$ = H, $L^1$, $L^2$ = catechol, (62% yield)
29 $R^1$ = H, $R^2$ = H, $L^1$, $L^2$ = picolinic acid, (53%, yield)
30 $R^1$ = H, $R^2$ = H, $L^1$, $L^2$ = acetylacetone, (50%, yield)
31 $R^1$ = $CH_2OH$, $R^2$ = H, $L^1$, $L^2$ = picolinic acid, (51% yield)
32 $R^1$ = $CH_2OH$, $R^2$ = H, $L^1$, $L^2$ = 4-methylpicolinic acid, (53% yield)
33 $R^1$ = $CONHCH_2CH_2NH_2$, $R^2$ = H, $L^1$, $L^2$ = 4-methylpicolinic acid, (28% yield)
34 $R^1$ = $CONHCH_2CH_2NH_2$, $R^2$ = H, $L^1$, $L^2$ = N-methylimidazole, (96% yield)
35 $R^1$ = MeO, $R^2$ = MeO, $L^1$, $L^2$ = N-methylimidazole, (80% yield)

【FIG. 5】
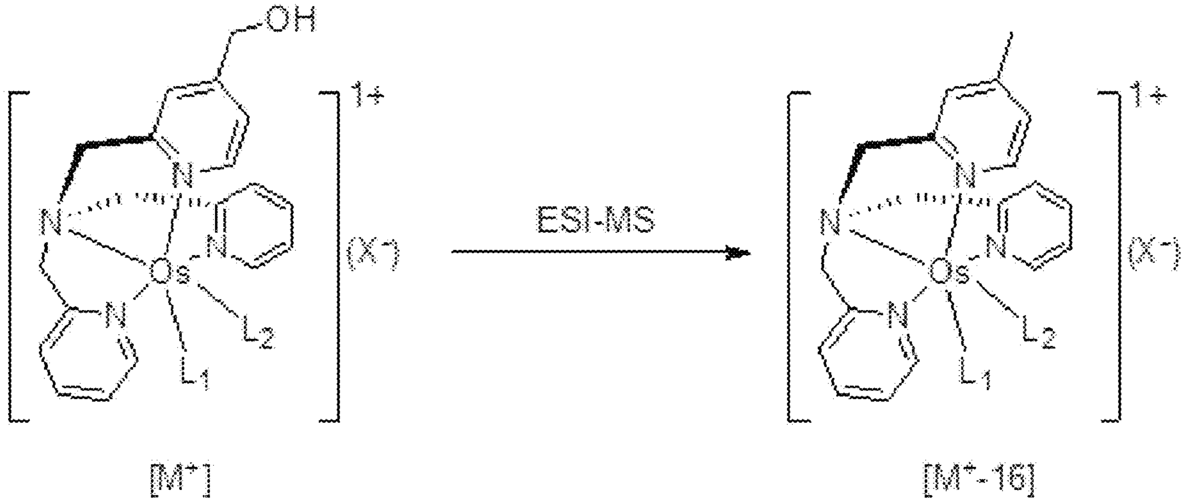

【FIG. 6】
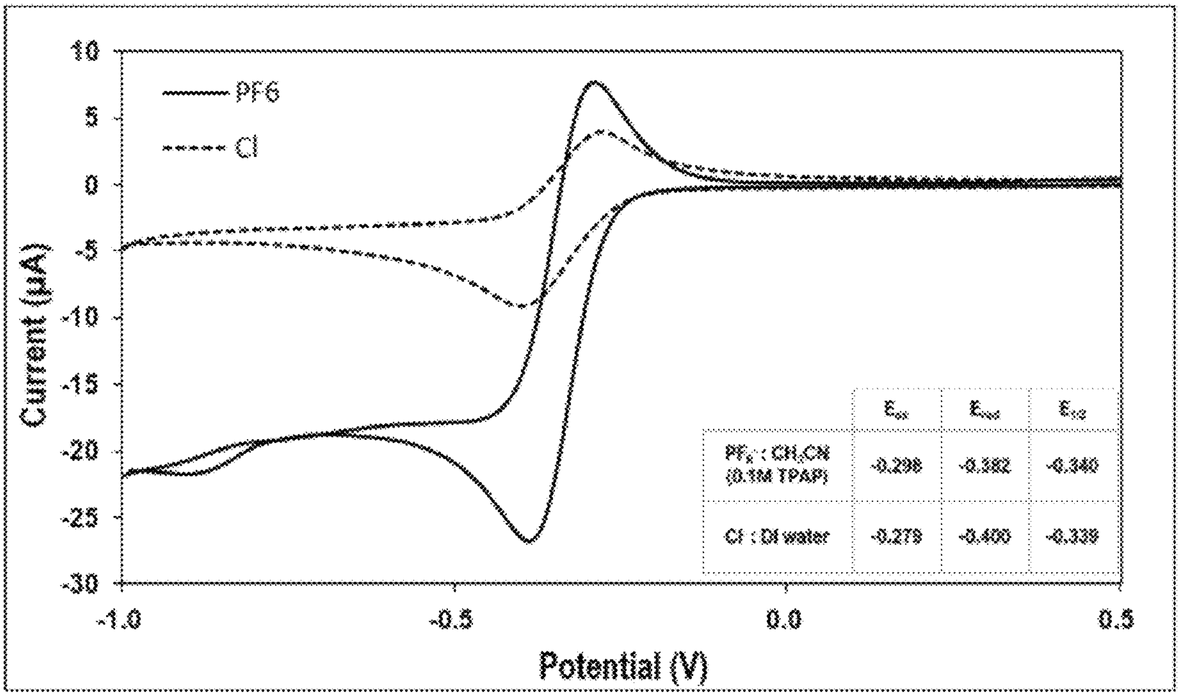

【FIG. 7a】
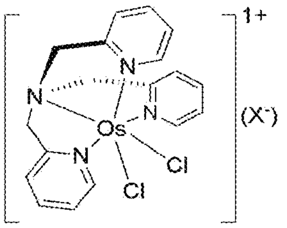
18
$E_{1/2}$ = -0.340 V ($PF_6^-$)
$E_{1/2}$ = -0.339 V ($Cl^-$)
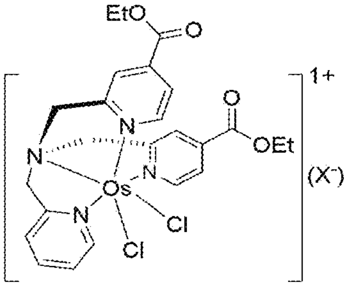
19
$E_{1/2}$ = -0.164 V ($PF_6^-$)
$E_{1/2}$ = -0.155 V ($Cl^-$)
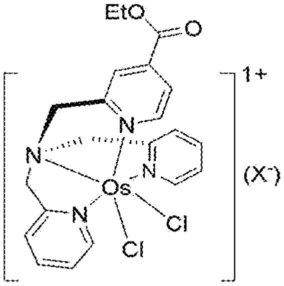
20
$E_{1/2}$ = -0.238 V ($PF_6^-$)
$E_{1/2}$ = -0.243 V ($Cl^-$)
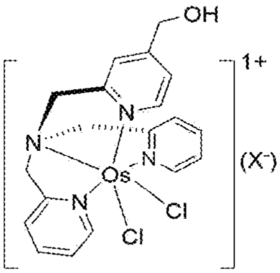
21
$E_{1/2}$ = -0.371 V ($PF_6^-$)
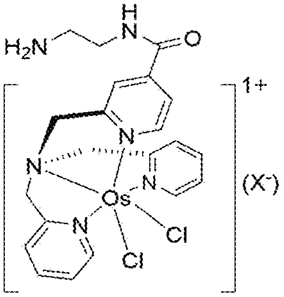
22
$E_{1/2}$ = -0.265 V ($PF_6^-$)
$E_{1/2}$ = -0.238 V ($Cl^-$)
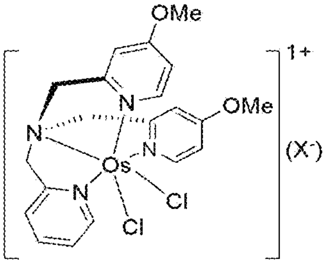
23
$E_{1/2}$ = -0.465 V ($PF_6^-$)
$E_{1/2}$ = -0.416 V ($Cl^-$)
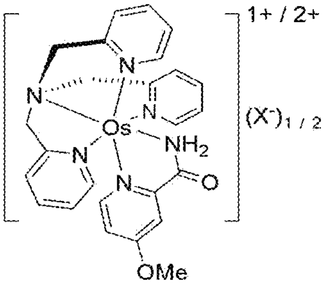
24
$E_{1/2}$ = +0.172, +0.401 V ($PF_6^-$)
$E_{1/2}$ = +0.021, +0.189 V ($Cl^-$)
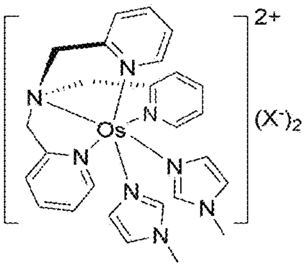
25
$E_{1/2}$ = +0.298 V ($PF_6^-$)
$E_{1/2}$ = +0.103 V ($Cl^-$)

【FIG. 7b】
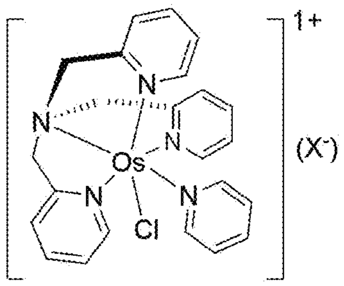
26
$E_{1/2}$ = +0.036 V ($Cl^-$)
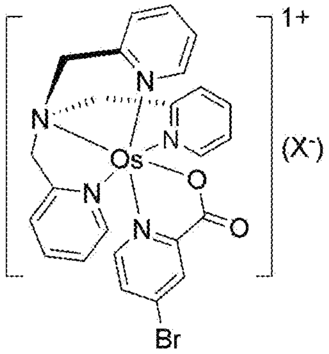
27
$E_{1/2}$ = +0.218 V ($PF_6^-$)
$E_{1/2}$ = +0.125 V ($Cl^-$)
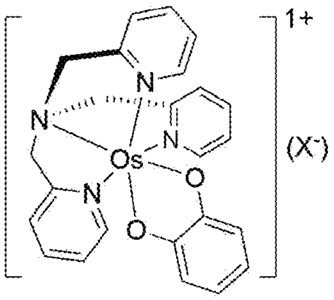
28
$E_{1/2}$ = -0.677 V, +0.286 ($PF_6^-$)
$E_{1/2}$ = -0.628 V, +0.250 ($Cl^-$)
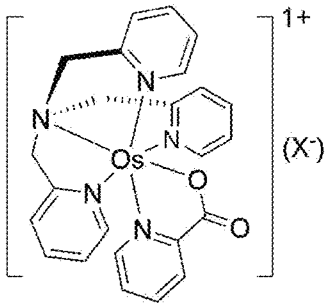
29
$E_{1/2}$ = +0.223 V ($PF_6^-$)
$E_{1/2}$ = +0.075 V ($Cl^-$)
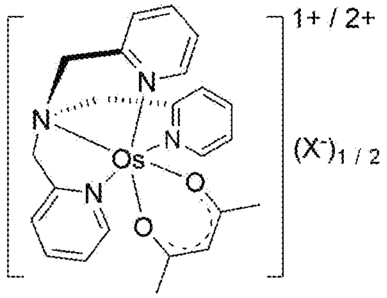
30
$E_{1/2}$ = -0.072 V ($PF_6^-$)
$E_{1/2}$ = -0.282 V ($Cl^-$)
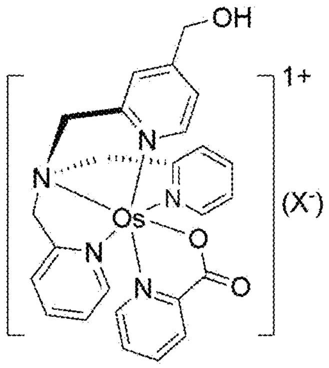
31
$E_{1/2}$ = +0.163 V ($PF_6^-$)
$E_{1/2}$ = +0.022 V ($Cl^-$)

【FIG. 7c】
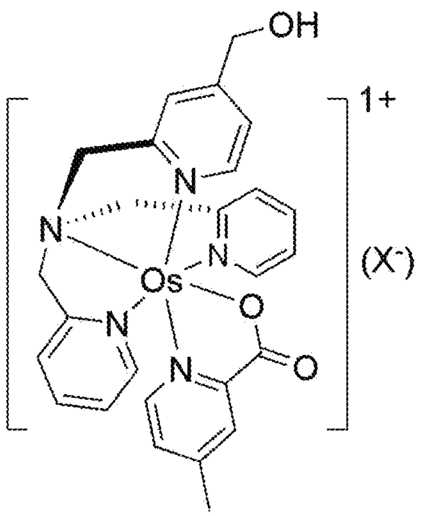
32
$E_{1/2}$ = +0.153 V ($PF_6^-$)
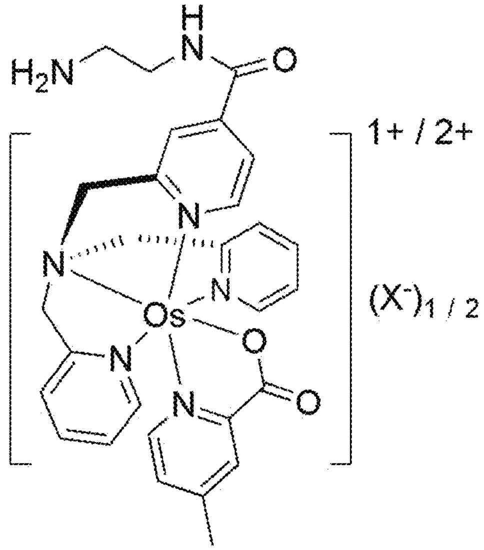
33
$E_{1/2}$ = +0.233 V ($PF_6^-$)
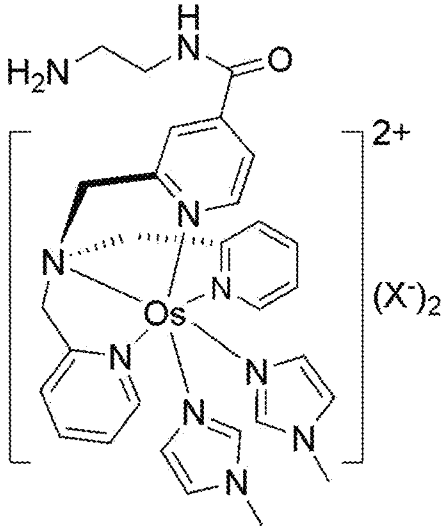
34
$E_{1/2}$ = +0.190 V ($Cl^-$)
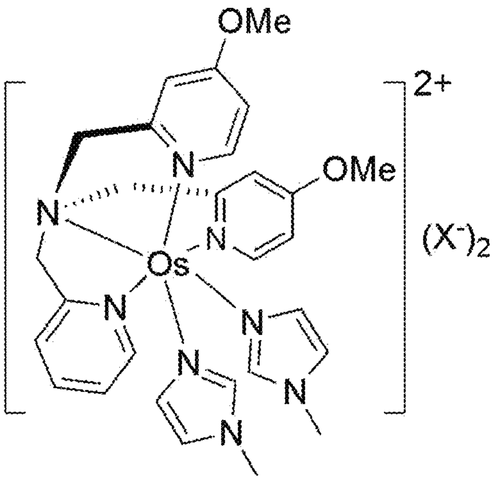
35
$E_{1/2}$ = +0.160 V ($PF_6^-$)
$E_{1/2}$ = -0.051 V ($Cl^-$)

【FIG. 8a】
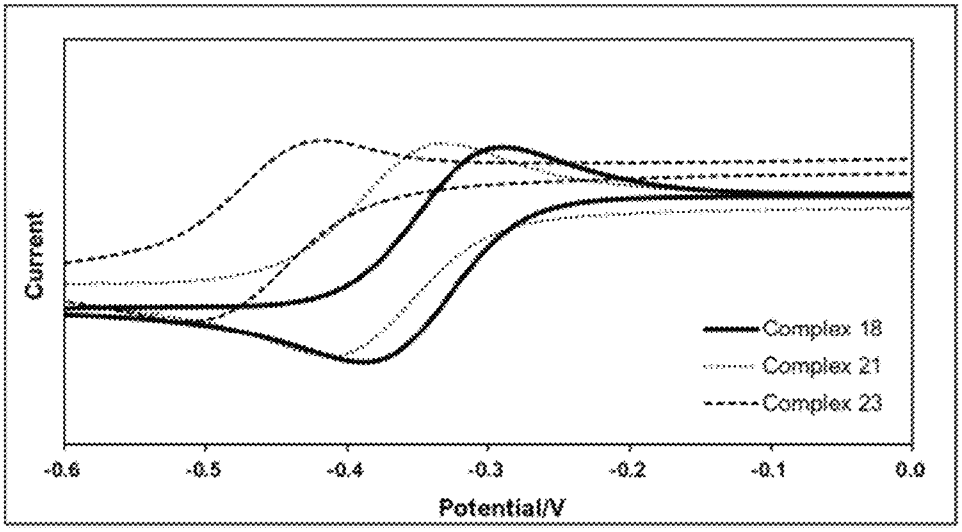
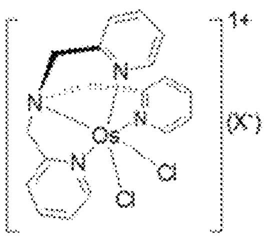
18
$E_{1/2}$ = -0.340 V ($PF_6^-$)
$E_{1/2}$ = -0.339 V ($Cl^-$)
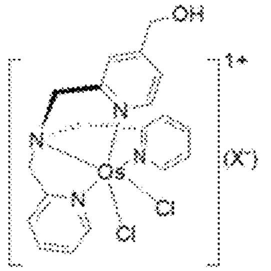
21
$E_{1/2}$ = -0.371 V ($PF_6^-$)
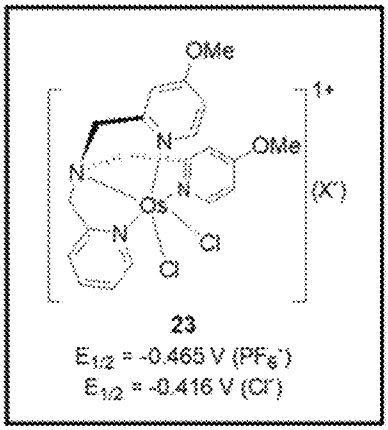
23
$E_{1/2}$ = -0.465 V ($PF_6^-$)
$E_{1/2}$ = -0.416 V ($Cl^-$)

【FIG. 8b】
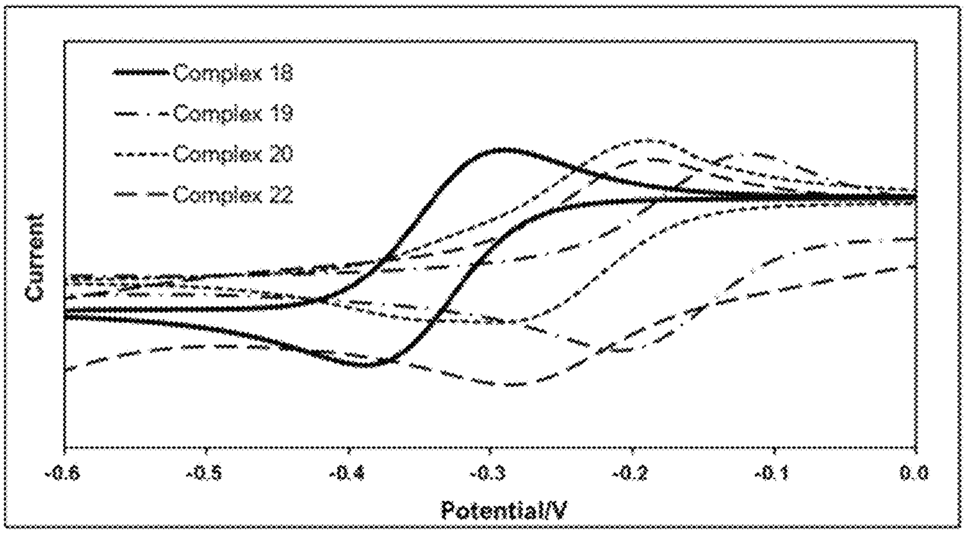
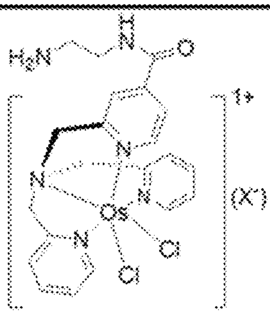
22
$E_{1/2}$ = -0.265 V ($PF_6^-$)
$E_{1/2}$ = -0.238 V ($Cl^-$)
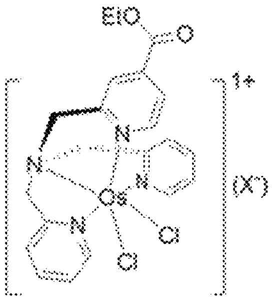
20
$E_{1/2}$ = -0.238 V ($PF_6^-$)
$E_{1/2}$ = -0.243 V ($Cl^-$)
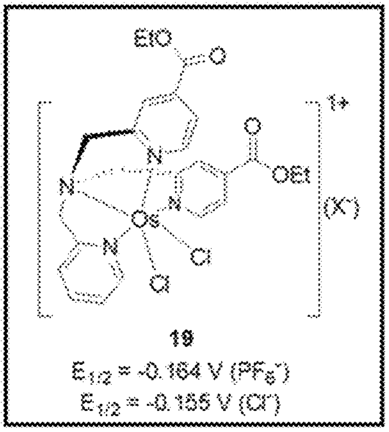
19
$E_{1/2}$ = -0.164 V ($PF_6^-$)
$E_{1/2}$ = -0.155 V ($Cl^-$)

【FIG. 9】
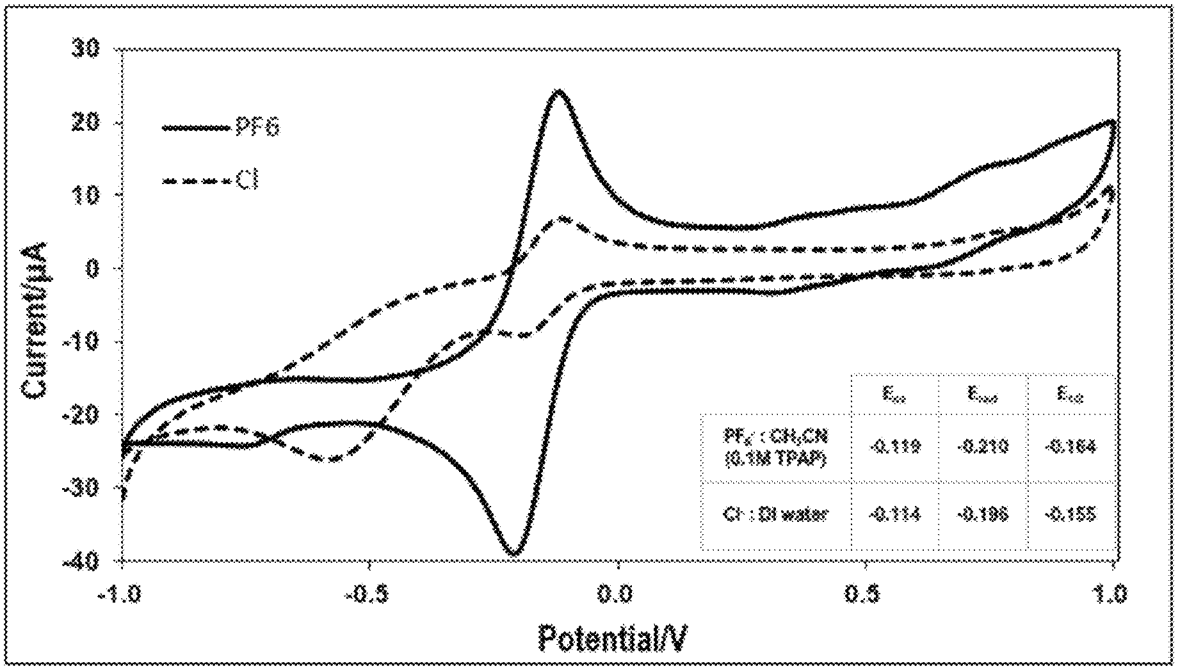

【FIG. 10】
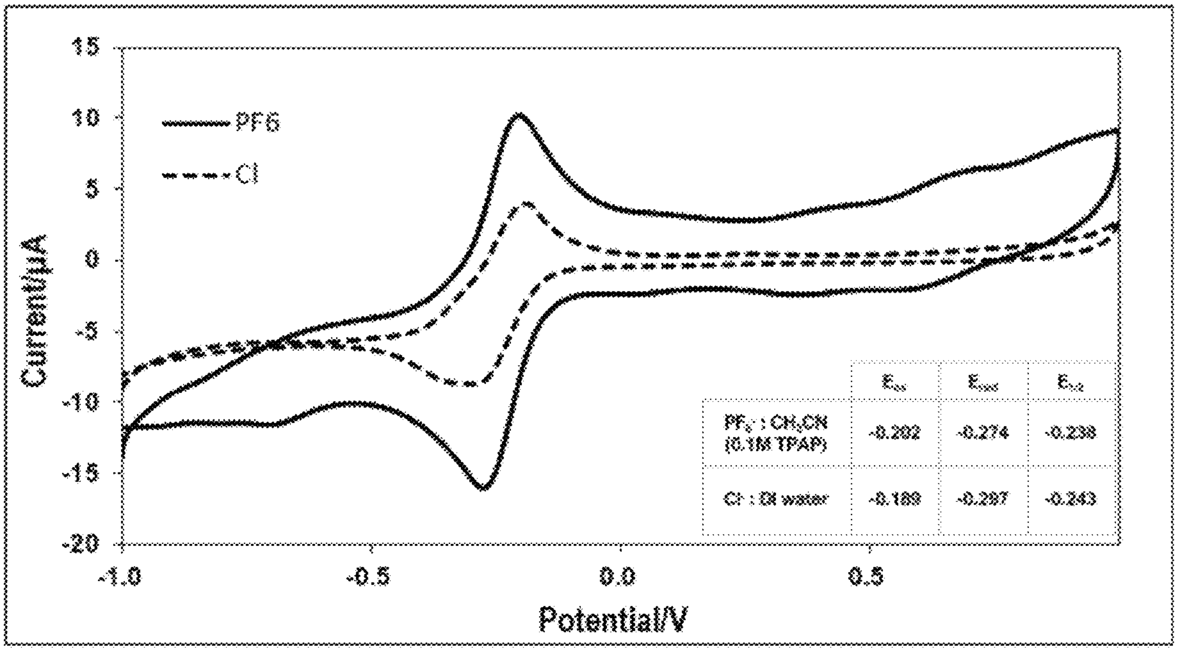
【FIG. 11】
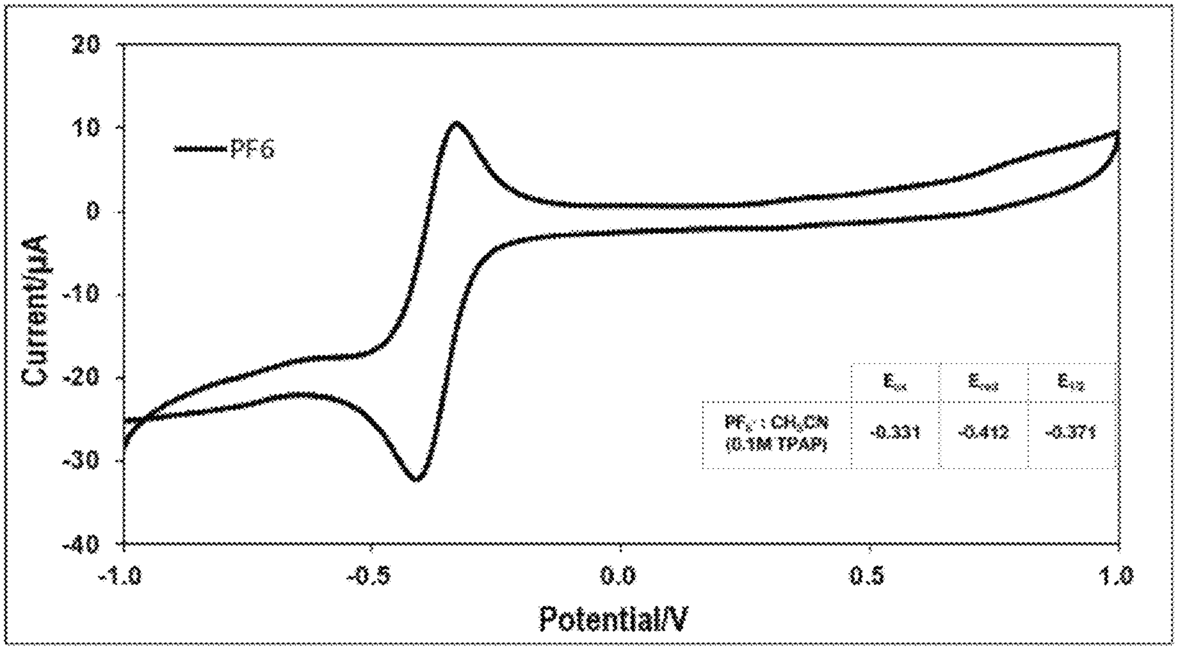

【FIG. 12】
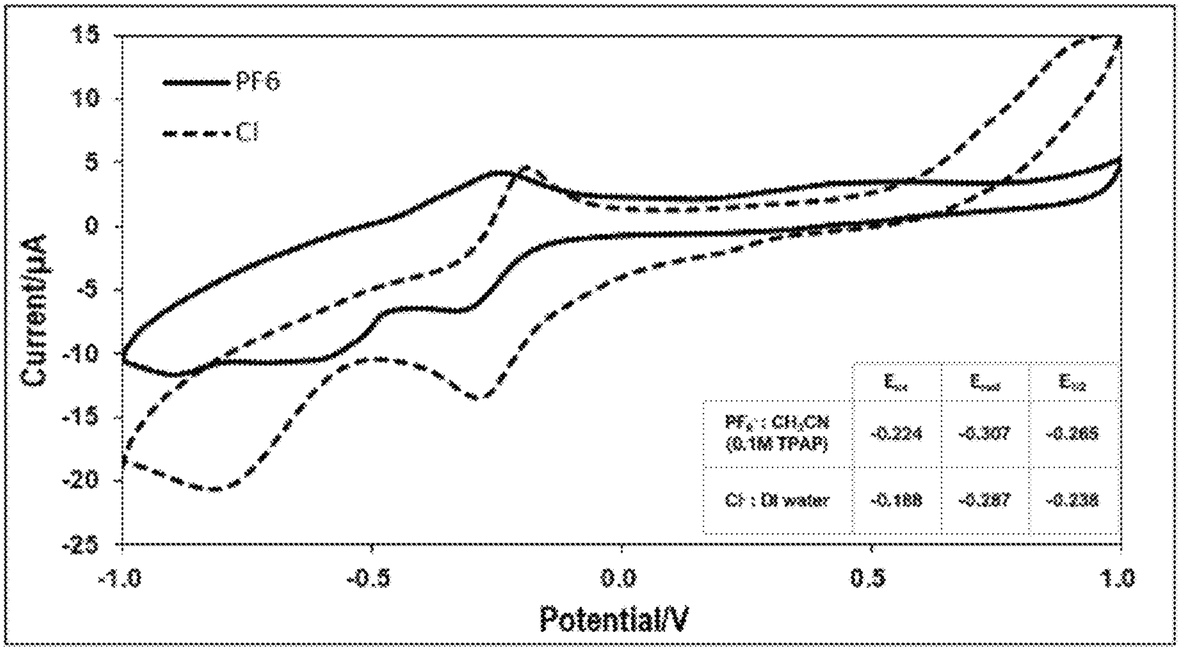
【FIG. 13】
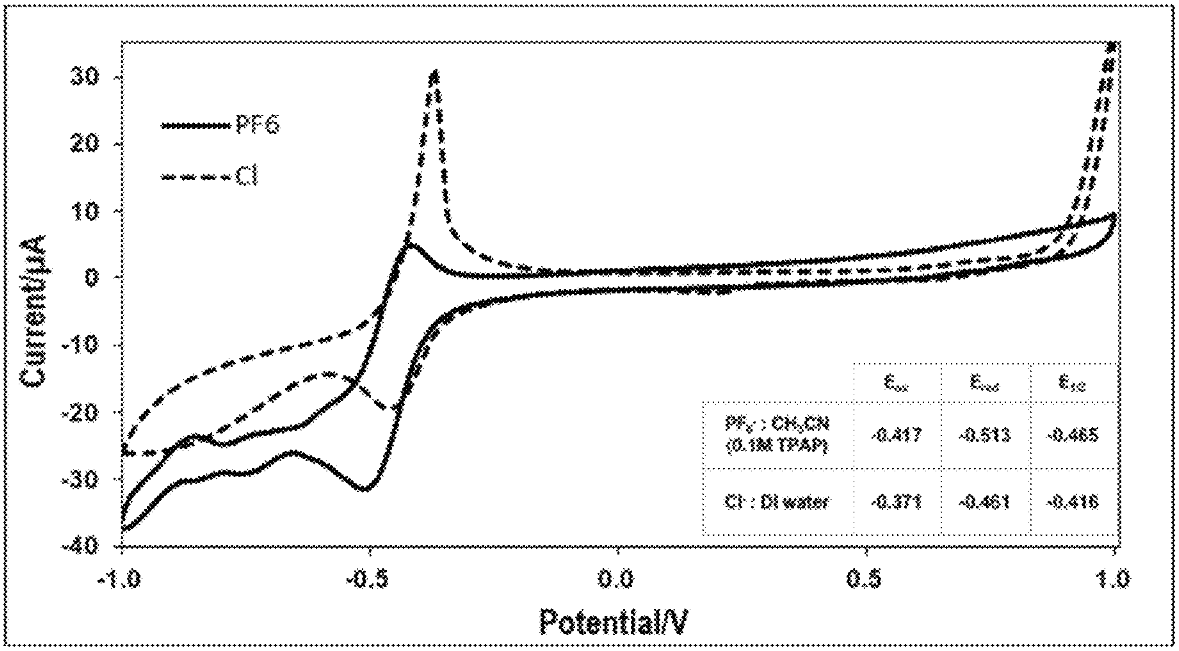

【FIG. 14】
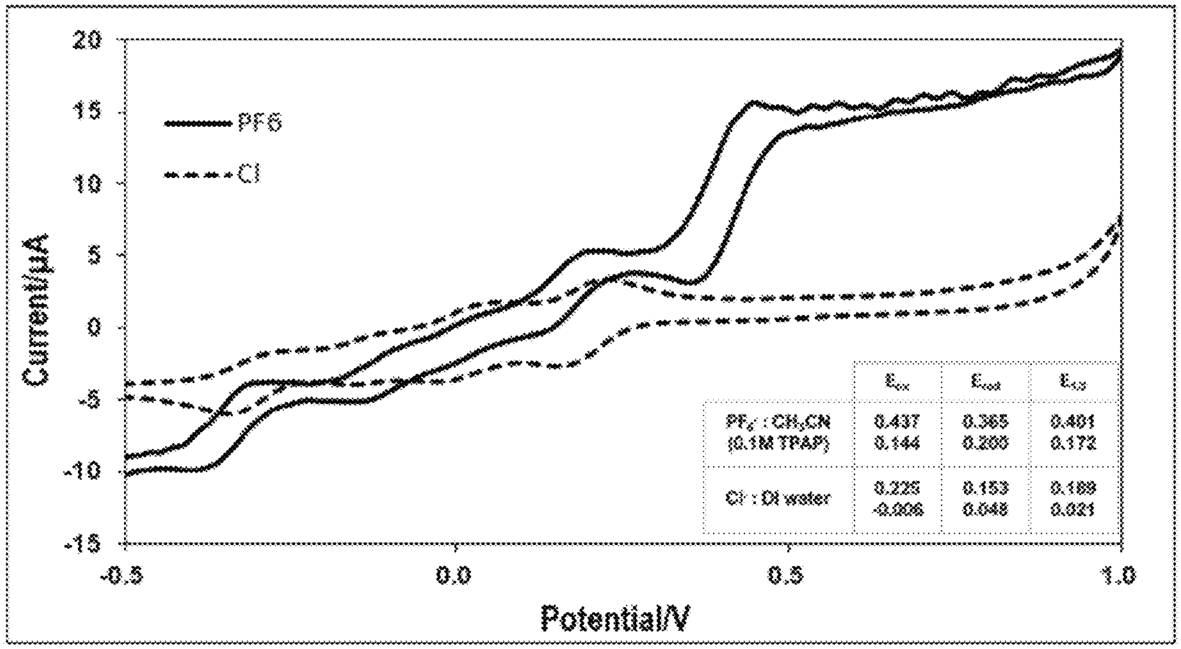
【FIG. 15】
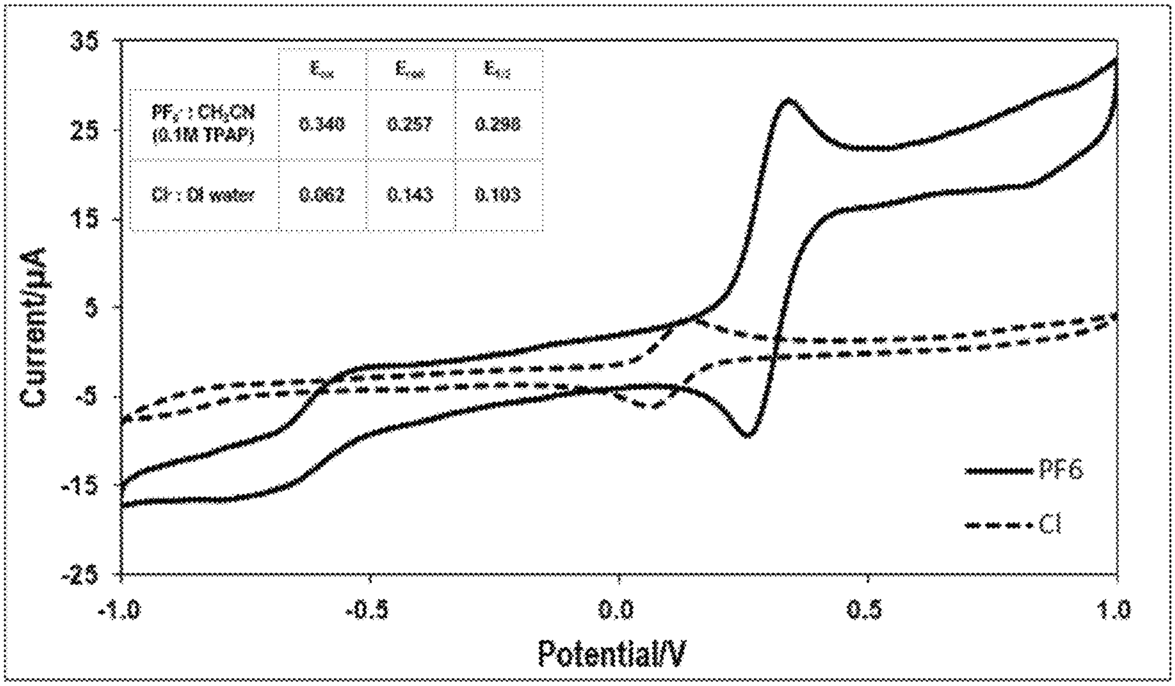

【FIG. 16】
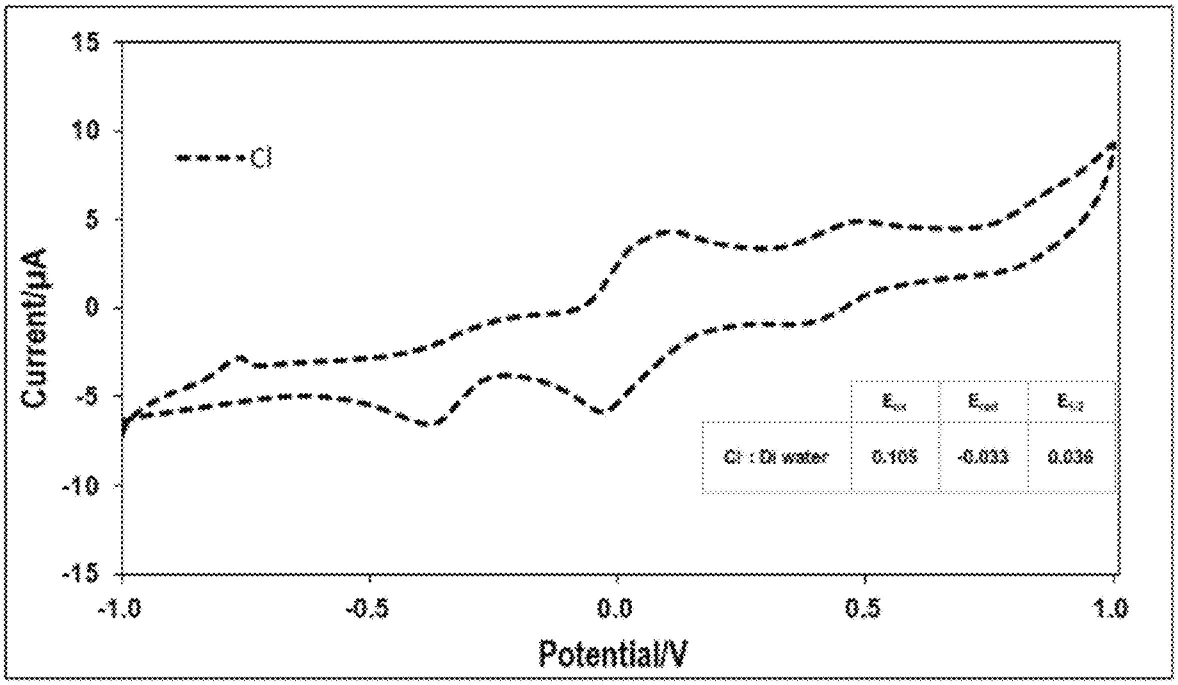
【FIG. 17】
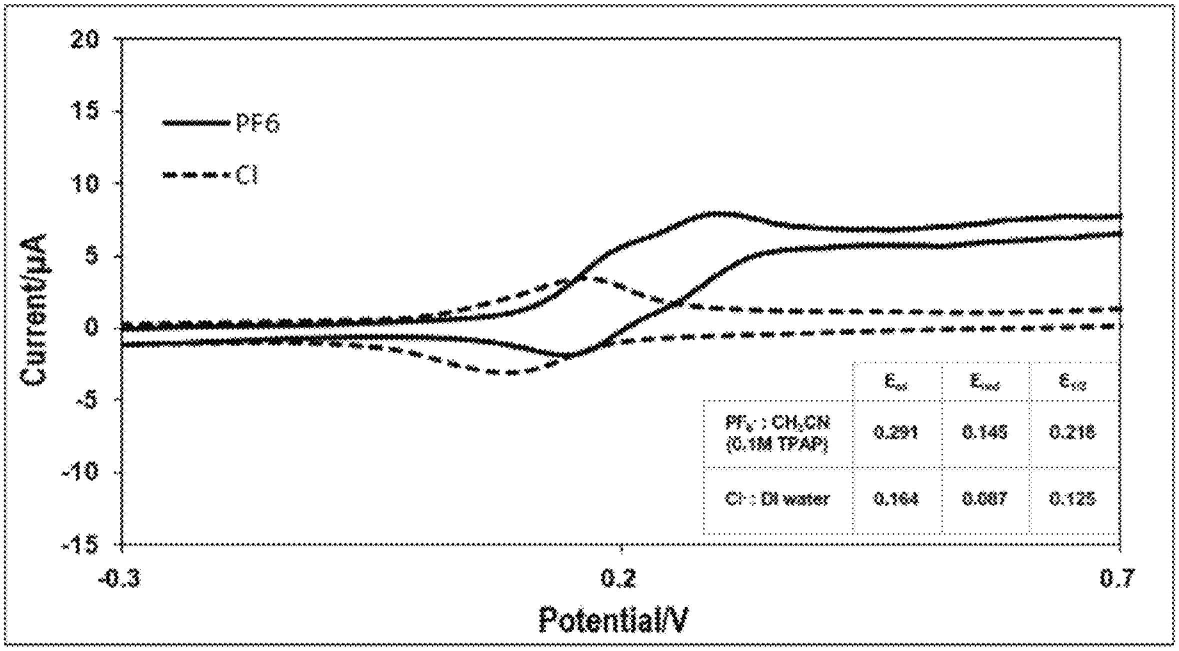

【FIG. 18】
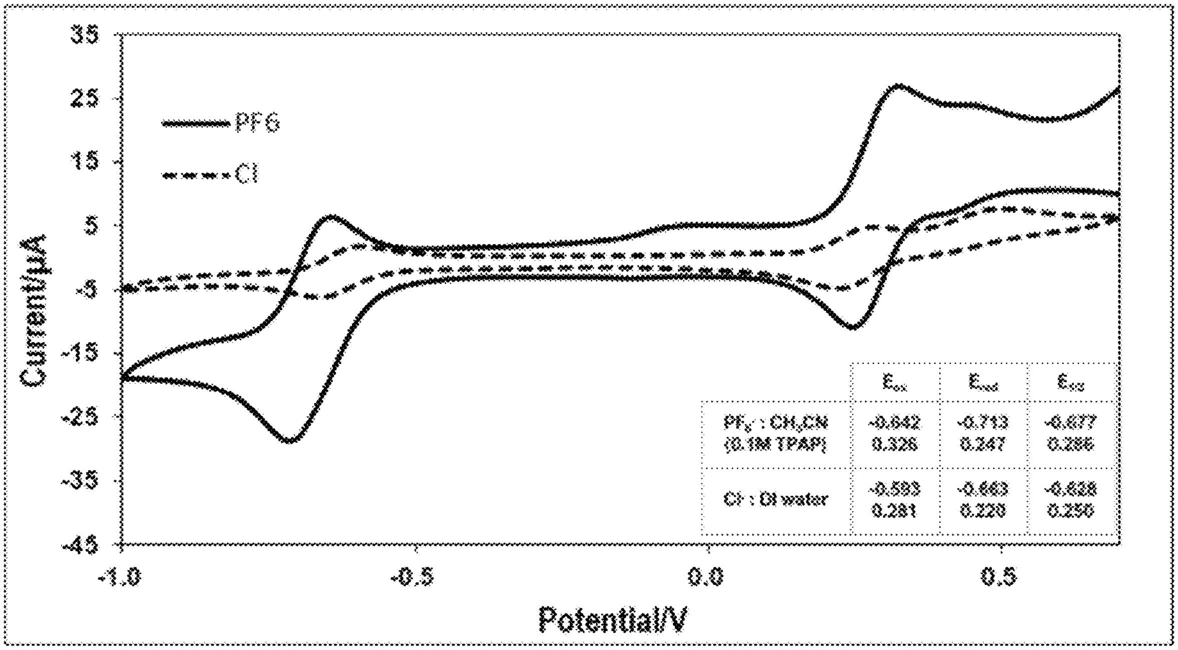
【FIG. 19】
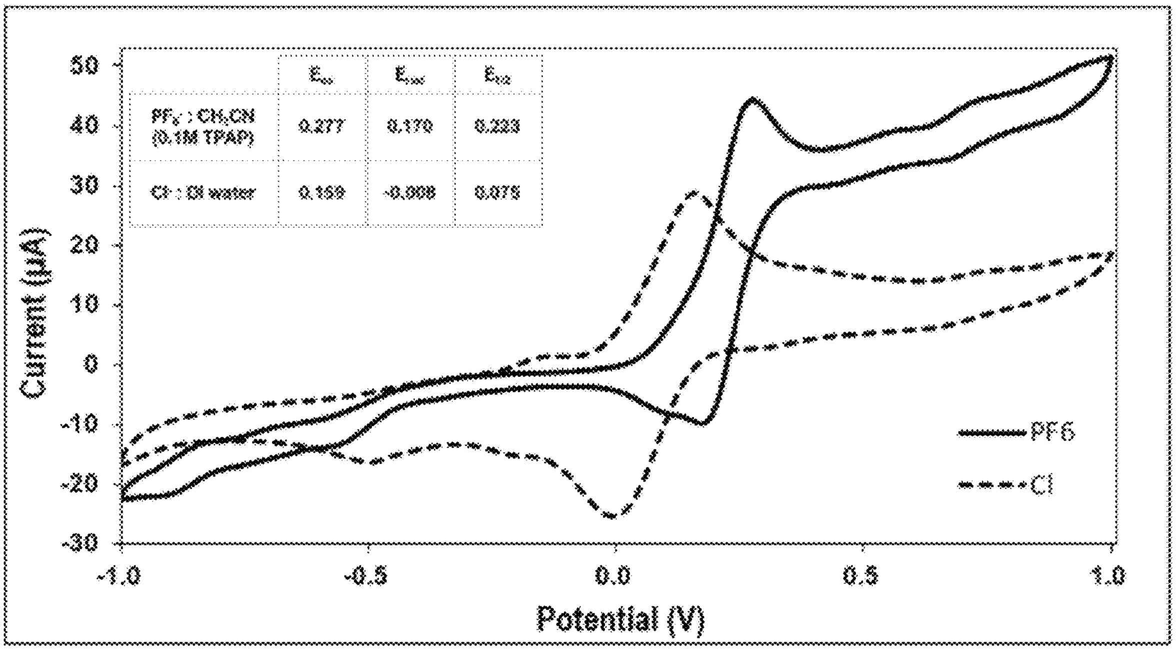

【FIG. 20】
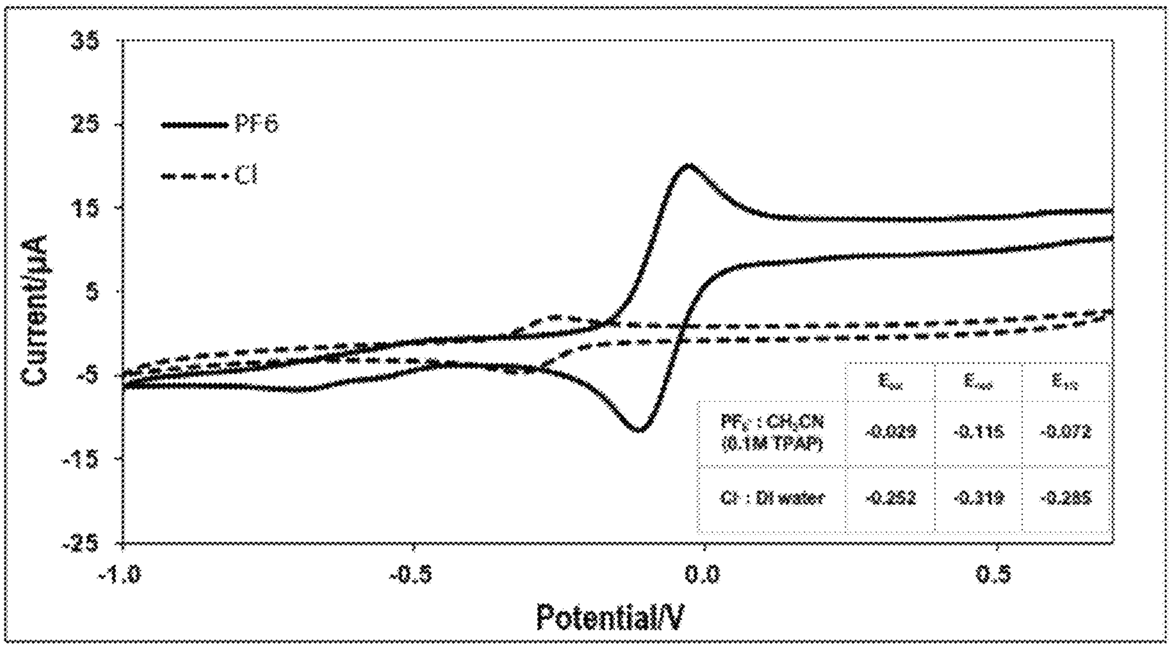
【FIG. 21】
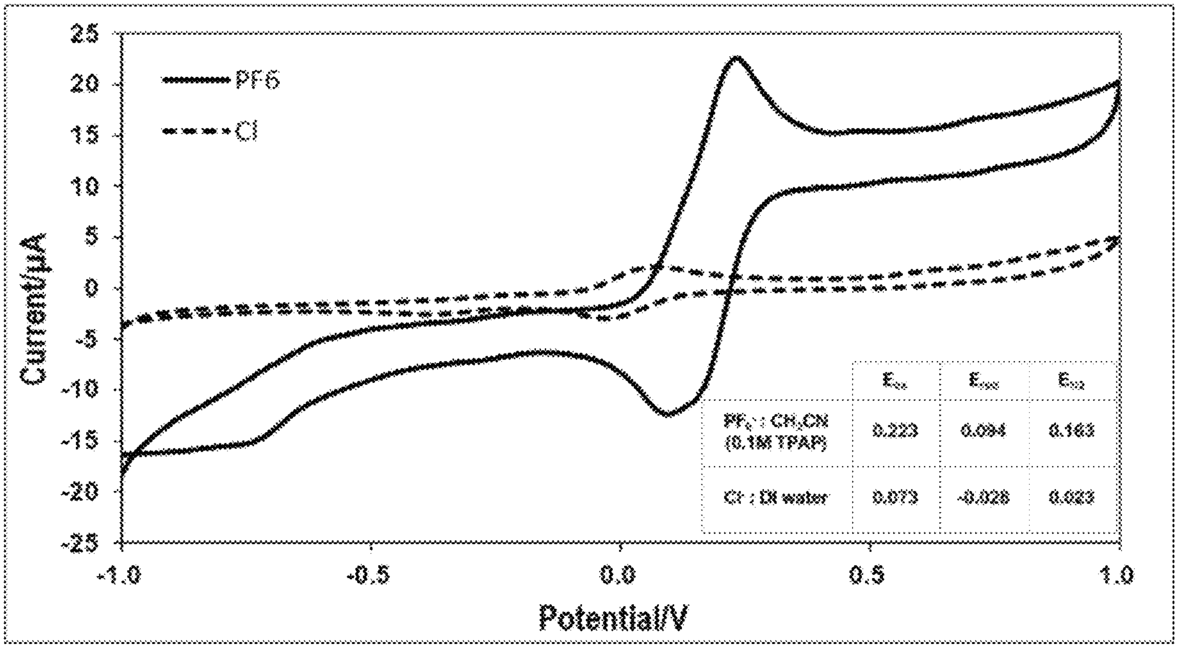

【FIG. 22】
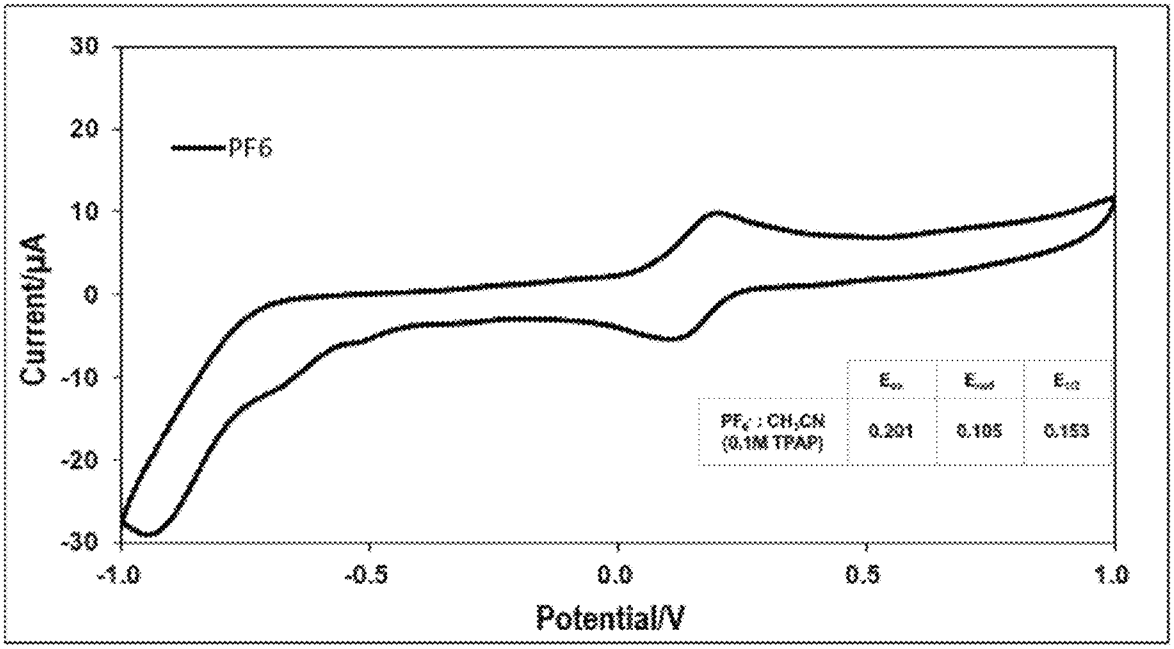
【FIG. 23】
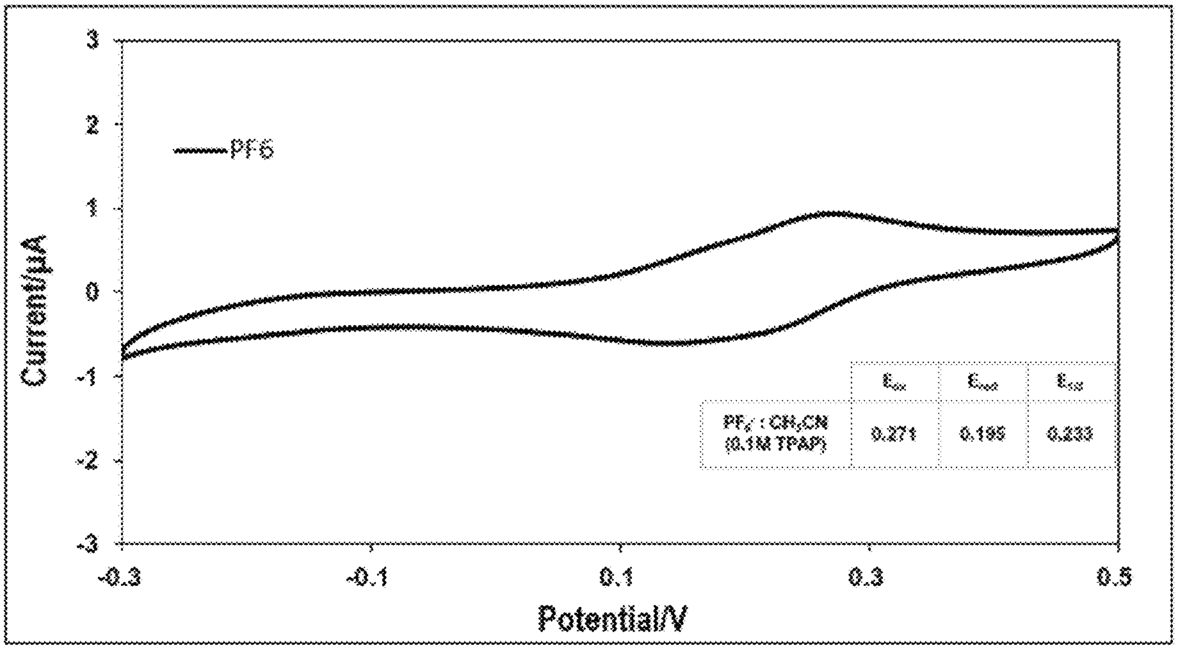

【FIG. 24】
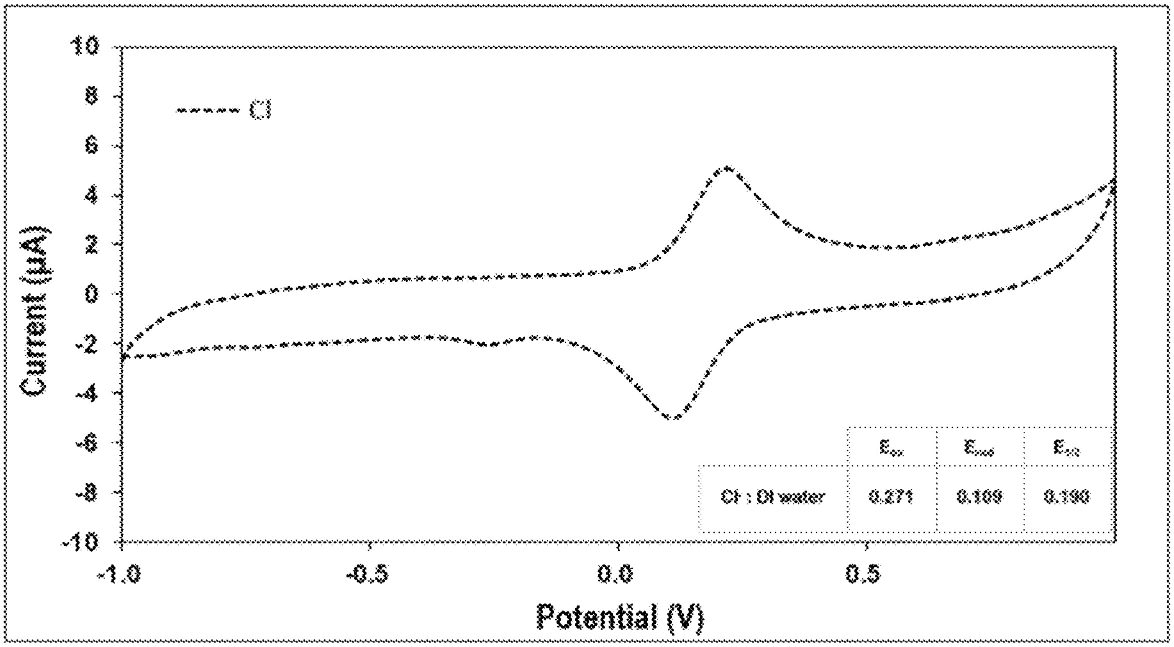
【FIG. 25】
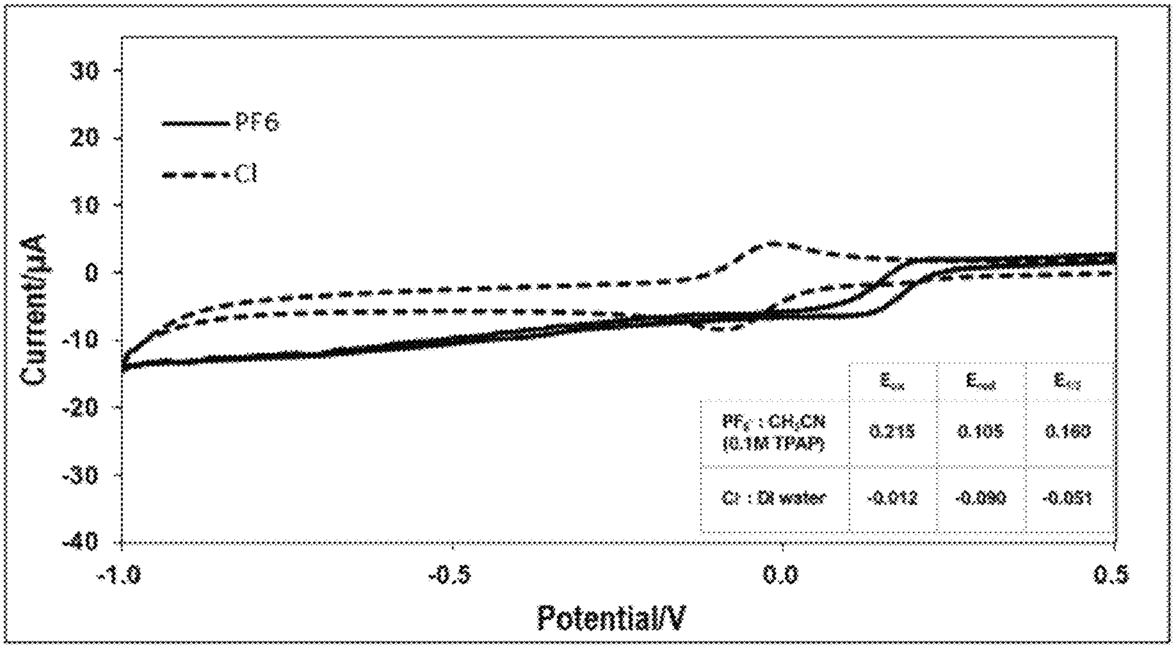

TRANSITION METAL COMPLEX CONTAINING TETRADENTATE NITROGEN DONOR LIGAND AND ELECTROCHEMICAL BIOSENSOR COMPRISING SAME

TECHNICAL FIELD

Cross-Reference to Related Application(S)

The present application claims the benefit of the priority based on Korean Patent Application No. 10-2020-0189139 filed on Dec. 31, 2020, and the entire contents disclosed in the document of the corresponding Korean patent application are incorporated as a part of the present description.

The present invention relates to a transition metal complex comprising a useful tetradentate nitrogen donor ligand as an electron transfer mediator and an electrochemical biosensor comprising the same.

BACKGROUND ART

Diabetes is disease that occurs when a high blood glucose level is maintained for a long time, and causes complications such as cardiovascular disease, stroke, kidney disease and the like. In response to the high blood glucose level, a process of reducing the blood glucose level by insulin injection, but if insulin is over-injected, hypoglycemia may occur, which may lead to shock or death. To prevent this, it is essential for diabetic patients to continuously measure the blood glucose concentration in the body using a blood glucose measuring sensor for the purpose of maintaining an appropriate blood glucose level.

Recently, a blood glucose sensor to which a Continuous Glucose Monitoring System (CGMS) is applied has been studied and commercialized considerably. The CGMS sensor is a device which is inserted into subcutaneous tissue and continuously measures the glucose concentration through intercellular fluid. In case of finger blood collecting method, it is difficult to confirm the exact change in the blood glucose level by blood glucose measurement 5~6 times a day, whereas the CGMS has an advantage of checking the change and tendency of the blood glucose level in a day. Through this, patients can quickly recognize hyperglycemia or hypoglycemia, and the ability to manage blood glucose can be further improved.

A biosensor refers to a device that selectively detects a biological sample and converts it into a specific signal. In particular, an enzyme-based biosensor using an electrochemical method is preferred because of its improved selectivity by the enzyme, as well as possible miniaturization and accuracy of measurement. The blood glucose biosensor using an electrochemical method is divided into first-generation and second-generation methods. The first-generation blood glucose sensor was first developed by Clark and Lyon, and is a method of measuring a blood glucose level through a change in the reduced oxygen concentration and concentration of generated hydrogen peroxide through an oxidation-reduction reaction of the enzyme, and the second-generation blood glucose sensor is a method of transferring electrons generated by an oxidation-reduction reaction of the enzyme to an electrode through an electron transfer mediator. The second-generation sensor has many advantages compared to the first-generation sensor in that there is less error depending on the oxygen concentration and the electron transfer reaction by a mediator is efficient and fast. For this reason, the second-generation sensor method comprising an electron transfer mediator is being applied to the CGMS blood glucose sensor.

An electrochemical enzyme-based blood glucose biosensor is generally composed of an enzyme, an electron transfer mediator, and an electrode. At first, glucose is oxidized to gluconolactone by the enzyme, and then the reduced enzyme is oxidized and donates electrons to the electron transfer mediator. Then, the reduced mediator passes through a process of transferring electrons to the electrode as it is oxidized. From this series of processes, the blood glucose level can be confirmed by an electrical signal.

Enzymes applied to the blood glucose sensor generally include glucose oxidase (GOx) and glucose dehydrogenase (GDH). GOx has been widely applied in the blood glucose sensor because it selectively oxidizes glucose and has a low cost and high stability. However, since GOx is greatly affected by oxygen in the oxidation process, it is known that the GOx-based blood glucose sensor has an error in measuring the blood glucose level higher than the actual level in a high altitude or low atmospheric pressure region. Unlike the GOx, GDH is characterized in that it can selectively oxidize glucose independently of oxygen concentration. In particular, GDH comprising FAD (flavin adenine dinucleotide) has a great advantage in being applied to the blood glucose sensor because it is not affected by oxygen and has excellent thermal stability. However, since a thick protein membrane surrounds the FAD active site, it is difficult for GDH to directly transfer electrons to the electrode surface. In order to solve this problem, the role of the electron transfer mediator, which facilitates the electron transfer reaction between the enzyme and electrode surface, is very important.

Electrochemical properties of the electron transfer mediator are key factors that can affect rapid electron transfer and selectivity and sensitivity in the blood glucose sensor. Interference of interfering substances in a living body can be avoided according to the potential of the mediator, and redox shuttling, a phenomenon in which the mediator generates an error current through repeated oxidation/reduction reactions between adjacent electrodes, can be thermodynamically avoided. Therefore, it is ideal that the electron transfer mediator has a reasonably low oxidation-reduction potential (−0.2V~OV vs Ag/AgCl) to perform an effective function. In addition, both oxidizing species and reducing species must be chemically stable and non-toxic in a body.

The electron transfer mediator that has been studied a lot so far includes ferrocene derivatives, ferricyanide, tetrathiafulvalene, transition metal complexes, and the like. Recently, complexes with iron, ruthenium and osmium as a central metal have been studied a lot as the electron transfer mediator, but there is still a need for a new electron transfer mediator which has high efficiency, is stable and has no toxicity in a body.

Under this background, the present inventors have repeated studies on a transition metal complex useful as an electron transfer mediator for an electrochemical biosensor, and as a result, they have confirmed that when tris-2-pyridylmethylamine (tris(2-pyridylmethyl)amine, TPMA) is introduced as a tetradentate ligand, it exhibits exceptionally high stability compared to conventional monodentate or bidentate ligands, and a transition metal complex prepared therefrom can be easily synthesized and shows stable electrochemical properties, thereby completing the present invention.

DISCLOSURE

Technical Problem

An object of the present invention is to provide a novel transition metal complex for an electron transfer mediator comprising a tetradentate nitrogen donor ligand.

Another object of the present invention is to provide an electrochemical biosensor comprising a redox polymer comprising the transition metal complex.

Other object of the present invention is to provide a method for preparation of the transition metal complex.

Technical Solution

According to one aspect of the present invention, a transition metal complex comprising a tetradentate nitrogen donor ligand, useful as an electron transfer mediator can be provided.

According to one aspect of the present invention, a method for preparing the transition metal complex can be provided.

According to one aspect of the present invention, a device comprising the transition metal complex as an electron transfer mediator can be provided.

According to one aspect of the present invention, a sensing layer for an electrochemical biosensor comprising an enzyme capable of redoxing a liquid biological sample; and the transition metal complex as an electron transfer mediator can be provided.

Advantageous Effects

The transition metal complex comprising a tetradentate nitrogen donor ligand according to the present invention excellently improves the performance of an electrochemical sensor when used for an electrochemical sensor.

BRIEF DESCRIPTION OF THE DRAWINGS

FIG. 1 is a drawing which discloses various synthesis methods to prepare tetradentate ligands for preparing the transition metal complex of the present invention.

FIG. 2 is a reaction formula showing the synthesis method of the $[Os(TPMA)Cl_2]^+(PF_6^-)$ complex and various derivatives which can be synthesized therefrom.

FIG. 3 is a drawing which shows the crystal structure of $[Os(TPMA)Cl_2]^+(PF_6^-)$.

FIG. 4 is a reaction formula showing the synthesis method of the $[Os(TPMA)(L)_{1\sim2}]^{n+}(PF_6^-)_n$ complex and various derivatives which can be synthesized therefrom.

FIG. 5 is a drawing which shows the change in the mass signal confirmed on ESI-MS of the hydroxymethyl TPMA osmium complex.

FIG. 6 is a graph showing CV data of $[Os(TPMA)Cl_2]^+(X^-)$(18). FIGS. 7*a* to 7*c* are drawings which show the structures and oxidation/reduction potentials of the osmium complexes based on TPMA.

FIGS. 8*a* and 8*b* are graphs comparing the potential values by cyclic voltammetry of the $[Os(TPMA)Cl_2]^+(PF_6^-)$ complexes depending on the substituent. FIG. 8*a* is a graph comparing to the complexes with EDG (18, 21, 23), and FIG. 8*b* is a graph comparing to the complexes with EWG (18, 19, 20, 22). In order to compare the potential values of the complexes regardless of the concentration, the current value was corrected to 18, and measured by injection at 10 mV/s in 0.1 M TPMP in $CH_3CN$ solution.

FIG. 9 is a graph showing CV data of the $[Os(TPMA)Cl_2]^+(PF_6^-)$ Complex (19).

FIG. 10 is a graph showing CV data of the $[Os(TPMA)Cl_2]^+(PF_6^-)$ Complex (20).

FIG. 11 is a graph showing CV data of the $[Os(TPMA)Cl_2]^+(PF_6^-)$ Complex (21).

FIG. 12 is a graph showing CV data of the $[Os(TPMA)Cl_2]^+(PF_6^-)$ Complex (22).

FIG. 13 is a graph showing CV data of the $[Os(TPMA)Cl_2]^+(PF_6^-)$ Complex (23).

FIG. 14 is a graph showing CV data of the $[Os(TPMA)(L)_{1\sim2}]^{n+}(PF_6^-)_n$ Complex (24).

FIG. 15 is a graph showing CV data of the $[Os(TPMA)(L)_{1\sim2}]^{n+}(PF_6^-)_n$ Complex (25).

FIG. 16 is a graph showing CV data of the $[Os(TPMA)(L)_{1\sim2}]^{n+}(PF_6^-)_n$ Complex (26).

FIG. 17 is a graph showing CV data of the $[Os(TPMA)(L)_{1\sim2}]^{n+}(PF_6^-)_n$ Complex (27).

FIG. 18 is a graph showing CV data of the $[Os(TPMA)(L)_{1\sim2}]^{n+}(PF_6^-)_n$ Complex (28).

FIG. 19 is a graph showing CV data of the $[Os(TPMA)(L)_{1\sim2}]^{n+}(PF_6^-)_n$ Complex (29).

FIG. 20 is a graph showing CV data of the $[Os(TPMA)(L)_{1\sim2}]^{n+}(PF_6^-)_n$ Complex (30).

FIG. 21 is a graph showing CV data of the $[Os(TPMA)(L)_{1\sim2}]^{n+}(PF_6^-)_n$ Complex (31).

FIG. 22 is a graph showing CV data of the $[Os(TPMA)(L)_{1\sim2}]^{n+}(PF_6^-)_n$ Complex (32).

FIG. 23 is a graph showing CV data of the $[Os(TPMA)(L)_{1\sim2}]^{n+}(PF_6^-)_n$ Complex (33).

FIG. 24 is a graph showing CV data of the $[Os(TPMA)(L)_{1\sim2}]^{n+}(PF_6^-)_n$ Complex (34).

FIG. 25 is a graph showing CV data of the $[Os(TPMA)(L)_{1\sim2}]^{n+}(PF_6^-)_n$ Complex (35).

BEST MODE

As one aspect, the present invention provides a transition metal complex comprising a tetradentate nitrogen donor ligand useful as an electron transfer mediator.

As one embodiment, the transition metal complex may be represented by Chemical formula 1 or 2 below.

[Chemical formula 1]

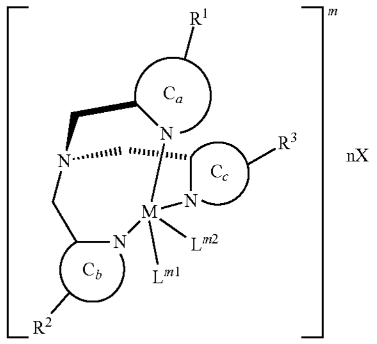

-continued

[Chemical formula 2]

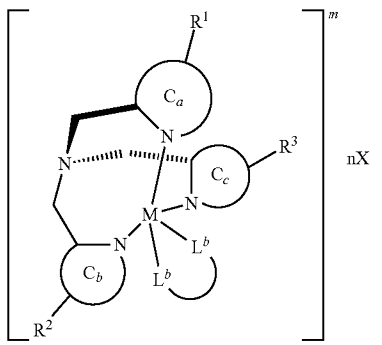

In the Chemical formula 1 or Chemical formula 2, M may be one selected from the group consisting of Fe, Co, Ru, Os, Rh and Ir; and $C_a$, $C_b$, $C_c$ are heterocyclic compounds comprising one or more nitrogen atoms, and are preferably linked to an amine group and a methylene group at the position 2 of the cyclic compound; and $L^{m1}$ and $L^{m2}$ are monodentate ligands coordinated each independently; and $L^b$ is a bidentate ligand comprising nitrogen or oxygen; and m is a negative charge or positive charge showing −1~−5 or 1~5; and $R^1$, $R^2$ and $R^3$ are each independently a structure composed of a linker into which a reactive group capable of linking to a polymer is introduced; and X is a counter ion; and n means the number of counter ions, and is 1~5.

As one embodiment, the transition metal complex may comprise a tetradentate ligand represented by Chemical formula 3 below.

[Chemical formula 3]

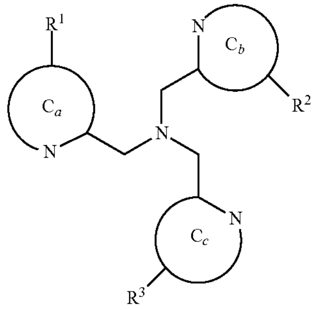

In the formula, $C_a$, $C_b$ and $C_c$ are each independently a heterocyclic compound comprising one or more nitrogen atoms; and $R^1$, $R^2$ and $R^3$ are each independently a linker into which a reactive group capable of linking to a polymer is introduced, or an electron donating group (EDG) or electron withdrawing group (EWG) for controlling an oxidation/reduction potential.

In one example, the tetradentate ligand of Chemical formula 3 above may be one of ligands having the following structures:

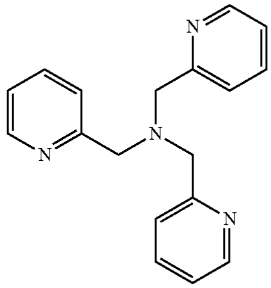
,

10

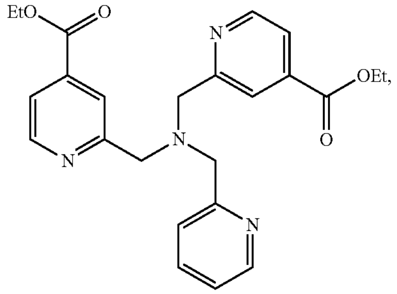

11

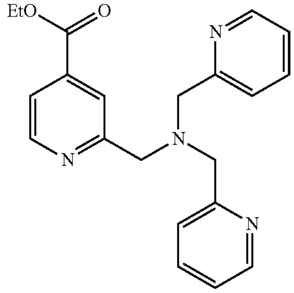
,

12

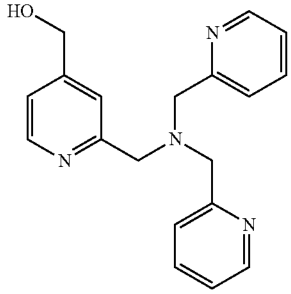
,

13

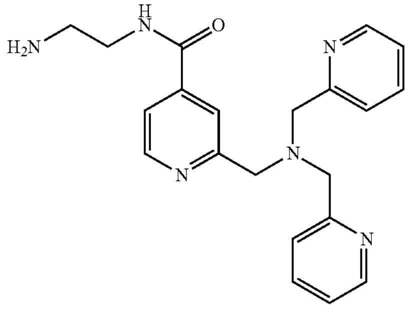
,

14

-continued

15

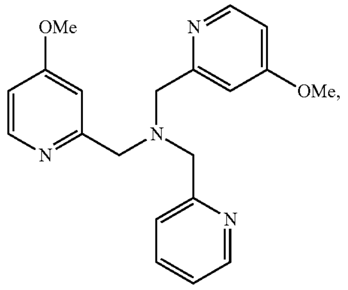

16

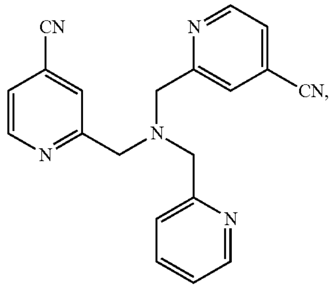

and

17

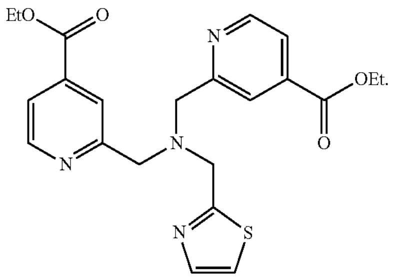

Preferably, the heterocyclic compound may be linked to an amine group and a methylene group at position 2, and three nitrogens of the three hetero rings and one nitrogen at the center connecting the three hetero rings to each other may be connected to the transition metal M.

Specifically, the $R_1$, $R_2$ and $R_3$ of Chemical formulas 1 to 3 above may be each independently —H; —F; —Cl; —Br; —I; —$NO_2$; —CN; —$CO_2H$; —$SO_3H$; —$NHNH_2$; —SH; —OH; —$NH_2$; —$CH_2OH$; —$CONHCH_2CH_2NH_2$; or substituted or unsubstituted alkoxycarbonyl, alkylaminocarbonyl, dialkylaminocarbonyl, alkoxy, alkylamino, dialkylamino, alkanylamino, arylcarboxyamido, hydrazino, alkylhydrazino, hydroxyamino, alkoxyamino, alkylthio, alkenyl, aryl or alkyl.

Specifically, the $L^{m1}$ and $L^{m2}$ are monodentate ligands, and may be each independently —H, —F, —Cl, —Br, —I, —$NO_2$, —$NCCH_3$, —CO, —$OH_2$, —$NH_3$ or a heterocyclic compound comprising one or more nitrogen atoms.

Specifically, the Ire $L^b$-$L^b$ may be catechol, acetylacetone, 2-picolinic acid, 2-pyridinecarboxamide, 2,2-bipyridine or 2,2-bithiazole.

As one specific aspect, the heterocyclic compound may be one or more kinds selected from the group consisting of imidazole, pyridine, pyrimidine, pyrazole, isoxazole, oxazole, thiazole, benzothiazole, benzimidazole, benzoxazole and diazafluorenone.

As one specific aspect, when the alkoxycarbonyl, alkylaminocarbonyl, dialkylaminocarbonyl, alkoxy, alkylamino, dialkylamino, alkanylamino, arylcarboxyamido, hydrazino, alkylhydrazino, hydroxyamino, alkoxyamino, alkylthio, alkenyl, aryl, alkyl and 3-ring heterocyclic ring are substituted, they may be substituted with one or more, preferably, 1 to 3 selected from the group consisting of —F, —Cl, 13 Br, —I, —OH, oxo, alkyl groups having 1 to 3 carbon atoms and alkoxy groups having 1 to 3 carbon atoms.

As one specific aspect, the transition metal complex of Chemical formula 1 or 2 according to the present invention may be one of the transition metal complexes shown in Table 1 below:

TABLE 1

| Complex number | Chemical structure of transition metal complexes |
|---|---|
| 18 | 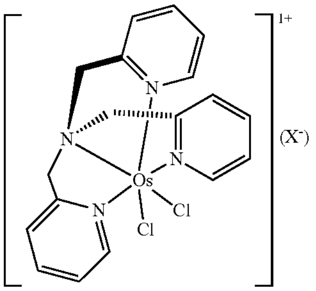 |
| 19 | 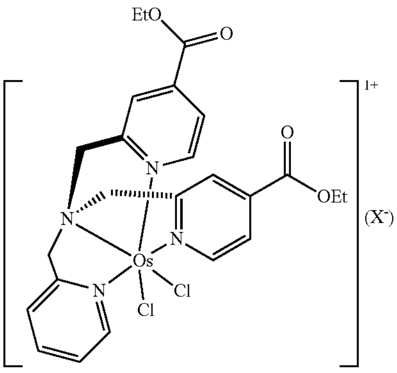 |
| 20 | 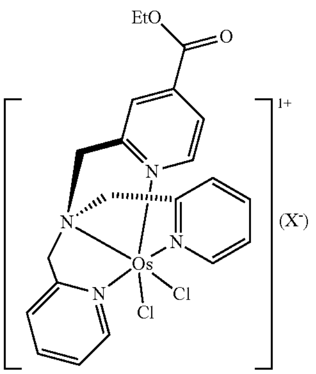 |

TABLE 1-continued
| Complex number | Chemical structure of transition metal complexes |
|---|---|
| 21 | 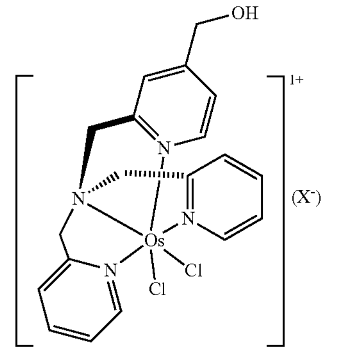 |
| 22 | 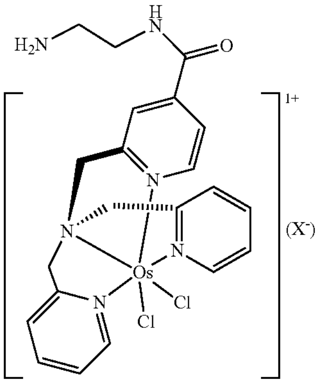 |
| 23 | 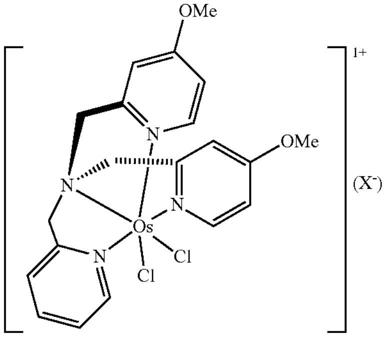 |
| 24 | 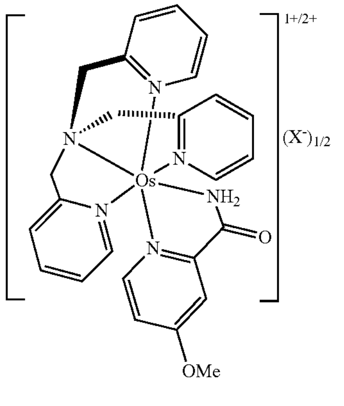 |
TABLE 1-continued
| Complex number | Chemical structure of transition metal complexes |
|---|---|
| 25 | 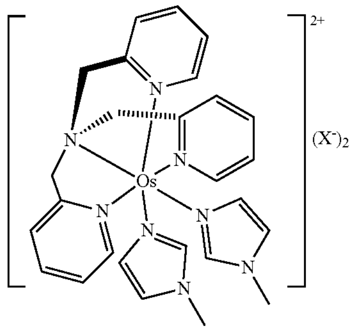 |
| 26 | 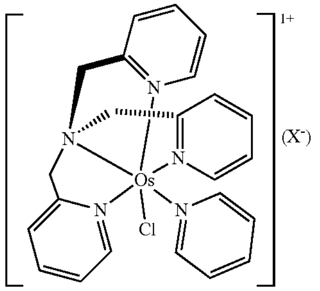 |
| 27 | 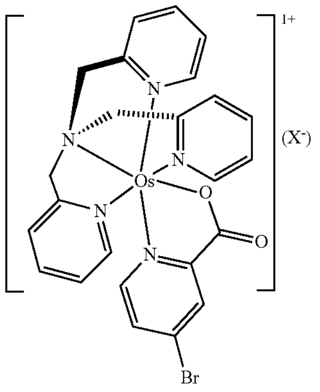 |
| 28 | 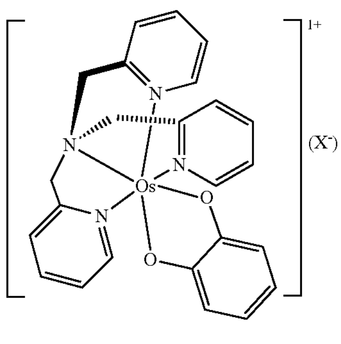 |

TABLE 1-continued

| Complex number | Chemical structure of transition metal complexes |
| --- | --- |
| 29 | 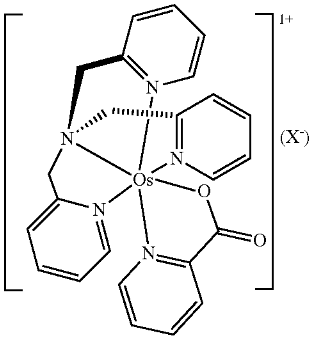 |
| 30 | 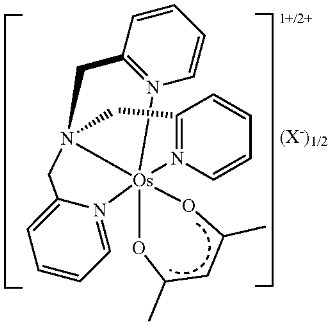 |
| 31 | 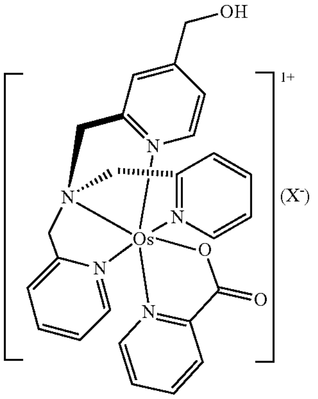 |
| 32 | 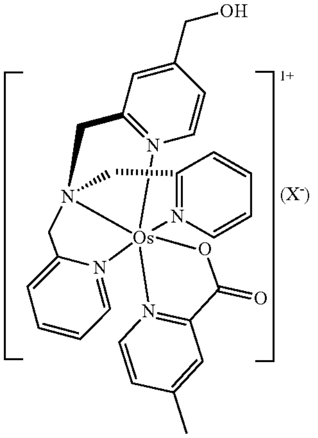 |
| 33 | 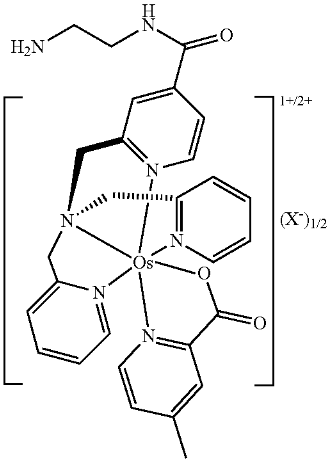 |
| 34 | 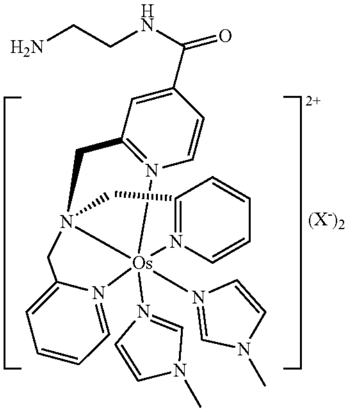 |
| 35 | 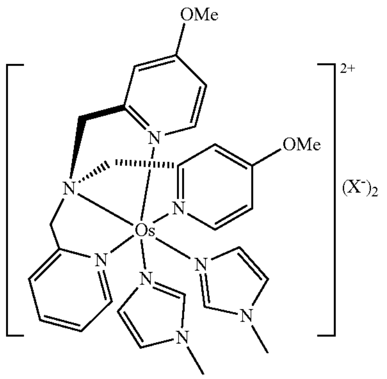 |

As another aspect, the present invention provides a method for preparation of the transition metal complex useful as an electron transfer mediator.

The transition metal complex useful as an electron transfer mediator according to the present invention may be prepared by a salt, preferably, osmium salt, of the transition metal. In one specific embodiment, the salt of the transition metal may be an ammonium salt of the halogenated transition metal of Chemical formula 4 below, $[(NH_4)_2MX_6]$ [Chemical formula 4]

In the formula,

M may be one selected from the group consisting of Fe, Co, Ru, Os, Rh and Ir; and X is F, Cl, Br, or I.

Preferably, the ammonium salt of the halogenated transition metal of Chemical formula 4 may be ammonium hexachloroosmate of Chemical formula 5, and this is commercially available.

$[(NH_4)_2O_sCL_6]$ [Chemical formula 5]

In one example, the method for preparation of the transition metal complex according to the present invention may synthesize it using a tris-pyridinemethylamine-based ligand and an ammonium salt of the halogenated transition metal. As a specific embodiment, in case of the complex comprising osmium, it may comprise the following steps:

a) introducing a tetradentate tris-pyridinemethylamine-based ligand represented by Chemical formula 3 into an ammonium salt of halogenated osmium of Chemical formula 5, to synthesize an osmium complex of Chemical formula 6; and b) introducing one kind or 2 kinds of monodentate ligands or bidentate ligands selected from the group consisting of N—N ligands, N-ligands, N—O ligands and O—O ligands into the osmium complex of Chemical formula 6.

As one embodiment, the transition metal complex may comprise a tetradentate ligand represented by Chemical formula 3 below.

[Chemical formula 3]

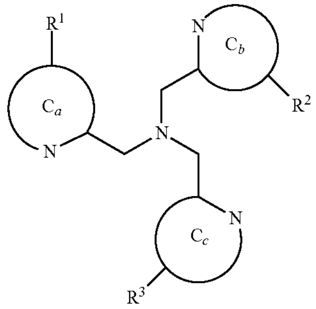

In the formula, $C_a$, $C_b$ and $C_c$ are each independently a heterocyclic compound comprising one or more nitrogen atoms; and $R^1$, $R^2$ and $R^3$ are each independently a linker into which a reactive group capable of linking to a polymer is introduced.

The first step is a step of synthesizing in an osmium complex represented by Chemical formula 6 in a trivalent ionic state, by introducing a tris-pyridinemethylamine-based ligand of Chemical formula 3 into an osmium salt of Chemical formula 5 in a tetravalent ionic state.

[Chemical formula 6]

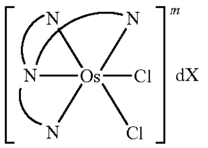

The second step is a step of synthesizing an osmium complex represented by any one of Chemical formulas 7 to 11 by introducing 1 kind or 2 kinds of monodentate ligands or bidentate ligands selected from the group consisting of N—N ligand, N-ligand, N—O ligand and O—O ligand into the osmium complex synthesized in the first step. Preferably, in the second step, to the osmium complex of Chemical formula 6 synthesized in the second step, 1 N—N ligand, 2 N ligands, 1 N ligand, 1 N—O ligand or 1 O—O ligand may be introduced.

[Chemical formula 7]

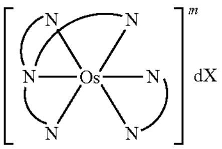

[Chemical formula 8]

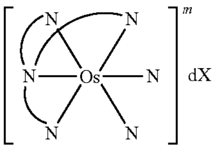

[Chemical formula 9]

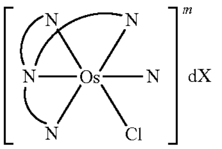

[Chemical formula 10]

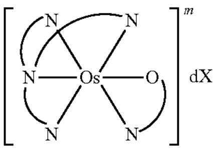

[Chemical formula 11]

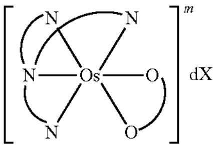

In one embodiment, the N ligand may be $—NO_2$, $—NCCH_3$, $—NH_3$ or a heterocyclic compound comprising one or more nitrogen atoms.

As one embodiment, the N—N ligand may be 2-pyridinecarboxamide, 2,2'-bipyridine, 2,2'-bithiazole or 2-pyridylmethylamine As one embodiment, the N—O ligand may be 2-picolinic acid, 2-aminophenol or 2-hydroxymethylpyridine.

As one embodiment, the O—O ligand may be catechol or acetylacetone.

The electron transfer mediator transition metal complex according to the present invention plays a role of transferring electrons obtained by reduction (glucose oxidation) of oxidoreductase, and may be used in a redox polymer form which is linked to a polymer matrix corresponding to a polymer backbone such as one or more kinds selected from the group consisting of poly(vinylpyridine) (PVP) or poly (vinylimidazole) (PVI), and poly allyl glycidyl ether (PAGE).

Accordingly, one additional aspect of the present invention, relates to a redox polymer comprising the transition metal complex for an electron transfer mediator and a polymer backbone.

In one embodiment, the redox polymer may comprise a linker structure which connects the polymer backbone and an organic series electron transfer mediator.

In addition, one additional aspect of the present invention relates to a sensing layer for an electrochemical biosensor comprising an enzyme capable of redoxing a liquid biological sample and an electron transfer mediator comprising the transition metal complex.

Oxidoreductase is a generic term for enzymes that catalyze the redox reaction of a living body, and in the present invention, it means a target material to be measured, for example, in case of a biosensor, an enzyme to be reduced by reacting with the target material. The reduced enzyme as above reacts with an electron transfer mediator, and then, the target material is quantified by measuring a signal such as a change in current generated. The oxidoreductase usable in the present invention may be one or more kinds selected from the group consisting of various kinds of dehydrogenase, oxidase, esterase and the like, and depending on the redox or detection target material, an enzyme having the target material as a substrate among enzymes belonging to the enzyme group may be selected and used.

More specifically, the oxidoreductase may be one or more kinds selected from the group consisting of glucose dehydrogenase, glutamate dehydrogenase, glucose oxidase, cholesterol oxidase, cholesterol esterase, lactate oxidase, ascorbic acid oxidase, alcohol oxidase, alcohol dehydrogenase, bilirubin oxidase, and the like.

On the other hand, the oxidoreductase may comprise a cofactor which plays a role of storing hydrogen stolen by the oxidoreductase from the target material to be measured (for example, target material) together, and for example, it may be one or more kinds selected from the group consisting of flavin adenine dinucleotide (FAD), nicotinamide adenine dinucleotide (NAD), pyrroloquinoline quinone (PQQ), and the like.

For example, when the blood glucose concentration is to be measured, glucose dehydrogenase (GDH) may be used as the oxidoreductase, and the glucose dehydrogenase may be flavin adenine dinucleotide-glucose dehydrogenase (FAD-GDH) comprising FAD as a cofactor, and/or nicotinamide adenine dinucleotide-glucose dehydrogenase comprising FAD-GDH as a cofactor.

In a specific embodiment, the usable oxidoreductase may be one or more kinds selected from the group consisting of FAD-GDH (for example, EC 1.1.99.10, etc.), NAD-GDH (for example, EC 1.1.1.47, etc.), PQQ-GDH (for example, EC1.1.5.2, etc.), glutamate dehydrogenase (for example, EC 1.4.1.2, etc.), glucose oxidase (for example, EC 1.1.3.4, etc.), cholesterol oxidase (for example, EC 1.1.3.6, etc.), cholesterol esterase (for example, EC 3.1.1.13, etc.), lactate oxidase (for example, EC 1.1.3.2, etc.), ascorbate oxidase (for example, EC 1.10.3.3, etc.), alcohol oxidase (for example, EC 1.1.3.13, etc.), alcohol dehydrogenase (for example, EC 1.1.1.1, etc.), bilirubin oxidase (for example, EC 1.3.3.5, etc.), and the like.

Most preferably, the oxidoreductase is glucose dehydrogenase capable of maintaining the activity of 70% or more in a 37° C. buffer solution for 1 week.

The sensing layer according to the present invention may contain a redox polymer of 20 to 700 parts by weight, for example, 60 to 700 parts by weight, or 30 to 340 parts by weight, based on oxidoreductase 100 parts by weight. The content of the redox polymer may be appropriately adjusted according to the activity of oxidoreductase.

Moreover, the sensing layer according to the present invention may further comprise a carbon nanotube for increasing the membrane performance Specifically, the carbon nanotube may further increase the performance of the sensing layer as the electron transfer rate is increased when a transition metal complex, particularly, osmium is used together.

In addition, the sensing layer according to the present invention may further comprise a crosslinking agent.

On the other hand, the sensing layer according to the present invention may further comprise one or more kinds of additives selected from the group consisting of a surfactant, an aqueous polymer, a tertiary ammonium salt, a fatty acid, a thickener, and the like, for a role of a role of a dispersing agent during reagent dissolution, an adhesive during reagent preparation, a stabilizer for storage for a long period of time, and the like.

The surfactant may play a role of distributing the composition evenly on an electrode to be aliquoted in a uniform thickness, when the composition is aliquoted. As the surfactant, one or more kinds selected from the group consisting of Triton X-100, sodium dodecyl sulfate, perfluorooctane sulfonate, sodium stearate, and the like. The reagent composition according to the present invention may contain the surfactant in an amount of 3 to 5 parts by weight, for example, 10 to 25 parts by weight, based on oxidoreductase 100 parts by weight, so as to appropriately perform the role of evenly distributing the reagent on an electrode to be aliquoted with a uniform thickness when the reagent is aliquoted. For example, when oxidoreductase having an activity of 700 U/mg is used, 10 to 25 parts by weight of a surfactant based on oxidoreductase 100 parts by weight may be contained, and when the activity of oxidoreductase is higher than this, the content of the surfactant may be adjusted lower than this.

The aqueous polymer is a polymer supporter of a reagent composition, which performs a role of helping stabilization and dispersing of an enzyme. As the aqueous polymer, one or more kinds selected from the group consisting of polyvinyl pyrrolidone (PVP), polyvinyl alcohol (PVA), polyperfluoro sulfonate, hydroxyethyl cellulose (HEC), hydroxypropyl cellulose (HPC), carboxy methyl cellulose (CMC), cellulose acetate, polyamide, and the like may be used. The reagent composition according to the present invention, may contain the aqueous polymer of 10 to 70 parts by weight, for example, 30 to 70 parts by weight, based on oxidoreductase 100 parts by weight, in order to sufficiently and appropriately exhibiting a role of helping stabilization and dispersing of oxidoreductase. For example, when oxidoreductase having an activity of 700 U/mg is used, the aqueous polymer of 30 to 70 parts by weight based on oxidoreductase 100 parts by weight may be contained, and when the activity of oxidoreductase is higher than this, the content of the aqueous polymer may be adjusted lower than this.

The aqueous polymer may have a weight average molecular weight of about 2,500 g/mol to 3,000,000 g/mol, for example, 5,000 g/mol to 1,000,000 g/mol, so as to effectively perform a role of helping stabilization and dispersing of the supporter and enzyme.

The thickener plays a role of strongly attaching a reagent to an electrode. As the thickener, one or more kinds selected from the group consisting of natrosol, diethylaminoethyl-dextran hydrochloride (DEAE-Dextran hydrochloride) and the like may be used. The electrochemical sensor according to the present invention, may contain the thickener in an amount of 10 to 90 parts by weight, for example, 30 to 90 parts by weight, based on oxidoreductase 100 parts by weight, in order to strongly attach the redox polymer according to the present invention to an electrode. For example, when oxidoreductase having an activity of 700 U/mg is used, the thickener of 30 to 90 parts by weight based on oxidoreductase 100 parts by weight may be contained, and when the activity of oxidoreductase is higher than this, the content of the thickener may be adjusted lower than this.

As other aspect, the present invention may be a device, preferably, an insertable device, more specifically, a device insertable into a human body, comprising this organic electron transfer mediator. In addition, preferably, the device may be an electrochemical biosensor, more preferably, an electrochemical glucose (blood glucose) sensor.

Specifically, there is no limitation on the type of the electrochemical biosensor, but it may be a continuous blood glucose monitoring sensor.

As the composition of this continuous blood glucose monitoring sensor, the present invention, may comprise for example, an electrode, an insulator, a substrate, a sensing layer comprising the redox polymer and oxidoreductase, a diffusion layer, a protection layer, and the like. In case of the electrode, two kinds of electrodes such as a working electrode and a counter electrode, and may comprise three kinds of electrodes such as a working electrode, a counter electrode and a reference electrode. In one embodiment, the biosensor according to the present invention may be an electrochemical biosensor produced by applying a reagent composition comprising a redox polymer comprising the organic series electron transfer mediator of Chemical formula 1 and an enzyme capable of redoxing a liquid biological sample, to a substrate having at least two, preferably, two or three electrodes, and drying. For example, in the electrochemical biosensor, a planar electrochemical biosensor, in which a working electrode and a counter electrode are equipped on opposite sides each other, and a sensing layer comprising a redox polymer having the organic series electron transfer mediator according to the present invention is laminated on the working electrode, and an insulator, a diffusion layer and a protective layer are laminated in order on both sides of the substrate equipped with the working electrode and counter electrode, is provided.

As a specific aspect, the substrate may be made of one or more kinds selected from the group consisting of PET (polyethylene terephthalate), PC (polycarbonate) and PI (polyimide).

In addition, the working electrode may use a carbon, gold, platinum, silver or silver/silver chloride electrode.

Furthermore, in case of an electrochemical biosensor having 2 electrodes, a counter electrode also plays a role of a reference electrode, and therefore, as the counter electrode, a gold, platinum, silver or silver/silver chloride electrode may be used, and in case of an electrochemical biosensor of three electrodes comprising a reference electrode, as the reference electrode, a gold, platinum, silver or silver/silver chloride electrode may be used, and as the counter electrode, a carbon electrode may be used.

As the diffusion layer, Nafion, cellulose acetate and silicone rubber may be used, and as the protective layer, silicone rubber, polyurethane, polyurethane-based copolymer and the liker may be used, but not limited thereto.

As a non-limited example, in case of two electrodes, the counter electrode also plays a role of the reference electrode, and therefore, silver chloride or silver may be used, and in case of three electrodes, as the reference electrode, silver chloride or silver may be used, and as the counter electrode, a carbon electrode may be used.

A specific embodiment of the present invention illustrates a biosensor for measuring glucose as an applicable example of the electrochemical biosensor, but by changing the type of enzyme comprised in the reagent composition of the present invention, it may be applied for a biosensor for quantification of various substances such as cholesterol, lactate, creatinine, hydrogen peroxide, alcohol, amino acid, and glutamate.

Mode for Invention

Hereinafter, the present invention will be described in more detail by the following examples. However, the following examples illustrate the present invention only, but the content of the present invention is not limited by the following examples.

EXAMPLE

Experimental Materials

Commercially purchased solvents and reagents were used without further purification process. In case of alumina for metal complex purification, neutral alumina of Aldrich was filtered using a 10 mL pipette. For the resin for the chloride counterion exchange of the complex, Dowex 1×4 chloride form, 50-100 mesh pf Aldrich was used.

$^{1}$H-NMR and $^{13}$C-NMR spectra were obtained using Varian Inova 400 (400 MHz for $^{1}$H, 100 MHz for $^{13}$C). All chemical shifts were determined proportionally to tetramethyl silane peaks (δ 0.00) or deuterated chloroform (δ7.26 for CDCl3 in $^{1}$H NMR, δ77.16 for CDCl3 in $^{13}$C NMR), or deuterated dimethylacetamide (62.50 for DMSO in $^{1}$H NMR, 639.52 for DMSO in $^{13}$C NMR). The mass spectra were obtained by ESI-Iontrap for low resolution and ESI-orbitrap mass spectrometer for high resolution, of LTQ XL model of ThermoFisher Scientific at Sogang University's Organic Chemistry Research Center.

Example 1. Synthesis of TPMA Ligands

TPMA ligands having various functional groups were synthesized according to the synthetic route shown in FIG. 1. Bis-2-pyridylmethylamine (1) and tris-2-pyridyl methylamine (10) were synthesized through reductive amination between 2-pyridyl aldehyde and 2-pyridylmethylamine Other ligands (11, 12, 15, 16) were synthesized by slightly modifying the method known in the document (Kojima, T.; Fukuzumi, S. *Chem. Eur. J.* 2007, 13, 8212-8222). 2-Chloromethylpyridine hydrochloride having various functional groups at position 4 was synthesized by Sn2 reaction with bis-2-pyridylmethylamine (1) at a ratio of 1:1 or Sn2 reaction with 2-pyridylmethylamine at a ratio of 1:2. In addition, No. 13 was synthesized by reducing ester, and No. 14 was synthesized through an aminolysis reaction with an excess of ethylenediamine Most of the synthesized TPMA ligands have three pyridine rings, so they have strong basicity and cannot be purified by column chromatography using silica, and therefore, they were purified by column chromatography using basic or neutral alumina.

1-1. Bis(2-pyridiylmethyl)amine (1)

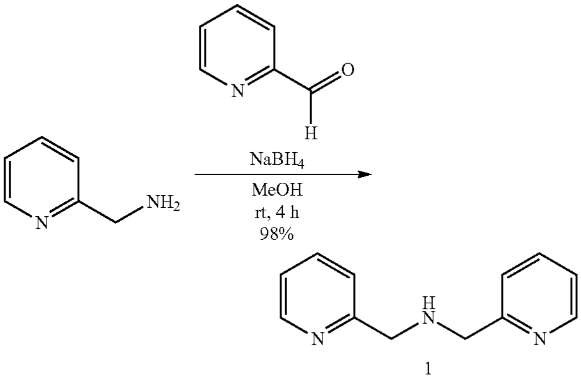

1

Put 2-pyridylaldehyde (3.0 g, 27 mmol) and 2-aminomethylpyridine (3.0 g, 27 mmol) in a round bottom flask, and then add methanol (25 mL). After stirring at a room temperature for 3 hours, slowly put NaBH 4 (3.1 g, 81 mmol) at 0° C. After completing addition, stir at a room temperature for 4 hours. When it is confirmed that the reaction completely progresses, add 10% hydrochloric acid solution and terminate the reaction. Concentrate the solution using a rotary evaporator, and adjust pH to 9 by adding $NaCO_3$ saturated aqueous solution. After transferring to a separatory funnel, extract the water layer with $CH_2Cl_2$ three times. Thereafter, add anhydrous $MgSO_4$ to the collected organic layer to remove water and filter a desiccant using a glass filter under reduced pressure. Remove the organic solvent using a rotary evaporator. Through this, Product 1 in a yellow oil form was obtained; (5.4 g, 98%); $^1H$ NMR (400 MHz, $CDCl_3$) δ 8.57 (d, J=4.8 Hz, 2H), 7.65 (dd, J=7.2, 4.8 Hz, 2H), 7.37 (d, J=7.6 Hz, 2H), 7.17 (d, J=5.2, 7.2 Hz, 2H), 3.99 (s, 4H)

1-2. 2,4-Diethoxycarbonylpyridine (2)

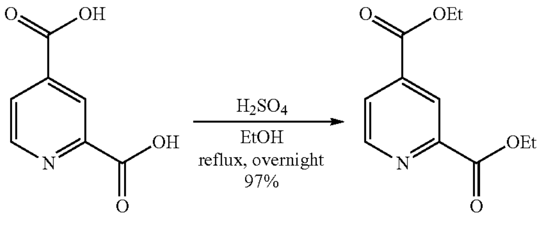

2

Put 2,4-pyridinedicarboxylic acid (5 g, 30 mmol) in a round bottom flask, and then add ethanol (250 mL) to dissolve it. After adding concentrated sulfuric acid (3.28 mL) in a reaction flask, and then install a reflux pipe to stir while refluxing at 80° C. for 24 hours. After colling the reaction flask to a room temperature, remove ethanol using a rotary evaporator. Add $NaCO_3$ saturated aqueous solution and transfer to a separatory funnel, and then extract the water layer with $CH_2Cl_2$ three times. Thereafter, add anhydrous $MgSO_4$ to the collected organic layer to remove water and filter a desiccant using a glass filter under reduced pressure. Remove the organic solvent using a rotary evaporator. Through this, Product 2 in a white solid form was obtained; (6.5 g, 97%); $^1H$ NMR (400 MHz, $CDCl_3$) δ 8.92 (d, J=5.6 Hz, 1H), 8.65 (s, 1H), 8.04 (d, J=6.0 Hz, 1H), 4.52 (q, J=6.4 Hz, 2H), 4.46 (q, J=5.6 Hz, 2H), 1.48 (t, J=6.0 Hz, 3H), 1.43 (t, J=6.0 Hz, 3H)

1-3. 4-Ethoxycarbonyl-2-hydroxymethylpyridine (3)

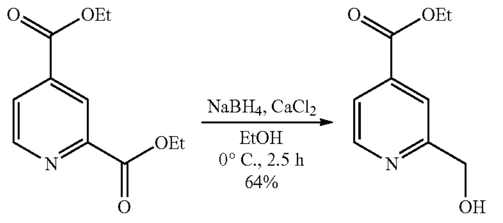

2 3

Put a starting material (2) (6.0 g, 27 mmol) and $NaBH_4$ (0.664 g, 35 mmol) in a round bottom flask and add ethanol (50 mL) to dissolve it. Slowly add $CaCl_2$ (3.0 g, 27 mmol) in a reaction flask at 0° C. by dissolving in ethanol. After completing addition, stir at 0° C. for 2 hours and 20 minutes. When it is confirmed that the reaction completely progresses, add concentrated sulfuric acid and terminate the reaction. Filter the white precipitate using a glass filter, and concentrate the solution using a rotary evaporator. Add $NaCO_3$ saturated aqueous solution and transfer to a separatory funnel, and then extract the water layer with $CH_2Cl_2$ three times. Thereafter, add anhydrous $MgSO_4$ to the collected organic layer to remove water and filter a desiccant using a glass filter under reduced pressure. Remove the organic solvent using a rotary evaporator. Through this, Product 3 in a yellow solid form was obtained; (3.1 g, 64%); $^1H$ NMR (400 MHz, $CDCl_3$) δ 8.96 (d, J=5.6 Hz, 1H), 8.42 (s, 1H), 8.34 (d, J=5.6 Hz, 1H), 5.22 (s, 2H), 4.53 (q, J=7.2 Hz, 2H), 1.47 (t, J=6.8 Hz, 3H)

1-4. 4-Ethoxycarbonyl-2-chloromethylpyridine hydrochloride (4)

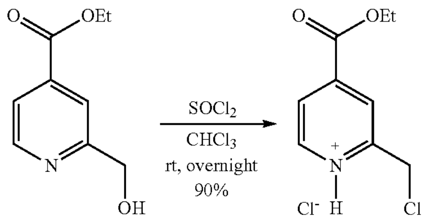

3 4

Put a starting material (3) (2.9 g, 16 mmol) in a round bottom flask and add $CH_2Cl_2$ (30 mL) to dissolve it. Slowly add thionyl chloride (9.5 g, 80 mmol) to a reaction flask after diluting it in $CH_2Cl_2$ (15 mL). After completing addition, stir at a room temperature overnight. When it is confirmed that the reaction completely progresses, remove the solvent using a rotary evaporator. Through this, Product 4 in a white solid form was obtained; (3.616 g, 90%); $^1H$ NMR (400 MHz, $CDCl_3$) δ 8.82 (d, J=6.0 Hz, 1H), 8.55 (s, 1H), 8.35 (d, J=6.4 Hz, 1H), 5.24 (s, 2H), 4.54 (q, J=7.6 Hz, 2H), 1.48 (t, J=7.2 Hz, 3H)

1-5. 4-Methoxy-2-hydroxymethylpyridine (5)

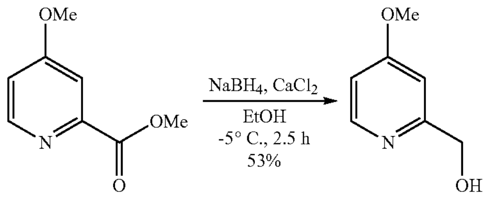

5

Put 4-methoxypyridine-2-carboxylate (4.95 g, 29 mmol) and $NaBH_4$ (1.45 g, 44 mmol) in a round bottom flask and add ethanol (40 mL) to dissolve it. Slowly add $C_aCl_2$ (3.28 g, 29 mmol) to a reaction flask at 0° C. by dissolving it in ethanol. After completing addition, stir at −5° C. for 2 hours and 30 minutes. When it is confirmed that the reaction completely progresses, add concentrated sulfuric acid and terminate the reaction. Filter the white precipitate using a glass filter, and concentrate the solution using a rotary evaporator. Add $NaCO_3$ saturated aqueous solution and transfer to a separatory funnel, and then extract the water layer with $CH_2Cl_2$ three times. Thereafter, add anhydrous $MgSO_4$ to the collected organic layer to remove water and filter a desiccant using a glass filter under reduced pressure. Remove the organic solvent using a rotary evaporator. Through this, Product 5 in a white solid form was obtained; (2.14 g, 53%); $^1H$ NMR (400 MHz, $CDCl_3$) δ 8.37 (d, J=4.0 Hz, 1H), 6.78 (s, 1H), 6.74 (d, J=3.2 Hz, 1H), 4.71 (s, 2H), 3.86 (s, 3H)

1-6. 4-Methoxy-2-chloromethylpyridine hydrochloride (6)

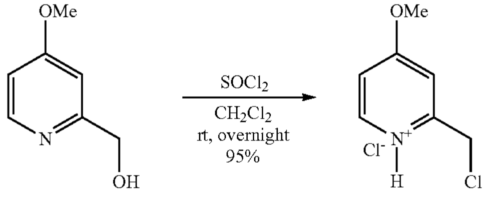

5 6

Put a starting material (5) (1.60 g, 11 mmol) in a round bottom flask and add $CH_2Cl_2$ (20 mL) to dissolve it. Slowly add thionyl chloride (6.83 g, 57 mmol) to a reaction flask after diluting it in $CH_2Cl_2$ (10 mL). After completing addition, stir at a room temperature overnight. When it is confirmed that the reaction completely progresses, remove the solvent using a rotary evaporator. Through this, Product 6 in a white solid form was obtained; (2.11 g, 95%); $^1H$ NMR (400 MHz, $CD_3CN$) δ 8.42 (d, J=6.8 Hz, 1H), 7.43 (s, 1H), 7.31 (d, J=6.4 Hz, 1H), 4.98 (s, 2H), 4.06 (s, 3H)

1-7. 2-(Hydroxymethyl)-4-pyridinecarboxamide (7)

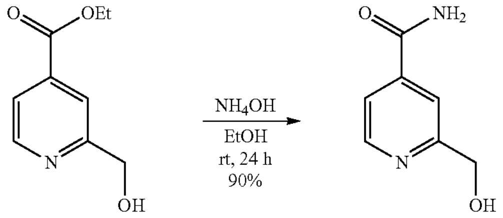

3 7

Put a starting material (3) (1.60 g, 11 mmol) in a round bottom flask and add ethanol (10 mL) to dissolve it. Slowly add 30% ammonia water (30 mL) to a reaction flask. After completing addition, stir at a room temperature for 24 hours. When it is confirmed that the reaction completely progresses, remove the solvent using a rotary evaporator. After that, it was used for the next reaction without an additional purification process. Through this, Product 7 in a white solid form was obtained; (0.78 g, 90%); $^1H$ NMR (400 MHz, DMSO) δ 8.60 (d, J=4.0 Hz, 1H), 8.42 (d, J=4.0 Hz, 1H, $NH^1$), 7.89 (s, 1H), 7.63 (d, J=4.0 Hz, 1H), 7.53 (d, J=4.0 Hz, 1H, $NH^2$), 4.61 (s, 2H)

1-8. 4-Cyano-2-chloromethylpyridine (8)

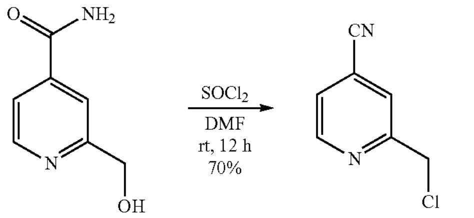

7 8

Put a starting material (7) (94 mg, 0.55 mmol) in a round bottom flask and add DMF (3 mL) purified by distillation to dissolve it. Slowly add thionyl chloride (325 mg, 2.8 mmol) to a reaction flask at 0° C. after diluting it in DMF (6 mL). After completing addition, stir at a room temperature for 12 hours. Add $NaCO_3$ saturated aqueous solution to neutralize it, thereby terminating the reaction. After transferring the product of the flask to a separatory funnel, extract the water layer with ethyl acetate three times. Thereafter, wash the organic layer with water until DMF is removed all. Add anhydrous $MgSO_4$ to the collected organic layer to remove water and filter a desiccant using a glass filter under reduced pressure. Remove the organic solvent using a rotary evaporator. Through this, Product 8 in a brown oil form was obtained; (695 mg, 70%); $^1H$ NMR (400 MHz, $CDCl_3$) δ 7.76 (d, J=4.8 Hz, 1H), 7.76 (s, 1H), 7.50 (d, J=4.8 Hz, 1H), 4.73 (s, 2H), $^{13}C$ NMR (100 MHz, $CDCl_3$) δ 158.28, 150.32, 124.46, 124.29, 121.47, 116.12 and 45.63

1-9. 2-thiazoylmethylamine (9)

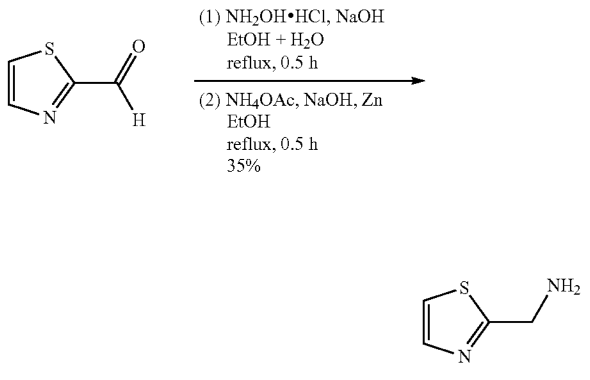

9

Put $NH_2OH$·HCl (2.3 g, 30 mmol), 2-thiazolecarboxyaldehyde (2.5 g, 20 mmol), and NaOH (2.6 g, 60 mmol) in a round bottom flask, and add ethanol (20 mL) and distilled water (4 mL) to dissolve it. Install a reflux pipe in a reaction flask and reflux while stirring at 80° C. for 30 minutes. After cooling to a room temperature, add 2N hydrochloric acid to acidify it by pH 4. After transferring the product of the flask to a separatory funnel, extract the water layer with $Et_2O$ two times. Thereafter, add anhydrous $MgSO_4$ to the collected organic layer to remove water and filter a desiccant using a glass filter under reduced pressure. Remove the organic solvent using a rotary evaporator. Through this, obtain an intermediate product in a white solid form. Add ethanol (30 mL) and 30% ammonia water (60 mL) to this intermediate product to dissolve it. Add zinc dust (10.1 g, 200 mmol) and ammonium acetate (1.3 g, 20 mmol) in order, and install a reflux pipe and reflux while stirring at 80° C. for 30 minutes. After cooling to a room temperature, filter it using a glass filter. Dilute the filtered solution by adding water and transferring it to a separatory funnel, and then extract it with $CH_2Cl_2$ three times. Thereafter, add anhydrous $MgSO_4$ to the collected organic layer to remove water and filter a desiccant using a glass filter under reduced pressure. Remove the organic solvent using a rotary evaporator. Through this, Product 9 in a yellow oil form was obtained; (0.8 g, 35%); $^1$H NMR (400 MHz, DMSO) δ 7.68 (d, J=3.2 Hz, 1H), 7.55 (d, J=3.2 Hz, 1H), 3.98 (s, 2H), 2.32 (br, 2H)

1-10. Tris(2-pyridiylmethyl)amine (10)

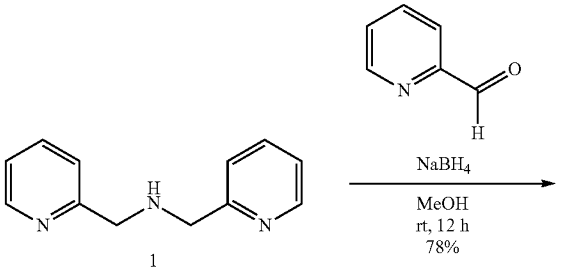

1

-continued

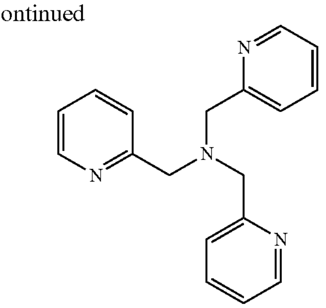

10

Put a starting material (1) (1.05 g, 5.3 mmol) and 2-pyridylaldehyde (0.63 g, 5.3 mmol) in a round bottom flask and add methanol (15 mL). Stir at a room temperature for 2 hours and slowly add NaBH 4 (0.61 g, 16 mmol) at 0° C. When it is confirmed that the reaction completely progresses, add 10% hydrochloric acid solution and terminate the reaction. Concentrate the solution using a rotary evaporator, and adjust pH to 9 by adding $NaCO_3$ saturated aqueous solution. After transferring to a separatory funnel, extract the water layer with $CH_2Cl_2$ three times. Thereafter, add anhydrous $MgSO_4$ to the collected organic layer to remove water and filter a desiccant using a glass filter under reduced pressure. Remove the organic solvent using a rotary evaporator. After that, purify it by recrystallization with $Et_2O$, Product 10 in a colorless crystal form was obtained; (1.2 g, 78%); $^1$H NMR (400 MHz, $CDCl_3$) δ 8.53 (d, J=4.4 Hz, 3H), 7.65 (dd, J=5.0, 7.6 Hz, 3H), 7.58 (d, J=7.6 Hz, 3H), 7.15 (dd, J=5.6, 7.2 Hz, 3H), 3.88 (s, 6H)

1-11. 2-(Bis(4,4'-ethoxycarbonyl-2,2'-pyridinyl) methylamino)methylpyridine (11)

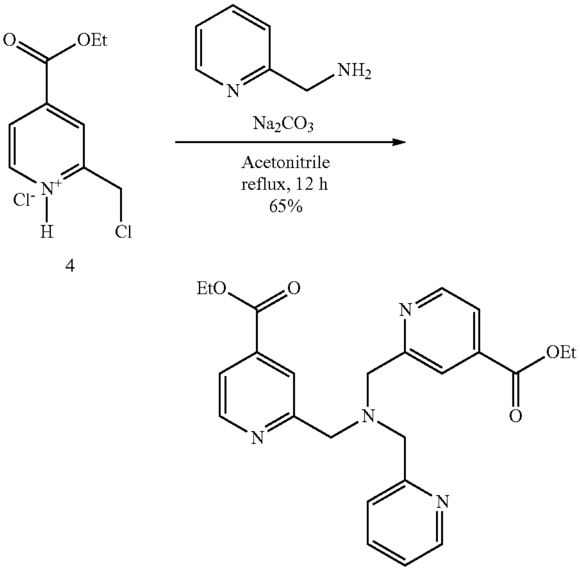

4

11

Put a starting material (4) (1.0 g, 4.25 mmol), 2-pyridylmethylamine (0.21 g, 1.93 mmol), $Na_2CO_3$ (4.5 g, 42.5 mmol) and acetonitrile (20 mL) in a round bottom flask. Install a reflux pipe in a reaction flask and reflux while stirring at 80° C. for 12 hours. When the reaction is completed, cool it to a room temperature and then remove an excess of $Na_2CO_3$ using a glass filter. Concentrate the solution using a rotary evaporator, and purify a mixture in a dark red oil form by column chromatography by alumina using a developing solution having the composition of hexane:EtOAc=2:5, thereby obtaining Product 11 in a red oil form; (0.55 g, 65%); $^1$H NMR (400 MHz, $CDCl_3$) δ 8.68 (d, J=5.2 Hz, 2H), 8.54 (d, J=5.0 Hz, 1H), 8.10 (s, 2H), 7.70 (d, 2H), 7.69 (dd, 1H), 7.60 (d, J=3.6 Hz, 1H), 7.16 (dd, J=6.0, 7.2 Hz, 1H), 4.42 (q, J=7.2 Hz, 4H), 3.99 (s, 2H), 3.93 (s, 4H) 1.42 (t, J=7.2 Hz, 6H)

1-12. 2-(Bis(2-pyridinyl)methylamino)methyl-4-ethoxycarbonylpyridine (12)

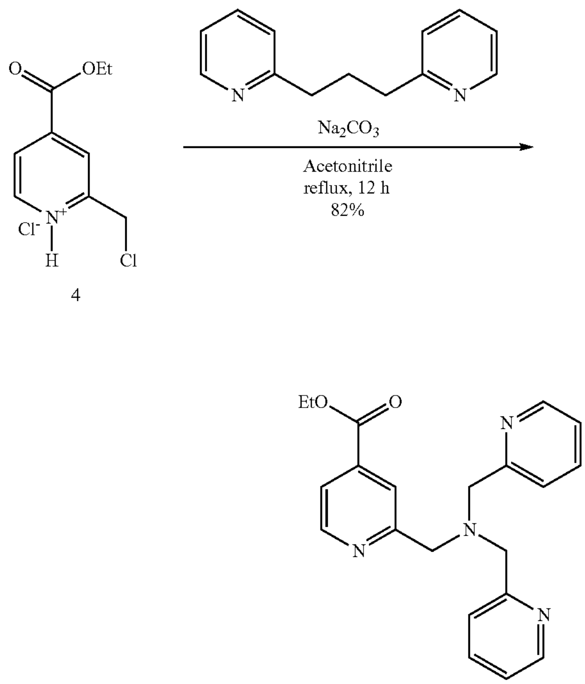

4

12

Put a starting material (1) (0.35 g, 1.77 mmol), a staring material (4) (0.5 g, 1.94 mmol), $Na_2CO_3$ (2.2 g, 19.4 mmol) and acetonitrile (15 mL) in a round bottom flask. Install a reflux pipe in a reaction flask and reflux while stirring at 80° C. for 12 hours. When the reaction is completed, cool it to a room temperature and then remove an excess of $Na_2CO_3$ using a glass filter. Concentrate the solution using a rotary evaporator, and purify a mixture in a dark red oil form by column chromatography by basic alumina using acetonitrile as a developing solution, thereby obtaining Product 12 in an orange oil form; (0.53 g, 82%); $^1$H NMR (400 MHz, $CDCl_3$) δ 8.68 (d, J=4.8 Hz, 1H), 8.54 (d, J=4.0 Hz, 2H), 8.12 (s, 1H), 7.69 (d, J=4.0 Hz, 1H), 7.65 (dd, 2H), 7.60 (d, J=7.6 Hz, 2H), 7.15 (dd, J=6.0, 7.2 Hz, 2H), 4.42 (q, J=6.8 Hz, 2H), 3.96 (s, 2H), 3.89 (s, 4H) 1.42 (t, J=6.8 Hz, 3H)

1-13. 2-(Bis(2-pyridinyl)methylamino)methyl-4-hydroxymethylpyridine (13)

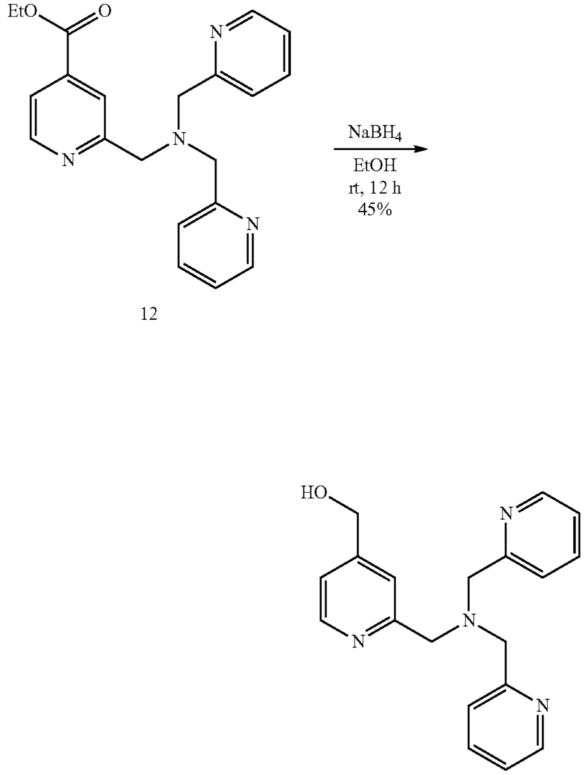

12

13

Put a staring material (12) (100 mg, 0.28 mmol) in a round bottom flask, and then add ethanol (10 mL) to dissolve it. Slowly put $NaBH_4$ (21 mg, 0.84 mmol) at 0° C. and after adding all, stir at a room temperature for 12 hours. After 12 hours, add a saturated ammonium chloride aqueous solution to terminate the reaction. Filter the white precipitate using a glass filter, and concentrate the solution using a rotary evaporator. Add an $NaCO_3$ saturated aqueous solution and transfer it to a separatory funnel, and then extract the water layer with $CH_2Cl_2$ three times. Thereafter, add anhydrous $MgSO_4$ to the collected organic layer to remove water and filter a desiccant using a glass filter under reduced pressure. Remove the organic solvent using a rotary evaporator. Through this, Product 13 in a light yellow oil form was obtained; (40 mg, 45%); $^1$H NMR (400 MHz, $CDCl_3$) δ 8.51 (d, J=4.8 Hz, 2H), 8.47 (d, J=5.2 Hz, 1H), 7.64 (dd, J=3.6, 4.0 Hz 2H), 7.59 (d, J=5.2 Hz, 2H), 7.55 (s, 1H), 7.16 (d, J=5.2 Hz, 1H), 7.13 (dd, J=3.2, 3.2 Hz, 2H), 4.73 (s, 2H), 3.88 (s, 2H), 3.86 (s, 4H)

1-14. 2-(Bis(2-pyridinyl)methylamino)methyl-4-(2-aminoethyl)pyridine carboxamide (14)

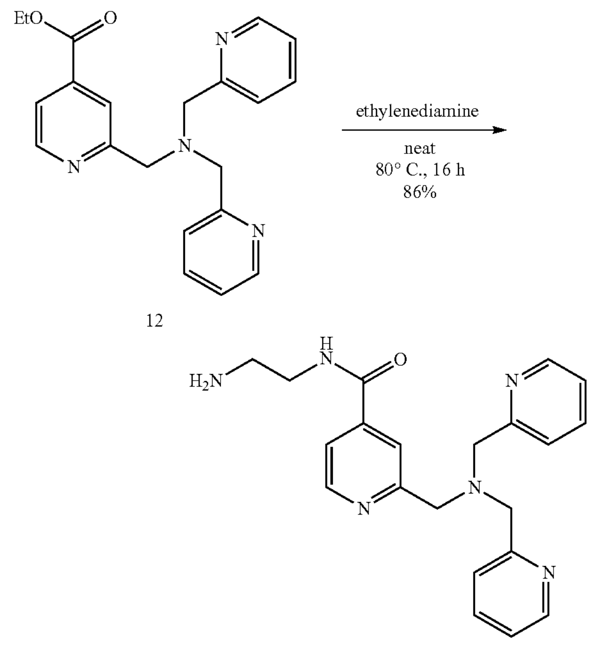

12

14

Slowly add a starting material (12) (1.35 g, 3.7 mmol) to ethylene diamine (22.5 g, 370 mmol) purified by dissolving in a minimum quantity of $CH_2Cl_2$ in a round bottom flask. Install a reflux pipe in a reaction flask, and stir at 80° C. for 16 hours. When the reaction is completed, cool to a room temperature and then pour water 30 mL. After transferring the product of the flask to a separatory funnel, extract the water layer with $CH_2Cl_2$ three times. Thereafter, add anhydrous $MgSO_4$ to the collected organic layer to remove water and filter a desiccant using a glass filter under reduced pressure. Remove the organic solvent using a rotary evaporator. Through this, Product 14 in a light yellow oil form was obtained; (1.20 g, 86%); $^1$H NMR (400 MHz, $CDCl_3$) δ 8.62 (d, J=4.0 Hz, 1H), 8.54 (d, J=8.0 Hz, 2H), 8.23 (s, 1H), 7.64 (dd, J=8.0, 8.0 Hz, 2H), 7.55 (d, J=4.0 Hz, 1H), 7.49 (d, J=8.0 Hz, 2H), 7.43 (br, 1H), 7.15 (dd, J=6.0, 6.0 Hz, 2H), 3.93 (s, 2H), 3.87 (s, 4H), 3.55 (t, J=8.0 Hz, 2H), 2.98 (t, J=8.0 Hz, 2H)

1-15. 2-(bis(4,4'-methoxy-2,2'-pyridinyl)methylamino)methylpyridine (15)

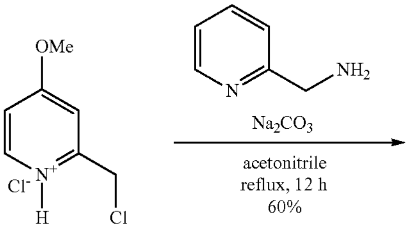

6

-continued

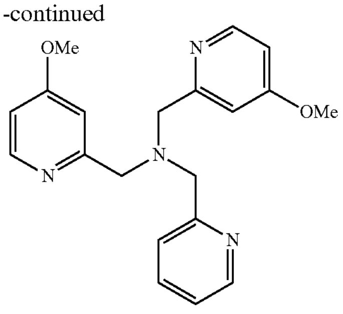

15

Put a starting material (6) (1.0 g, 5.18 mmol), 2-pyridylmethylamine 0.28 g, 2.59 mmol), $Na_2CO_3$ (2.7 g, 25.9 mmol) and acetonitrile (20 mL) in a round bottom flask. Install a reflux pipe in a reaction flask and reflux while stirring at 80° C. for 12 hours. When the reaction is completed, cool it to a room temperature and then remove an excess of $Na_2CO_3$ using a glass filter. Concentrate the solution using a rotary evaporator, and purify a mixture in a dark red oil form by column chromatography by neutral alumina using acetonitrile as a developing solution, thereby obtaining Product 15 in an orange oil form; (0.54 g, 60%); $^1$H NMR (400 MHz, $CDCl_3$) δ 8.55 (d, J=4.8 Hz, 1H), 8.34 (d, J=5.6 Hz, 2H), 7.64 (dd, J=4.8, 4.4 Hz, 1H), 7.58 (d, J=4.0 Hz, 1H), 7.21 (s, 2H), 7.15 (dd, J=5.2, 4.4 Hz, 1H), 6.68 (d, J=3.2 Hz, 2H), 3.90 (s, 2H), 3.85 (s, 4H) 3.84 (s, 6H)

1-16. 2-(bis(4,4'-cyano-2,2'-pyridinyl)methylamino)methylpyridine (16)

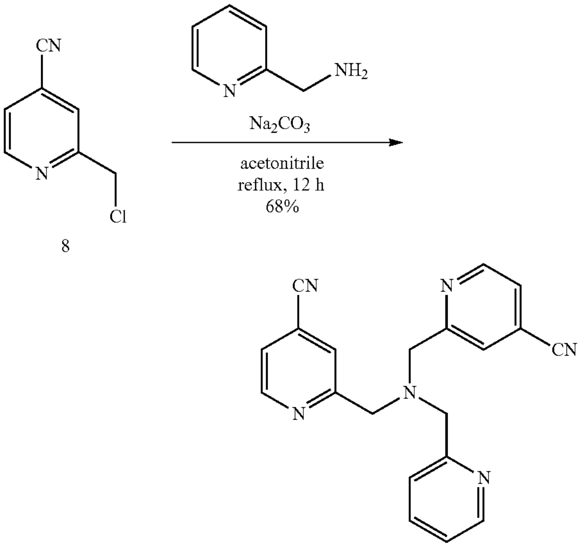

8

16

Put a starting material (8) (54 mg, 0.345 mmol), 2-pyridylmethylamine 17 mg, 0.157 mmol), $Na_2CO_3$ (166 mg, 1.57 mmol) and acetonitrile (10 mL) in a round bottom flask. Install a reflux pipe in a reaction flask and reflux while stirring at 80° C. for 12 hours. When the reaction is completed, cool it to a room temperature and then remove an excess of $Na_2CO_3$ using a glass filter. Concentrate the solution using a rotary evaporator, and purify a mixture in a dark red oil form by column chromatography by neutral alumina using acetonitrile as a developing solution, thereby obtaining Product 16 in a yellow oil form; (36 mg, 68%); $^1$H NMR (400 MHz, $CDCl_3$) δ 8.73 (d, J=5.2 Hz, 2H), 8.58 (d, J=4.4 Hz, 1H), 7.80 (s, 2H), 7.70 (dd, J=6.8, 5.2 Hz, 1H), 7.46 (d, J=5.2 Hz, 1H), 7.41 (d, J=4.4 Hz, 2H), 7.20 (dd, J=7.2, 4.4 Hz, 1H), 3.99 (s, 4H), 3.91 (s, 2H)

1-17. 2-(Bis(4,4'-ethoxycarbonyl-2,2'-pyridinyl) methylamino)methylthiazole (17)

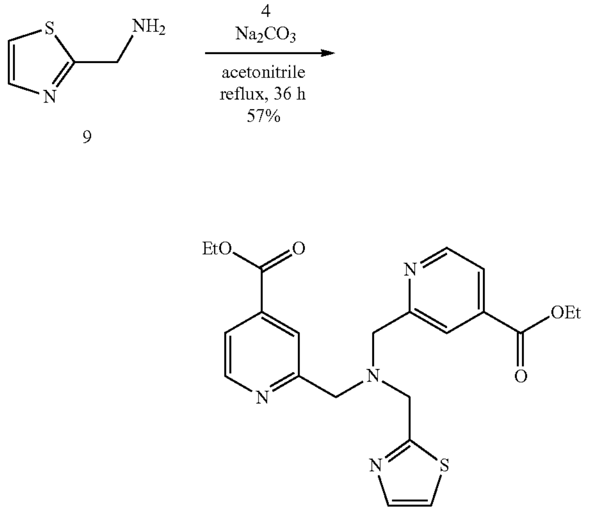

9

17

Put a starting material (4) (0.45 g, 1.929 mmol), a starting material (9) (0.1 g, 0.877 mmol), $Na_2CO_3$ (2.04 g, 19.3 mmol) and acetonitrile (15 mL) in a round bottom flask. Install a reflux pipe in a reaction flask and reflux while stirring at 80° C. for 36 hours. When the reaction is completed, cool it to a room temperature and then remove an excess of $Na_2CO_3$ using a glass filter. Concentrate the solution using a rotary evaporator, and purify a mixture in an orange oil form by column chromatography by neutral alumina using acetone as a developing solution, thereby obtaining Product 17 in a yellow oil form; (0.22 g, 57%); $^1$H NMR (400 MHz, $CDCl_3$) δ 8.69 (d, J=7.2 Hz, 2H), 8.18 (s, 2H), 7.73 (d, J=4.0 Hz, 1H), 7.72 (d, J=7.2 Hz, 2H), 7.31 (d, J=4.0 Hz, 2H), 4.43 (q, J=7.2 Hz, 4H), 4.16 (s, 2H), 4.04 (s, 4H), 1.43 (t, J=7.2 Hz, 6H)

Example 2. Synthesis of TPMA-Based Osmium Complexes

From ligands synthesized from Example 1 (1-1 to 1-17), $[Os(TPMA)Cl_2]^+(PF_6^-)$ complexes and derivatives thereof were synthesized. All the synthesized complexes could be synthesized from ammonium hexachloroosmate. Then, as a step in which an osmium salt in a tetravalent ionic state is reduced to an osmium complex in a trivalent ionic state, after the reaction, precipitation was obtained in an ammonium hexafluorophosphate ($NH_4PF_6$) aqueous solution to initially obtain all in a form of a complex having $PF_6$ as a counter ion. This synthesis reaction scheme was shown in FIG. 2.

As all the $[Os(TPMA)Cl_2]^+(PF_6^-)$complexes have paramagnetic characteristics, it could not be observed by $^1$H-NMR. This was because unpaired electrons of the paramagnetic material interact with nuclear spin to shorten the relaxation time. Therefore, for the produced osmium complexes, the synthesis result and oxidation state of the materials were determined through ESI-MS. In addition, the crystal structure of the $[Os(TPMA)Cl_2]^+(PF_6^-)$ (18) complex could be confirmed by Single crystal X-ray diffraction, and this was shown in FIG. 3.

By reacting the $[Os(TPMA)Cl_2]^+(PF_6^-)$-based complexes synthesized by an additional step with various monodentate ligands or bidentate ligands, various kinds of osmium complexes were synthesized. The $[Os(TPMA)(L)_{1\text{-}2}]^+(PF_6^-)$-based complexes could be synthesized by reacting the monodentate ligands such as 1-methylimidazole, pyridine and the like, and bidentate ligands such as 4-methyoxy-2-pyridylcarboxyamide, picolinic acid, catechol, acetylacetone and the like with $[Os(TPMA)Cl_2]^+(PF_6^-)$ and passing through an exchange reaction with a chloride (Cl) ligand. This synthesis reaction scheme was shown in FIG. 4.

As all the synthesized $[Os(TPMA)(L)_{1\text{-}2}]^{n+}(PF_6^-)_n$-based complexes have paramagnetic characteristics as same as the $[Os(TPMA)Cl_2]^+(PF_6^-)$ complexes, they could not be observed by $^1$H-NMR, and the synthesis result and oxidation state of the materials were determined by ESI-MS. Among the $[Os(TPMA)(L)_{1\text{-}2}]^{n+}(PF_6^-)_n$-based complexes, in case of compounds (27 ~33) in which oxygen is coordinated, such as catechol, acetylacetone, picolinic acid, and the like, during the reaction, the reaction was carried out by adding a based such as triethylamine (TEA) or sodium hydroxide (NaOH).

Among the synthesized TPMA-based complexes, in case of complexes having a hydroxymethyl (—$CH_2OH$) group in a TPMA ligand such as 21, 31 and 32, a mass signal in which the hydroxy (—OH) group was removed was characteristically removed. This is determined that the mass signal in which the hydroxy group was removed was observed, as a pyridylmethyl (—$PyCH_2$) group with high reactivity is easily ionized and has stability. (FIG. 5)

In case of 26, 34 and 35 complexes in which a monodentate ligand, 1-methylimidazole was reacted with $[Os(TPMA)Cl_2]^+(PF_6^-)$, they could be obtained with high yield when they were reacted under 2 ~10 equivalents of 1-methylimidazole and ethylene glycol solvent under the condition of 130 ~180° C., 3 ~12 h. However, in case of the $[Os(TPMA)(imi)Cl]^{n+}(PF_6^-)_n$ complex in which only one 1-methylimidazole was coordinated, the reaction was not progressed at all when reacting only 1 equivalent of 1-methylimidazole, and when 2 equivalents were added, this could not be selectively obtained, such that 2 of imidazole ligands were coordinated, and the like.

All the synthesized TPMA-based osmium complexes were obtained initially in a $PF_6^-$ counter ion form, and a complex in a $[Os(TPMA)Cl_2]^+(Cl^-)$ or $[Os(TPMA)(L)_{1\text{-}2}]^{n+}(Cl^-)_n$ form could be obtained using $Cl^-$ ion exchange resin. Most of the TPMA-based osmium complexes showed a large difference in solubility depending on the form of the counter ion. When $PF_6^-$ was in the form of a counter ion, they showed good solubility in acetonitrile and acetone solvents, but in water and methanol, they showed poor solubility. Conversely, in the $Cl^-$ counter ion form, they showed good solubility in water and methanol, and they were hardly dissolved in an organic solvent such as acetonitrile and acetone.

2-1. $[Os(TPMA)Cl_2]^+(PF_6^-)$ Complex (18)

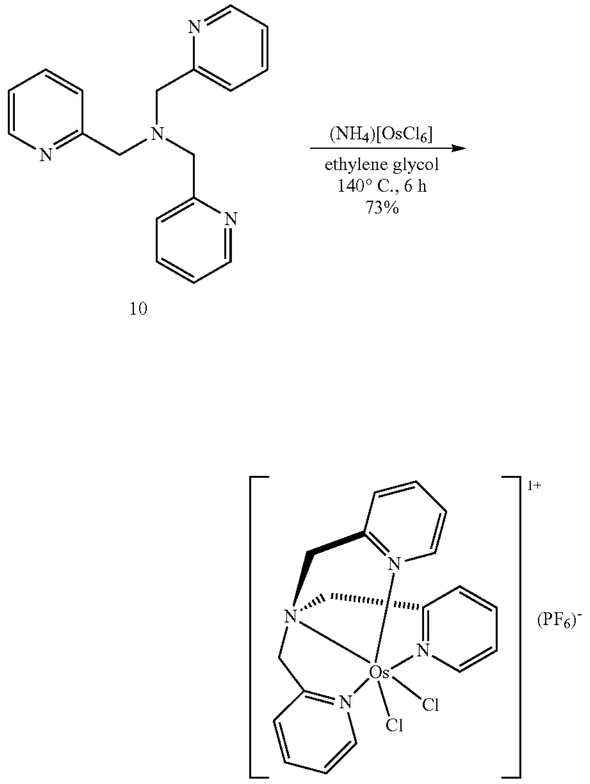

10

18

Put ammonium hexachloroosmate (30 mg, 0.068 mmol) and a starting material (10) (20 mg, 0.068 mmol) in a glass culture tube and add ethylene glycol (2 mL) to make a mixed solution. Then, blow argon gas for 10 minutes to create an argon atmosphere in the glass culture tube, and then reflux at 140° C. for 6 hours. Slowly drop the solution in which the reaction was completed into a saturated solution, by adding an excess of ammonium hexafluorophosphate to distilled water. Filter the precipitate generated in the solution and wash it with distilled water and diethyl ether, thereby obtaining green solid Product 18 having a counter ion of $PF_6^-$. (35 mg, 73%) To convert the counter ion to $Cl^-$, dissolve the $PF_6^-$ product in a small amount (~1 mL) of acetonitrile, and then make an excess of distilled water (25 mL) mixture with $Cl^-$ ion exchange resin, and stir overnight. Filter the remaining $Cl^-$ resin and collect the filtrate, and remove the solvent using distillation under reduced pressure, thereby obtaining a product in which a counter ion is $Cl^-$. ESI-MS (Low resolution): Calcd for cation$[M]^+$ $C_{18}H_{18}Cl_2N_4Os$: 552.05 Found: 552.16$[M]^+$.

2-2. $[Os(TPMA)Cl_2]^+(PF_6^-)$ Complex (19)

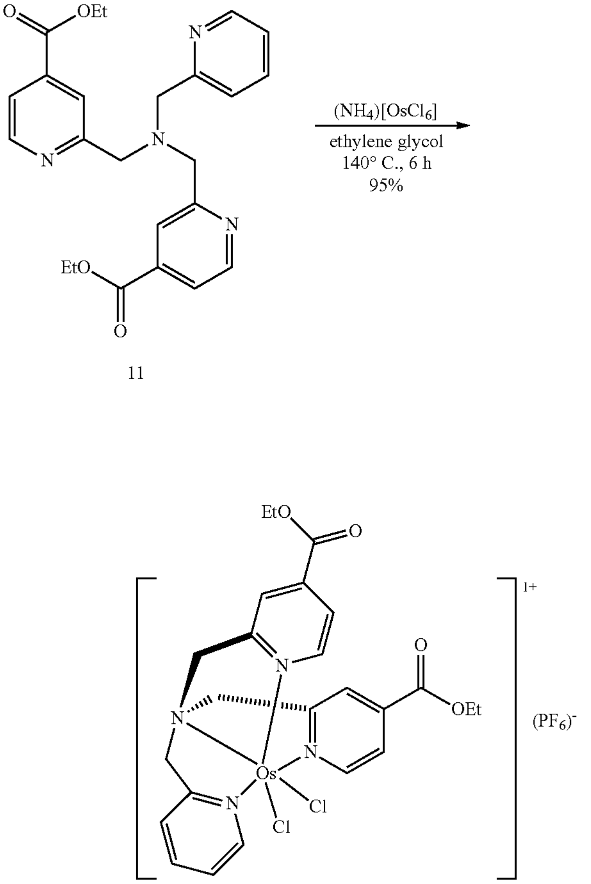

11

19

Put ammonium hexachloroosmate (129 mg, 0.293 mmol) and a starting material (11) (120 mg, 0.293 mmol) in a glass culture tube and add ethylene glycol (3 mL) to make a mixed solution. Then, blow argon gas for 10 minutes to create an argon atmosphere in the glass culture tube, and then reflux at 140° C. for 6 hours. Slowly drop the solution in which the reaction was completed into a saturated solution, by adding an excess of ammonium hexafluorophosphate to distilled water. Filter the precipitate generated in the solution and wash it with distilled water and diethyl ether, thereby obtaining brown solid Product 19 having a counter ion of $PF_6^-$. (220 mg, 95%) To convert the counter ion to $Cl^-$, dissolve the $PF_6^-$ product in a small amount (~1 mL) of acetonitrile, and then make an excess of distilled water (25 mL) mixture with $Cl^-$ ion exchange resin, and stir overnight. Filter the remaining $Cl^-$ resin and collect the filtrate, and remove the solvent using distillation under reduced pressure, thereby obtaining a product in which a counter ion is $Cl^-$. ESI-MS (Low resolution): Calcd for cation$[M]^+$ $C_{24}H_{26}Cl_2N_4Os$: 696.09 Found: 696.25$[M]^+$.

2-3. $[Os(TPMA)Cl_2]^+(PF_6^-)$ Complex (20)

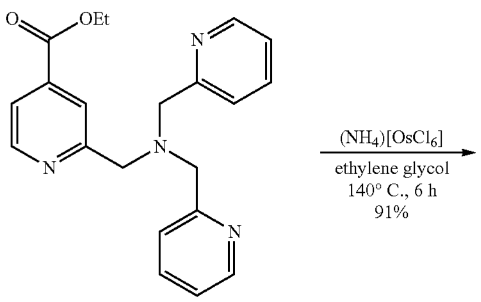

12

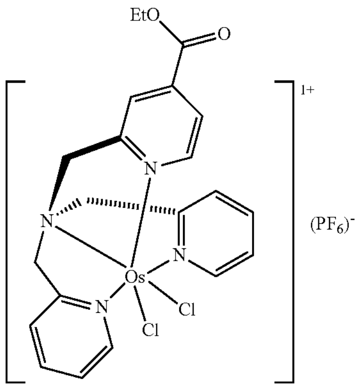

20

Put ammonium hexachloroosmate (327 mg, 0.744 mmol) and a starting material (12) (270 mg, 0.744 mmol) in a glass culture tube and add ethylene glycol (3 mL) to make a mixed solution. Then, blow argon gas for 10 minutes to create an argon atmosphere in the glass culture tube, and then reflux at 140° C. for 6 hours. Slowly drop the solution in which the reaction was completed into a saturated solution, by adding an excess of ammonium hexafluorophosphate to distilled water. Filter the precipitate generated in the solution and wash it with distilled water and diethyl ether, thereby obtaining brown solid Product 20 having a counter ion of $PF_6^-$. (521 mg, 91%) To convert the counter ion to $Cl^-$, dissolve the $PF_6^-$ product in a small amount (~1 mL) of acetonitrile, and then make an excess of distilled water (25 mL) mixture with $Cl^-$ ion exchange resin, and stir overnight. Filter the remaining $Cl^-$ resin and collect the filtrate, and remove the solvent using distillation under reduced pressure, thereby obtaining a product in which a counter ion is $Cl^-$. ESI-MS (Low resolution): Calcd for cation$[M]^+$ $C_{21}H_{22}Cl_2N_4O_2Os$: 624.07 Found: 624.25$[M]^+$.

2-4. $[Os(TPMA)Cl_2]^+(PF_6^-)$ Complex (21)

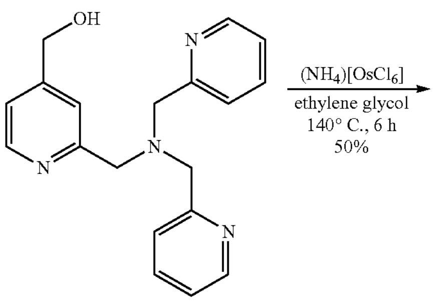

13

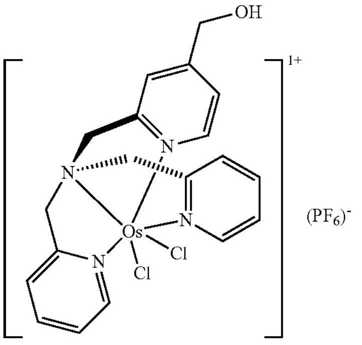

21

Put ammonium hexachloroosmate (62 mg, 0.141 mmol) and a starting material (13) (45 mg, 0.141 mmol) in a glass culture tube and add ethylene glycol (3 mL) to make a mixed solution. Then, blow argon gas for 10 minutes to create an argon atmosphere in the glass culture tube, and then reflux at 140° C. for 6 hours. Slowly drop the solution in which the reaction was completed into a saturated solution, by adding an excess of ammonium hexafluorophosphate to distilled water. Filter the precipitate generated in the solution and wash it with distilled water and diethyl ether, thereby obtaining brown solid Product 21 having a counter ion of $PF_6^-$. (51 mg, 50%) To convert the counter ion to $Cl^-$, dissolve the $PF_6^-$ product in a small amount (~1 mL) of acetonitrile, and then make an excess of distilled water (25 mL) mixture with $Cl^-$ ion exchange resin, and stir overnight. Filter the remaining $Cl^-$ resin and collect the filtrate, and remove the solvent using distillation under reduced pressure, thereby obtaining a product in which a counter ion is $Cl^-$. ESI-MS (Low resolution): Calcd for cation$[M]^+$ $C_{19}H_{20}Cl_2N_4OOs$: 582.06 Found: 566.2500$[M—OH]^+$.

2-5. $[Os(TPMA)Cl_2]+(PF_6^-)$ Complex (22)

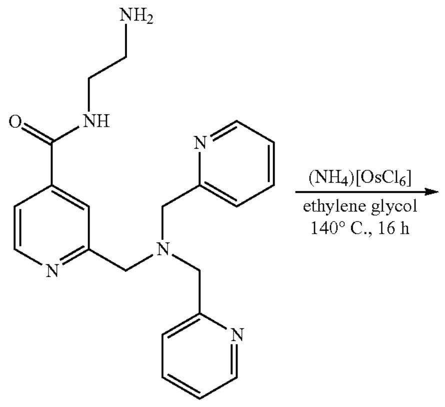

14

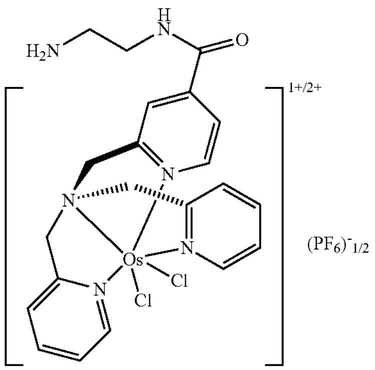

22

Put ammonium hexachloroosmate (326 mg, 0.742 mmol) and a starting material (14) (280 mg, 0.742 mmol) in a glass culture tube and add ethylene glycol (3 mL) to make a mixed solution. Then, blow argon gas for 10 minutes to create an argon atmosphere in the glass culture tube, and then reflux at 140° C. for 6 hours. Slowly drop the solution in which the reaction was completed into a saturated solution, by adding an excess of ammonium hexafluorophosphate to distilled water. Filter the precipitate generated in the solution and wash it with distilled water and diethyl ether, thereby obtaining brown solid Product 22 having a counter ion of $PF_6^-$. (355 mg, 61%) To convert the counter ion to $Cl^-$, dissolve the $PF_6^-$ product in a small amount (~1 mL) of acetonitrile, and then make an excess of distilled water (25 mL) mixture with $Cl^-$ ion exchange resin, and stir overnight. Filter the remaining $Cl^-$ resin and collect the filtrate, and remove the solvent using distillation under reduced pressure, thereby obtaining a product in which a counter ion is $Cl^-$. ESI-MS (High resolution): Calcd for cation$[M]^+$ $C_{21}H_{24}Cl_2N_6OOs$: 638.10 Found: 638.0998$[M]^+$, 319.5538 $[M]^{2+}$.

2-6. $[Os(TPMA)Cl_2]+(PF_6^-)$ Complex (23)

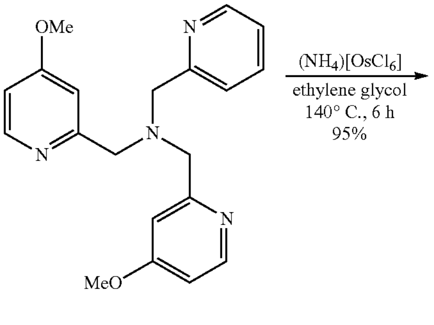

15

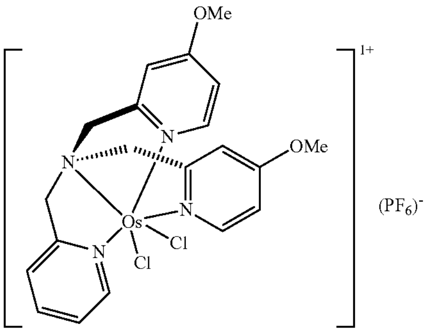

23

Put ammonium hexachloroosmate (129 mg, 0.293 mmol) and a starting material (15) (120 mg, 0.293 mmol) in a glass culture tube and add ethylene glycol (3 mL) to make a mixed solution. Then, blow argon gas for 10 minutes to create an argon atmosphere in the glass culture tube, and then reflux at 140° C. for 6 hours. Slowly drop the solution in which the reaction was completed into a saturated solution, by adding an excess of ammonium hexafluorophosphate to distilled water. Filter the precipitate generated in the solution and wash it with distilled water and diethyl ether, thereby obtaining brown solid Product 23 having a counter ion of $PF_6^-$. (220 mg, 95%) To convert the counter ion to $Cl^-$, dissolve the $PF_6^-$ product in a small amount (~1 mL) of acetonitrile, and then make an excess of distilled water (25 mL) mixture with $Cl^-$ ion exchange resin, and stir overnight. Filter the remaining $Cl^-$ resin and collect the filtrate, and remove the solvent using distillation under reduced pressure, thereby obtaining a product in which a counter ion is $Cl^-$. ESI-MS (Low resolution): Calcd for cation$[M]^+$ $C_{20}H_{22}Cl_2N_4O_2Os$: 612.07 Found: 612.16$[M]^+$.

2-7. $[Os(TPMA)(L)_{1-2}]^{n+}(PF_6^-)_n$ Complex (24)

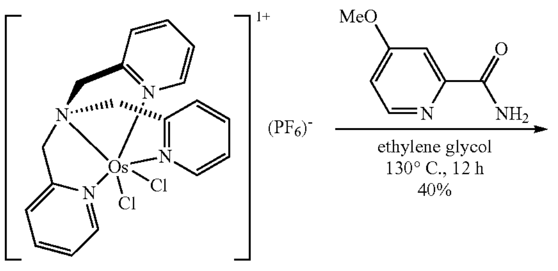

18

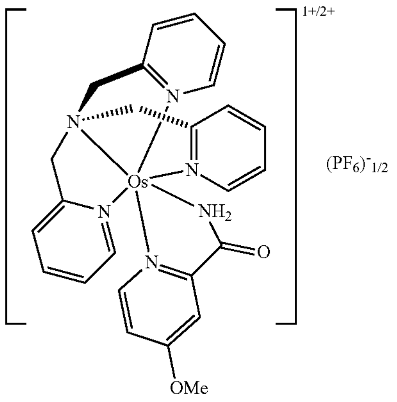

24

Put a starting material (18) (60 mg, 0.086 mmol) and 4-methoxy-2-pyridinecarboamide (65 mg, 0.430 mmol) in a glass culture tube and add ethylene glycol (3 mL) to make a mixed solution. Then, blow argon gas for 10 minutes to create an argon atmosphere in the glass culture tube, and then reflux at 130° C. for 12 hours. Slowly drop the solution in which the reaction was completed into a saturated solution, by adding an excess of ammonium hexafluorophosphate to distilled water. Filter the precipitate generated in the solution and wash it with distilled water and diethyl ether, thereby obtaining brown solid Product 24 having a counter ion of $PF_6^-$. (32 mg, 40%) To convert the counter ion to $Cl^-$, dissolve the $PF_6^-$ product in a small amount (~1 mL) of acetonitrile, and then make an excess of distilled water (25 mL) mixture with $Cl^-$ ion exchange resin, and stir overnight. Filter the remaining $Cl^-$ resin and collect the filtrate, and remove the solvent using distillation under reduced pressure, thereby obtaining a product in which a counter ion is $Cl^-$. ESI-MS (Low resolution): Calcd for cation$[M]^+$ $C_{25}H_{26}N_6O_2Os$: 634.17 Found: 634.2500$[M]^+$, 317.1667 $[M]^{2+}$.

2-8. $[Os(TPMA)(L)_{1-2}]^{n+}(PF_6^-)_n$ Complex (25)

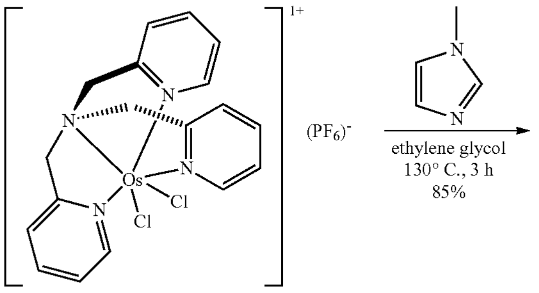

18

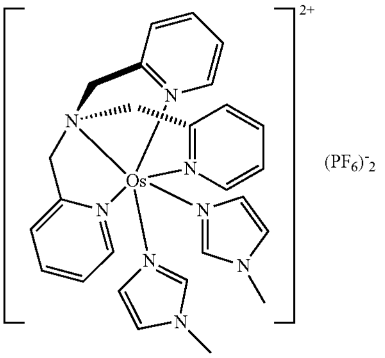

25

Put a starting material (18) (30 mg, 0.043 mmol) and N-methylimidazole (35 mg, 0.430 mmol) in a glass culture tube and add ethylene glycol (1.5 mL) to make a mixed solution. Then, blow argon gas for 10 minutes to create an argon atmosphere in the glass culture tube, and then reflux at 130° C. for 3 hours. Slowly drop the solution in which the reaction was completed into a saturated solution, by adding an excess of ammonium hexafluorophosphate to distilled water. Filter the precipitate generated in the solution and wash it with distilled water and diethyl ether, thereby obtaining brown solid Product 25 having a counter ion of $PF_6^-$. (34 mg, 85%) To convert the counter ion to dissolve the $PF_6^-$ product in a small amount (~1 mL) of acetonitrile, and then make an excess of distilled water (25 mL) mixture with ion exchange resin, and stir overnight. Filter the remaining resin and collect the filtrate, and remove the solvent using distillation under reduced pressure, thereby obtaining a product in which a counter ion is $Cl^-$. ESI-MS (Low resolution): Calcd for cation$[M]^+$ $C_{26}H_{30}N_8Os$: 646.22 Found: 323.08$[M]^{2+}$.

2-9. $[Os(TPMA)(L)_{1-2}]^{n+}(PF_6^-)_n$ Complex (26)

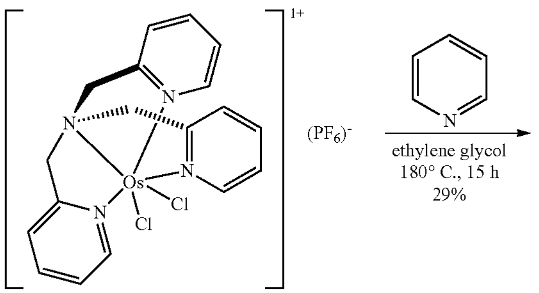

18

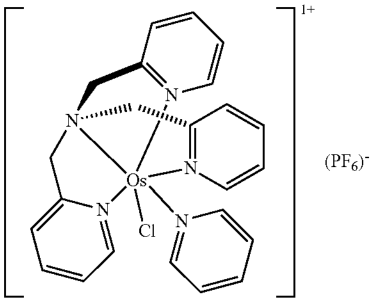

26

Put a starting material (18) (100 mg, 0.143 mmol) and pyridine (11 mg, 0.143 mmol) in a glass culture tube and add ethylene glycol (4 mL) to make a mixed solution. Then, blow argon gas for 10 minutes to create an argon atmosphere in the glass culture tube, and then reflux at 180° C. for 15 hours. Slowly drop the solution in which the reaction was completed into a saturated solution, by adding an excess of ammonium hexafluorophosphate to distilled water. Filter the precipitate generated in the solution and wash it with distilled water and diethyl ether, thereby obtaining brown solid Product 26 having a counter ion of $PF_6^-$. (31 mg, 29%) To convert the counter ion to dissolve the $PF_6^-$ product in a small amount (~1 mL) of acetonitrile, and then make an excess of distilled water (25 mL) mixture with ion exchange resin, and stir overnight. Filter the remaining resin and collect the filtrate, and remove the solvent using distillation under reduced pressure, thereby obtaining a product in which a counter ion is $Cl^-$. ESI-MS (Low resolution): Calcd for cation$[M]^+$ $C_{23}H_{23}ClN_5Os$: 596.13 Found: 596.3333 $[M]^+$.

2-10. $[Os(TPMA)(L)_{1-2}]^{n+}(PF_6^-)_n$ Complex (27)

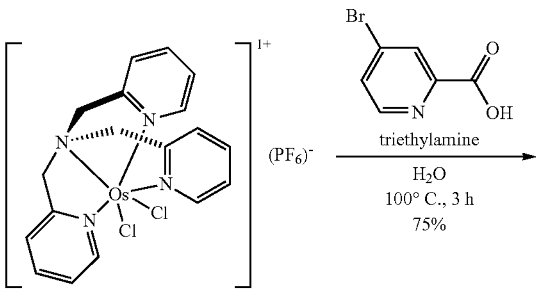

18

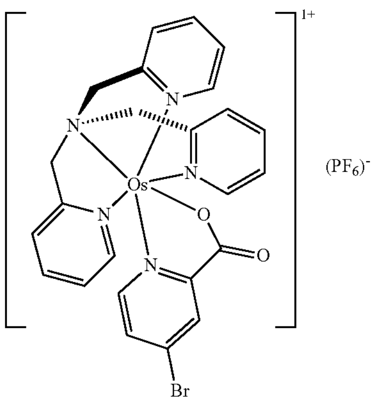

27

Put a starting material (18) (100 mg, 0.143 mmol) and 4-bromopicolinic acid (173 mg, 0.861 mmol), and triethylamine (145 mg, 1.430 mmol) in a glass culture tube and add distilled water (3 mL) to make a mixed solution. Then, blow argon gas for 10 minutes to create an argon atmosphere in the glass culture tube, and then reflux at 100° C. for 3 hours. Slowly drop the solution in which the reaction was completed into a saturated solution, by adding an excess of ammonium hexafluorophosphate to distilled water. Filter the precipitate generated in the solution and wash it with distilled water and diethyl ether, thereby obtaining brown solid Product 27 having a counter ion of $PF_6^-$. (89 mg, 75%) To convert the counter ion to $Cl^-$, dissolve the $PF_6^-$ product in a small amount (~1 mL) of acetonitrile, and then make an excess of distilled water (25 mL) mixture with $Cl^-$ ion exchange resin, and stir overnight. Filter the remaining $Cl^-$ resin and collect the filtrate, and remove the solvent using distillation under reduced pressure, thereby obtaining a product in which a counter ion is $Cl^-$. ESI-MS (Low resolution): Calcd for cation$[M]^+$ $C_{24}H_{21}BrN_5O_2Os$: 682.05 Found: 682.1667$[M]^+$.

2-11. $[Os(TPMA)(L)_{1-2}]^{n+}(PF_6^-)_n$ Complex (28)

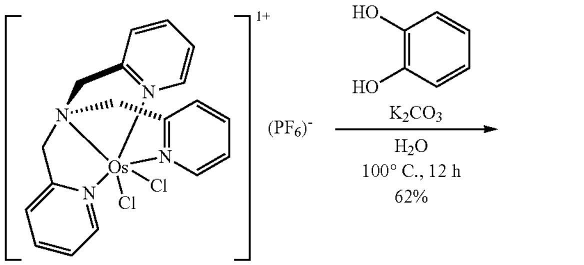

18

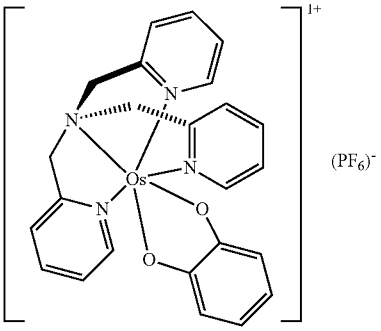

28

Put a starting material (18) (30 mg, 0.043 mmol) and catechol (47 mg, 0.430 mmol), and $K_2CO_3$ (59 mg, 0.430 mmol) in a glass culture tube and add distilled water (1.5 mL) to make a mixed solution. Then, blow argon gas for 10 minutes to create an argon atmosphere in the glass culture tube, and then reflux at 100° C. for 12 hours. Slowly drop the solution in which the reaction was completed into a saturated solution, by adding an excess of ammonium hexafluorophosphate to distilled water. Filter the precipitate generated in the solution and wash it with distilled water and diethyl ether, thereby obtaining black solid Product 28 having a counter ion of $PF_6^-$. (19.6 mg, 62%) To convert the counter ion to $Cl^-$, dissolve the $PF_6^-$ product in a small amount (~1 mL) of acetonitrile, and then make an excess of distilled water (25 mL) mixture with $Cl^-$ ion exchange resin, and stir overnight. Filter the remaining $Cl^-$ resin and collect the filtrate, and remove the solvent using distillation under reduced pressure, thereby obtaining a product in which a counter ion is $Cl^-$. ESI-MS (Low resolution): Calcd for cation$[M]^+$ $C_{24}H_{22}N_4O_2Os$: 590.14 Found: 590.2500$[M]^+$.

2-12. $[Os(TPMA)(L)_{1-2}]^{n+}(PF_6^-)_n$ Complex (29)

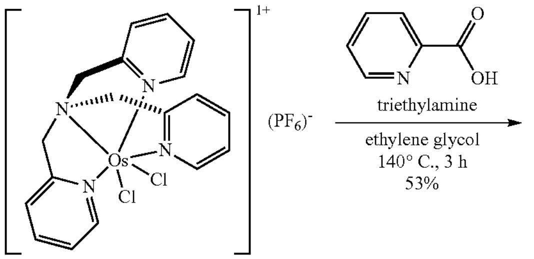

18

-continued

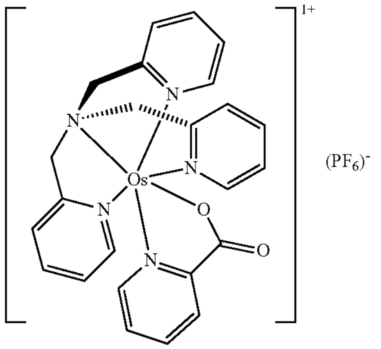

29

Put a starting material (18) (200 mg, 0.287 mmol) and 4-bromopicolinic acid (70 mg, 0.569 mmol) and triethylamine (29 mg, 0.287 mmol) in a glass culture tube and add ethylene glycol (3 mL) to make a mixed solution. Then, blow argon gas for 10 minutes to create an argon atmosphere in the glass culture tube, and then reflux at 140° C. for 3 hours. Slowly drop the solution in which the reaction was completed into a saturated solution, by adding an excess of ammonium hexafluorophosphate to distilled water. Filter the precipitate generated in the solution and wash it with distilled water and diethyl ether, thereby obtaining brown solid Product 29 having a counter ion of $PF_6^-$ (113 mg, 53%) To convert the counter ion to $Cl^-$, dissolve the $PF_6^-$ product in a small amount (~1 mL) of acetonitrile, and then make an excess of distilled water (25 mL) mixture with $Cl^-$ ion exchange resin, and stir overnight. Filter the remaining $Cl^-$ resin and collect the filtrate, and remove the solvent using distillation under reduced pressure, thereby obtaining a product in which a counter ion is $Cl^-$. ESI-MS (High resolution): Calcd for cation$[M]^+$ $C_{24}H_{22}N_5O_2Os$: 604.14 Found: 604.13824$[M]^+$.

2-13. $[Os(TPMA)(L)_{1-2}]^{n+}(PF_6^-)_n$ Complex (30)

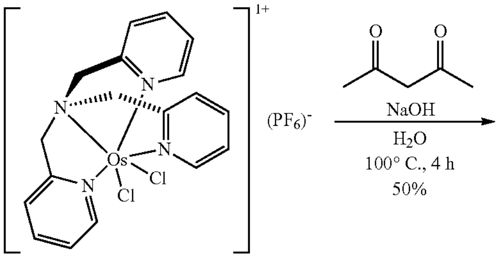

18

-continued

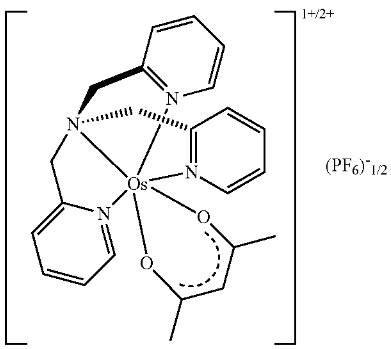

30

-continued

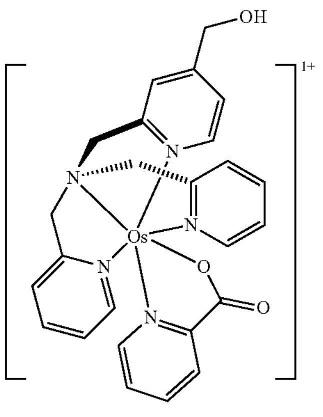

31

Put a starting material (18) (30 mg, 0.043 mmol) and acetylacetone (43 mg, 0.430 mmol), and NaOH (8 mg, 0.215 mmol) in a glass culture tube and add distilled water (1.5 mL) to make a mixed solution. Then, blow argon gas for 10 minutes to create an argon atmosphere in the glass culture tube, and then reflux at 100° C. for 4 hours. Slowly drop the solution in which the reaction was completed into a saturated solution, by adding an excess of ammonium hexafluorophosphate to distilled water. Filter the precipitate generated in the solution and wash it with distilled water and diethyl ether, thereby obtaining black solid Product 30 having a counter ion of $PF_6^-$. (16 mg, 50%) To convert the counter ion to $Cl^-$, dissolve the $PF_6^-$ product in a small amount (~1 mL) of acetonitrile, and then make an excess of distilled water (25 mL) mixture with $Cl^-$ ion exchange resin, and stir overnight. Filter the remaining $Cl^-$ resin and collect the filtrate, and remove the solvent using distillation under reduced pressure, thereby obtaining a product in which a counter ion is $Cl^-$. ESI-MS (Low resolution): Calcd for cation$[M]^+$ $C_{23}H_{25}N_4O_2Os$: 581.16 Found: 581.3333$[M]^+$, 290.6666$[M]^{2+}$.

2-14. $[Os(TPMA)(L)_{1-2}]^{n+}(PF_6^-)_n$ Complex (31)

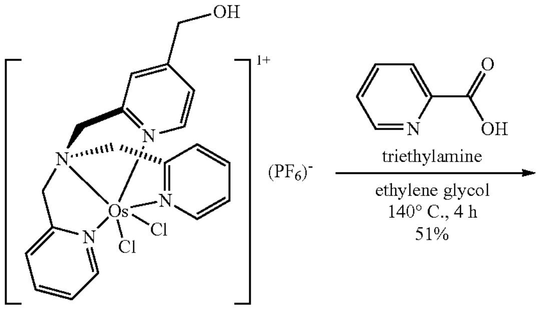

21

Put a starting material (21) (100 mg, 0.137 mmol) and picolinic acid (67 mg, 0.548 mmol) and triethylamine (56 mg, 0.548 mmol) in a glass culture tube and add ethylene glycol (3 mL) to make a mixed solution. Then, blow argon gas for 10 minutes to create an argon atmosphere in the glass culture tube, and then reflux at 140° C. for 4 hours. Slowly drop the solution in which the reaction was completed into a saturated solution, by adding an excess of ammonium hexafluorophosphate to distilled water. Filter the precipitate generated in the solution and wash it with distilled water and diethyl ether, thereby obtaining brown solid Product 31 having a counter ion of $PF_6^-$. (54 mg, 51%) To convert the counter ion to $Cl^-$, dissolve the $PF_6^-$ product in a small amount (~1 mL) of acetonitrile, and then make an excess of distilled water (25 mL) mixture with $Cl^-$ ion exchange resin, and stir overnight. Filter the remaining $Cl^-$ resin and collect the filtrate, and remove the solvent using distillation under reduced pressure, thereby obtaining a product in which a counter ion is $Cl^-$. ESI-MS (Low resolution): Calcd for cation$[M]^+$ $C_{25}H_{24}N_5O_3Os$: 634.15 Found: 618.3333[M—OH]$^+$.

2-15. $[Os(TPMA)(L)_{1-2}]^{n+}(PF_6^-)_n$ Complex (32)

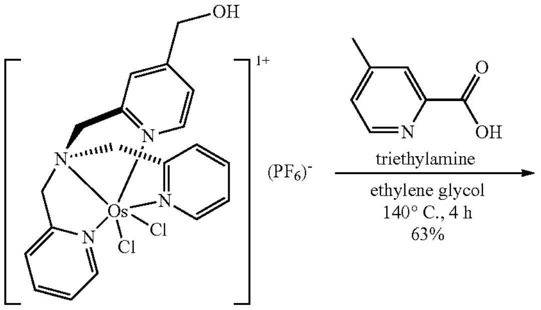

21

-continued

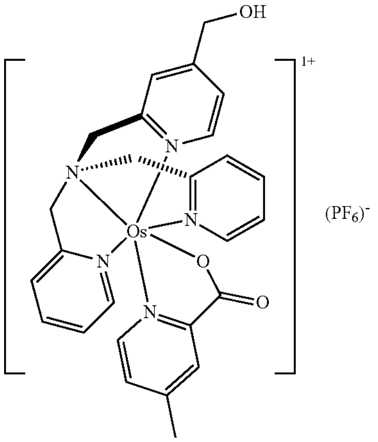

32

Put a starting material (21) (100 mg, 0.137 mmol) and 4-methylpicolinic acid (76 mg, 0.550 mmol) and triethylamine (56 mg, 0.550 mmol) in a glass culture tube and add ethylene glycol (3 mL) to make a mixed solution. Then, blow argon gas for 10 minutes to create an argon atmosphere in the glass culture tube, and then reflux at 140° C. for 4 hours. Slowly drop the solution in which the reaction was completed into a saturated solution, by adding an excess of ammonium hexafluorophosphate to distilled water. Filter the precipitate generated in the solution and wash it with distilled water and diethyl ether, thereby obtaining brown solid Product 32 having a counter ion of $PF_6^-$. (58 mg, 53%) To convert the counter ion to $Cl^-$, dissolve the $PF_6^-$ product in a small amount (~1 mL) of acetonitrile, and then make an excess of distilled water (25 mL) mixture with $Cl^-$ ion exchange resin, and stir overnight. Filter the remaining $Cl^-$ resin and collect the filtrate, and remove the solvent using distillation under reduced pressure, thereby obtaining a product in which a counter ion is $Cl^-$. ESI-MS (Low resolution): Calcd for cation$[M]^+$ $C_{26}H_{26}N_5O_3Os$: 648.17 Found: 632.4167$[M—OH]^+$.

2-16. $[Os(TPMA)(L)_{1-2}]^{n+}(PF_6^-)_n$ Complex (33)

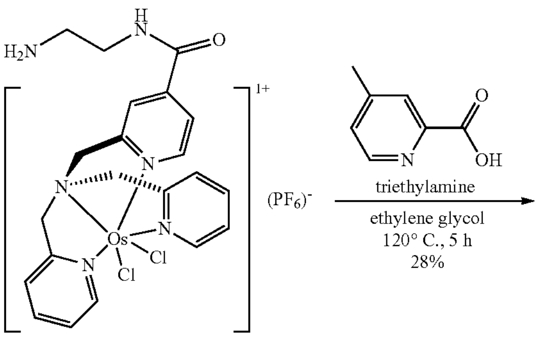

22

-continued

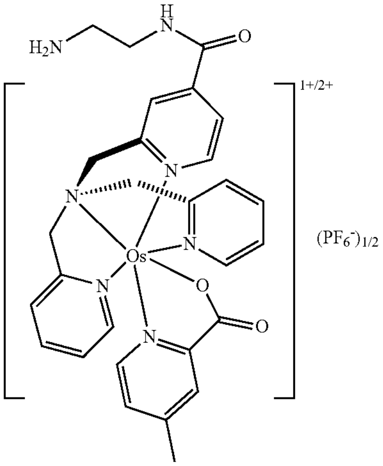

33

Put a starting material (22) (40 mg, 0.051 mmol) and 4-methylpicolinic acid (28 mg, 0.204 mmol) and triethylamine (15 mg, 153 mmol) in a glass culture tube and add ethylene glycol (3 mL) to make a mixed solution. Then, blow argon gas for 10 minutes to create an argon atmosphere in the glass culture tube, and then reflux at 120° C. for 5 hours. Slowly drop the solution in which the reaction was completed into a saturated solution, by adding an excess of ammonium hexafluorophosphate to distilled water. Filter the precipitate generated in the solution and wash it with distilled water and diethyl ether, thereby obtaining brown solid Product 33 having a counter ion of $PF_6^-$. (12 mg, 28%) To convert the counter ion to $Cl^-$, dissolve the $PF_6^-$ product in a small amount (~1 mL) of acetonitrile, and then make an excess of distilled water (25 mL) mixture with $Cl^-$ ion exchange resin, and stir overnight. Filter the remaining $Cl^-$ resin and collect the filtrate, and remove the solvent using distillation under reduced pressure, thereby obtaining a product in which a counter ion is $Cl^-$. ESI-MS (High resolution): Calcd for cation$[M]^+$ $C_{28}H_{30}N_7O_3Os$: 704.20 Found: 704.2019$[M]^+$, 352.6044$[M]^{2+}$.

2-17. $[Os(TPMA)(L)_{1-2}]^{n+}(PF_6^-)_n$ Complex (34)

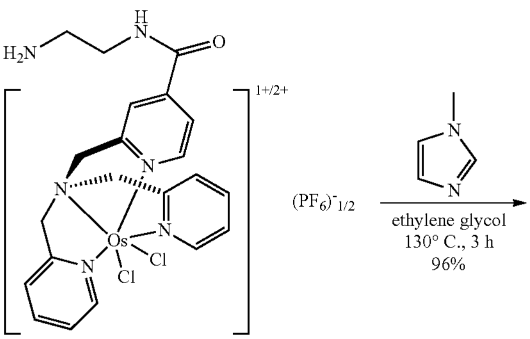

22

-continued

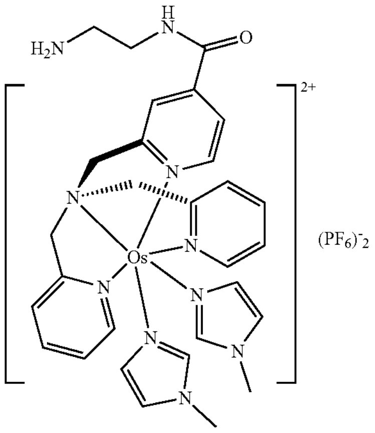

34

Put a starting material (22) (40 mg, 0.051 mmol) and N-methylimidazole (42 mg, 0.510 mmol) in a glass culture tube and add ethylene glycol (2 mL) to make a mixed solution. Then, blow argon gas for 10 minutes to create an argon atmosphere in the glass culture tube, and then reflux at 130° C. for 3 hours. Slowly drop the solution in which the reaction was completed into a saturated solution, by adding an excess of ammonium hexafluorophosphate to distilled water. Filter the precipitate generated in the solution and wash it with distilled water and diethyl ether, thereby obtaining brown solid Product 34 having a counter ion of $PF_6^-$. (50 mg, 96%) To convert the counter ion to $Cl^-$, dissolve the $PF_6^-$ product in a small amount (~1 mL) of acetonitrile, and then make an excess of distilled water (25 mL) mixture with ion exchange resin, and stir overnight. Filter the remaining resin and collect the filtrate, and remove the solvent using distillation under reduced pressure, thereby obtaining a product in which a counter ion is $Cl^-$. ESI-MS (High resolution): Calcd for cation$[M]^+$ $C_{29}H_{36}N_{10}OOs$: 732.27 Found: $367.1182[M+2]^{2+}$.

2-18. $[Os(TPMA)(L)_{1-2}]^{n+}(PF_6^-)_n$ Complex (35)

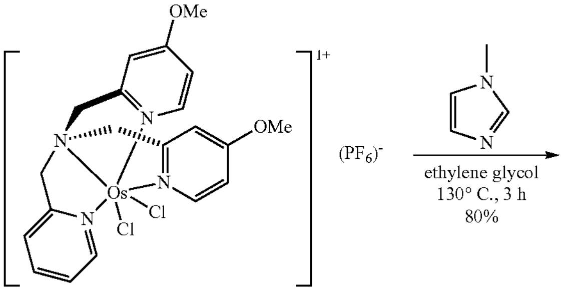

23

-continued

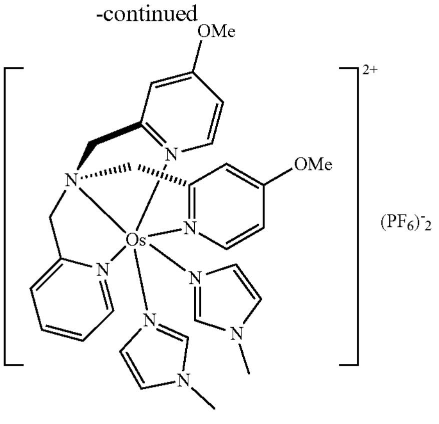

35

Put a starting material (23) (30 mg, 0.040 mmol) and N-methylimidazole (32 mg, 0.400 mmol) in a glass culture tube and add ethylene glycol (1.5 mL) to make a mixed solution. Then, blow argon gas for 10 minutes to create an argon atmosphere in the glass culture tube, and then reflux at 130° C. for 3 hours. Slowly drop the solution in which the reaction was completed into a saturated solution, by adding an excess of ammonium hexafluorophosphate to distilled water. Filter the precipitate generated in the solution and wash it with distilled water and diethyl ether, thereby obtaining brown solid Product 35 having a counter ion of $PF_6^-$. (31 mg, 80%) To convert the counter ion to $Cl^-$, dissolve the $PF_6^-$ product in a small amount (~1 mL) of acetonitrile, and then make an excess of distilled water (25 mL) mixture with $Cl^-$ ion exchange resin, and stir overnight. Filter the remaining $Cl^-$ resin and collect the filtrate, and remove the solvent using distillation under reduced pressure, thereby obtaining a product in which a counter ion is $Cl^-$. ESI-MS (Low resolution): Calcd for cation$[M]^+$ $C_{28}H_{34}N_8O_2Os$: 706.24 Found: $353.2500[M]^{2+}$.

Example 3. Analysis of Electrochemical Properties of TPMA-Based Osmium Complexes According to the Present Invention In order to analyze electrochemical properties of the synthesized TPMA-based osmium complexes, cyclic voltammetry (CV) was used. A well-washed carbon glass electrode with a diameter of 3 mm was used as a working electrode, and an Ag/AgCl electrode was used as a reference electrode, and a Pt electrode was used as a counter electrode to measure it at a scanning rate of 10 mV/s. The complex in a $PF_6^-$ counter ion form was measured in an acetonitrile solution of TBAP of 0.1 M at a concentration of 3 mg/mL. In order to find out only the position of the redox peak, the complex in a $Cl^-$ counter ion form was measured in condition that the concentration of each substance was not constant, by measuring the $Cl^-$ substance in a solution state during the anion exchange process. The oxidation/reduction potentials of all the synthesized TPMA-based osmium complexes were shown in FIGS. 7*a* to *c*. $[Os(TPMA)Cl_2]^+(Cl^-)$ (18) is the most basic TPMA osmium complex without any substituent, and exhibited an oxidation/reduction potential of $E_{1/2}$=−0.339 V, and this result was shown in FIG. 6. The change in the oxidation/reduction potential according to the type of the substituent and coordinated ligand was analyzed centering on the present complex.

Oxidation/reduction potentials were compared with Complexes Nos. 19~23 each other, which have a similar coordination structure to Complex No. 18 and comprise different substituents, respectively. Complexes comprising an electron withdrawing group (EWG) such as Complex No. 19 comprising 2 ethylester (—COOEt) groups and Complex No. 20 comprising one and Complex No. 22 comprising an amide (—COONH) group showed more positive values than the oxidation/reduction potential of Complex No. 18. On the other hand, complexes comprising an electron donating group (EDG) such as No. 21 comprising a methyl (—$CH_{2-}$) group and No. 23 comprising 2 methoxy (—OMe) groups were observed in a more negative value. This result shows that EWG decreases the electron density of the central metal and the potential shifts in the positive direction due to the tendency for reduction, while EDG increases the electron density and the potential appears in a more negative direction due to the tendency to oxidize well. Complexes Nos. 20, 22 moved in a positive direction by about 0.102~0.103 V than the oxidation/reduction potential of Complex No. 18, and both complexes showed similar oxidation/reduction potentials, indicating that the ester group comprising a carbonyl group and the amide group had similar electrochemical effects. Complex No. 19 shifted in a positive direction by about 0.176 V than the oxidation/reduction potential of Complex No. 18, and it was confirmed that the more EWG there was, the greater the electrochemical effect. Complex No. 21 comprising a hydroxymethyl group slight shifted in a negative direction by 0.031 V, and Complex No. 23 comprising 2 methoxy group, which is a better EDG, shifted in a negative direction by 0.125 V, and therefore, it was judged to have a greater effect according to the kind and number of the EDG. Through this result, it is possible to change the potential of the TPMA-based osmium complexes depending on the substituent, and through this, the possibility of application and improvement as an electron transfer mediator with an ideal oxidation/reduction potential was confirmed.

$[Os(TPMA)(L)_{1-2}]^{n+}(PF_6^-)_n$-based complexes (24~30) coordinated with various ligands all showed an increased oxidation/reduction potential in a positive direction than Complex No. 18. In order of acetylacetone, 1 pyridine, 4-bromopicolinic acid, picolinic acid, 2 of 1-methylimidazole, 4-methoxy-2-pyridylcarboxyamide, and catechol, the oxidation/reduction potential showed a large increase in a positive direction. Complexes No. 25, 28 in which 4-methoxy-2-pyridylcarboxyamide and catechol were coordinated, respectively, showed two or more reversible oxidation/reduction peaks, and did not exhibit a single stable oxidation/reduction potential, and thus, they were judged to be unsuitable as an electron transfer mediator. However, since the picolinic acid-coordinated TPMA osmium compound exhibited an ideal oxidation/reduction potential close to 0 V with respect to the Ag/AgCl electrode, as the potential value shifted in a moderately positive direction, it was judged to be an appropriate TPMA-based osmium complex with potential to be applied to an electron transfer mediator. In addition, characteristically, $[Os(TPMA)Cl_2]^+(X^-)$-based Complex 18~23 showed almost similar redox potentials under a solvent condition different each other according to the counter ion form, but except for these, all $[Os(TPMA)(L)_{1-2}]^{n+}(PF_6^-)_n$-based complexes showed oxidation/reduction potentials in a more negative region from a small 36 mV to a large 210 mV in the $Cl^-$ counter ion form than the $PF_6^-$ counter ion form.

The invention claimed is:

1. A electrochemical blood glucose sensor comprising a transition metal complex, wherein the transition metal complex comprises a tetradentate nitrogen donor ligand represented by Chemical formula 1 or 2 below, as an electron transfer mediator:

[Chemical formula 1]

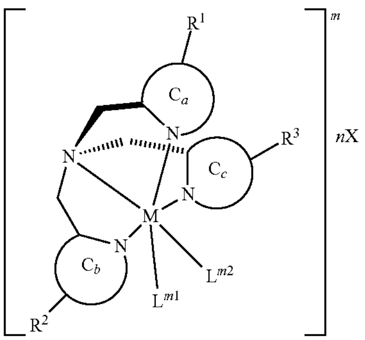

[Chemical formula 2]

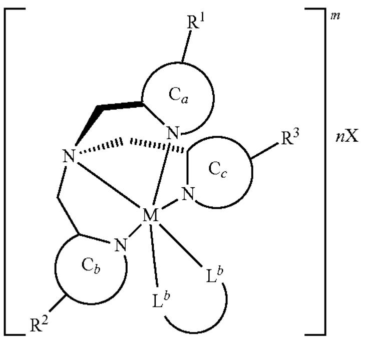

in the Chemical formula 1 or Chemical formula 2,

M is Os; and $C_a$, $C_b$, $C_c$ are heterocyclic compounds comprising one or more nitrogen atoms, and are linked to an amine group and a methylene group at the position 2 of the cyclic compound; and $L^{m1}$ and $L^{m2}$ are each independently —H, —F, —Cl, —Br, —I, —$NO_2$, —$NCCH_3$, —CO, —$OH_2$, —$NH_3$ or a heterocyclic compound comprising one or more nitrogen atoms;

$L^b$-$L^b$ is catechol, acetylacetone, 2-picolinic acid, 2-pyridinecarboxamide, 2,2-bipyridine or 2,2-bithiazole;

m is a negative charge from −1 to −5 or positive charge from +1 to +5; and $R^1$, $R^2$ and $R^3$ are each independently —H; —F; —Cl; —Br; —I; —$NO_2$; —CN; —$CO_2H$; —$SO_3H$; —$NHNH_2$; —SH; —OH; —$NH_2$; —$CH_2OH$; —$CONHCH_2CH_2NH_2$; or substituted or unsubstituted alkoxycarbonyl, alkylaminocarbonyl, dialkylaminocarbonyl, alkoxy, alkylamino, dialkylamino, alkanylamino, arylcarboxyamido, hydrazino, alkylhydrazino, hydroxyamino, alkoxyamino, alkylthio, alkenyl, aryl or alkyl; and X is a counter ion; and n means the number of counter ions, and is within the integer range 1 to 5.

2. The electrochemical blood glucose sensor according to claim 1, wherein the electrochemical blood glucose sensor is an electrochemical biosensor or insertable device.

3. The electrochemical blood glucose sensor according to claim 1, wherein the heterocyclic compound is one or more kinds selected from the group consisting of imidazole, pyridine, pyrimidine, pyrazole, isoxazole, oxazole, thiazole, benzothiazole, benzimidazole, benzoxazole and diazafluorenone.

4. The electrochemical blood glucose sensor according to claim 1, wherein the transition metal complex of the Chemical formula 1 or 2 is one of the following transition metal complexes:

| complex No. | Chemical structure of transition metal complex |
|---|---|
| 18 | 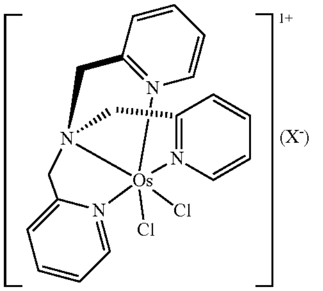 |
| 19 | 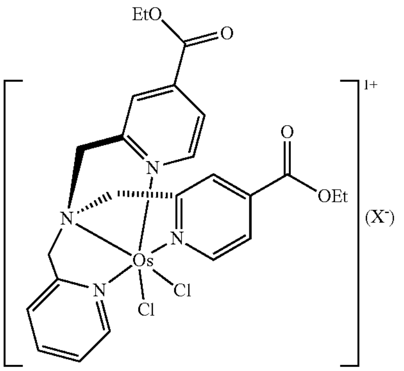 |
| 20 | 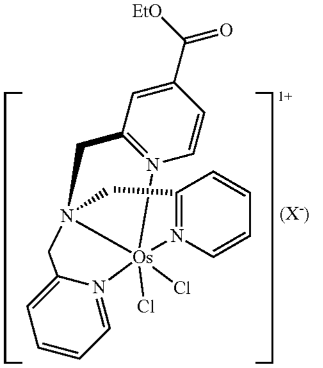 |

-continued

| complex No. | Chemical structure of transition metal complex |
|---|---|
| 21 | 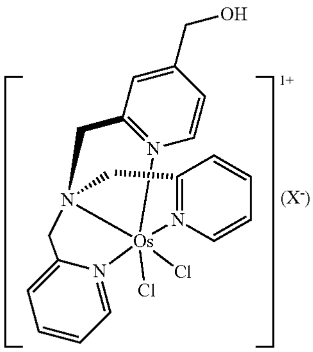 |
| 22 | 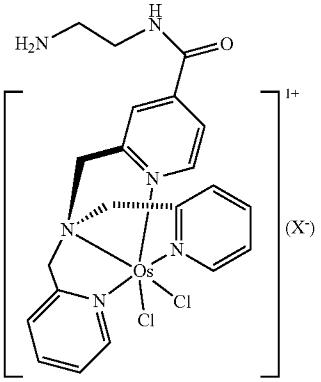 |
| 23 | 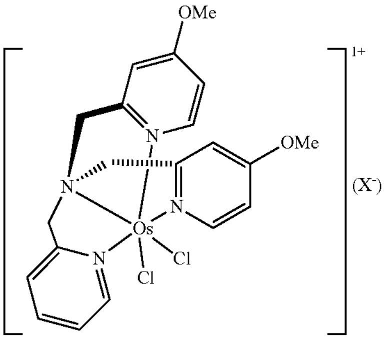 |
| 24 | 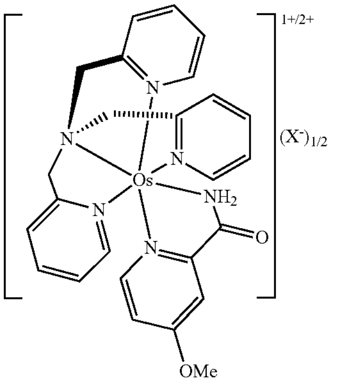 |

-continued
| complex No. | Chemical structure of transition metal complex |
|---|---|
| 25 | 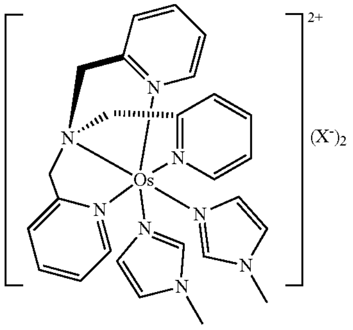 |
| 26 | 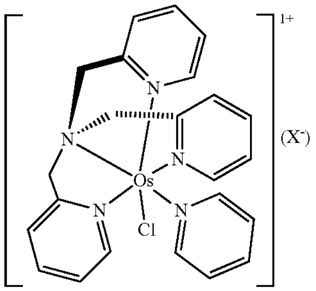 |
| 27 | 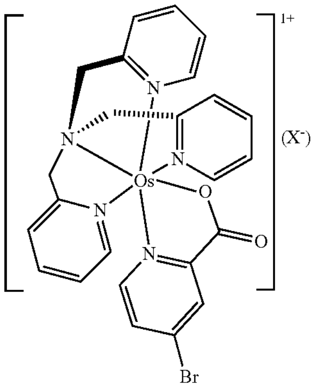 |
| 28 | 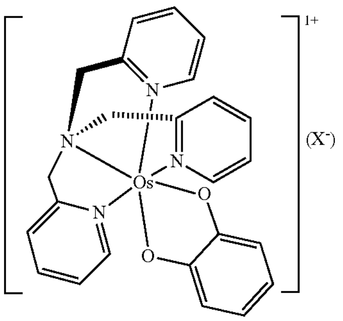 |
-continued
| complex No. | Chemical structure of transition metal complex |
|---|---|
| 29 | 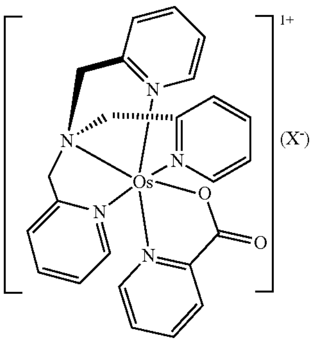 |
| 30 | 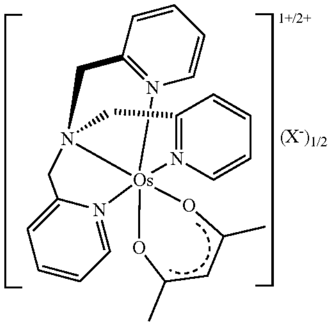 |
| 31 | 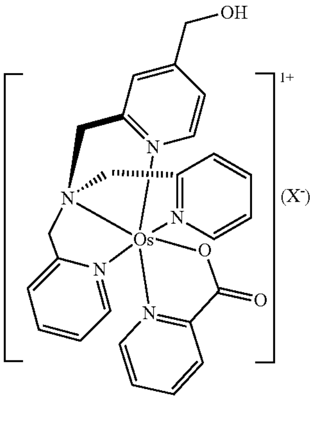 |

-continued
| complex No. | Chemical structure of transition metal complex |
|---|---|
| 32 | 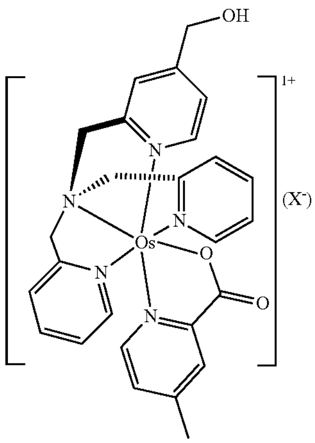 |
| 33 | 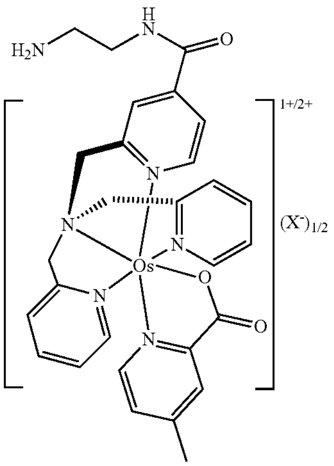 |
-continued
| complex No. | Chemical structure of transition metal complex |
|---|---|
| 34 | 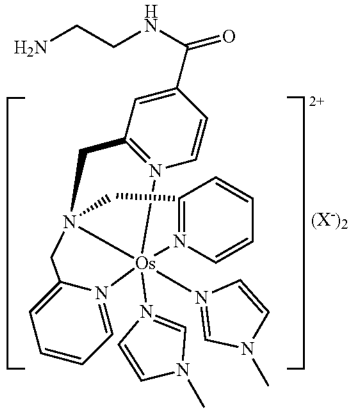 |
| 35 | 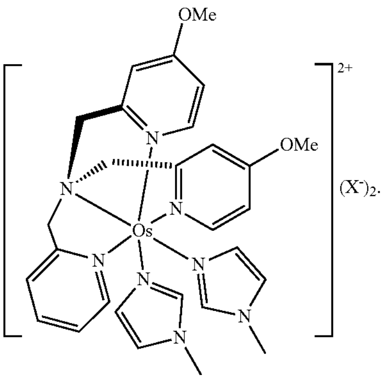 |
* * * * *